(12) United States Patent
Sakai et al.

(10) Patent No.: US 9,518,011 B2
(45) Date of Patent: Dec. 13, 2016

(54) RECORDING MATERIAL PRODUCED USING NON-PHENOL COMPOUND

(71) Applicant: NIPPON SODA CO., LTD., Tokyo (JP)

(72) Inventors: Hiroshi Sakai, Ichihara (JP); Tadahiro Kondo, Takaoka (JP); Kayoko Tada, Ichihara (JP); Shuntaro Kinoshita, Ichihara (JP); Kazumi Jyujyo, Tokyo (JP)

(73) Assignee: NIPPON SODA CO., LTD., Tokyo (JP)

( * ) Notice: Subject to any disclaimer, the term of this patent is extended or adjusted under 35 U.S.C. 154(b) by 0 days.

(21) Appl. No.: 14/441,941

(22) PCT Filed: Nov. 19, 2013

(86) PCT No.: PCT/JP2013/006780
§ 371 (c)(1),
(2) Date: May 11, 2015

(87) PCT Pub. No.: WO2014/080615
PCT Pub. Date: May 30, 2014

(65) Prior Publication Data
US 2015/0284321 A1 Oct. 8, 2015

(30) Foreign Application Priority Data

Nov. 21, 2012 (JP) ................... 2012-255337

(51) Int. Cl.
| | | |
|---|---|---|
| B41M 5/155 | (2006.01) |
| B41M 5/333 | (2006.01) |
| C07C 311/21 | (2006.01) |
| C07C 311/46 | (2006.01) |
| C07C 311/47 | (2006.01) |
| C07C 311/29 | (2006.01) |
| C09D 11/037 | (2014.01) |

(52) U.S. Cl.
CPC ............ *C07C 311/47* (2013.01); *B41M 5/155* (2013.01); *B41M 5/3333* (2013.01); *B41M 5/3336* (2013.01); *C07C 311/21* (2013.01); *C07C 311/29* (2013.01); *C07C 311/46* (2013.01); *C09D 11/037* (2013.01); *Y10T 428/24802* (2015.01)

(58) Field of Classification Search
CPC ..... B41M 5/155; B41M 5/333; B41M 5/3336; C07C 311/21; C07C 311/46; C07C 311/47
USPC .......................... 503/216; 564/49; 106/31.17
See application file for complete search history.

(56) References Cited

U.S. PATENT DOCUMENTS

| | | | |
|---|---|---|---|
| 3,996,253 A | 12/1976 | Magagnoli et al. |
| 6,262,113 B1 | 7/2001 | Widdowson et al. |
| 6,624,117 B1 | 9/2003 | Heneghan et al. |
| 2009/0163545 A1 | 6/2009 | Goldfarb |
| 2010/0048573 A1 | 2/2010 | Sperandio et al. |
| 2011/0275635 A1 | 11/2011 | Brouillette et al. |
| 2012/0196884 A1 | 8/2012 | Koivunen et al. |
| 2013/0345436 A1 | 12/2013 | Jiang et al. |
| 2014/0371291 A1 | 12/2014 | Mori et al. |

FOREIGN PATENT DOCUMENTS

| | | |
|---|---|---|
| JP | H11-503110 A | 3/1999 |
| JP | H11-268421 A | 10/1999 |
| JP | 2000-504722 A | 4/2000 |
| JP | 2002-526472 A | 8/2002 |

(Continued)

OTHER PUBLICATIONS

May 26, 2015 International Preliminary Report on Patentability issued in International Patent Application No. PCT/JP2013/006780.

(Continued)

*Primary Examiner* — Bruce H Hess
(74) *Attorney, Agent, or Firm* — Oliff PLC

(57) ABSTRACT

An object of the present invention is to provide a recording material or a recording sheet using, as a color-developing agent, a non-phenol compound that is a safe compound in no danger of corresponding to an endocrine disruptor and is good in color developing performance. The non-phenol compound used in the present invention is at least one selected from the group consisting of compounds represented by the following formulas (I) to (III).

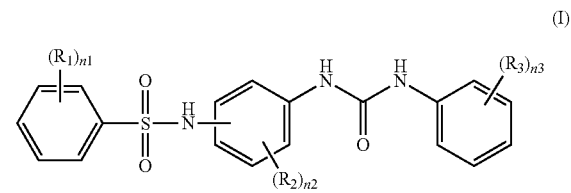

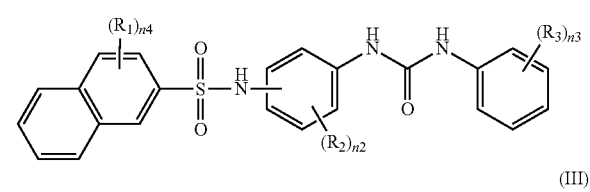

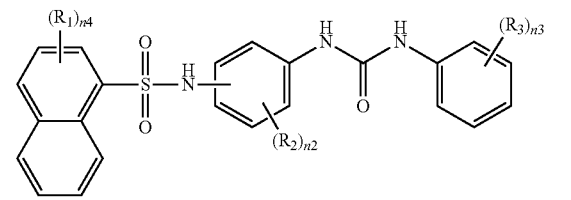

8 Claims, No Drawings

(56) References Cited

FOREIGN PATENT DOCUMENTS

| JP | 2002-532441 A | 10/2002 |
|---|---|---|
| JP | 2011-507910 A | 3/2011 |
| WO | 96/25157 A1 | 8/1996 |
| WO | 97/29743 A1 | 8/1997 |
| WO | 00/17159 A1 | 3/2000 |
| WO | 01/51456 A2 | 7/2001 |
| WO | 2004/064728 A2 | 8/2004 |
| WO | 2010/146236 A1 | 12/2010 |
| WO | 2012/088776 A1 | 7/2012 |
| WO | 2013/111798 A1 | 8/2013 |

OTHER PUBLICATIONS

Moro et al., "SAR Studies for a New Class of Antibacterial NAD Biosynthesis Inhibitors", Journal of Combinatorial Chemistry, 2009, pp. 617-625, vol. 11, No. 4.
Dec. 17, 2013 Search Report issued in International Patent Application No. PCT/JP2013/006780.
Jun. 9, 2016 Extended European Search Report issued in European Application No. 13856824.1.

RECORDING MATERIAL PRODUCED USING NON-PHENOL COMPOUND

TECHNICAL FIELD

The present invention relates to a thermal or pressure-sensitive recording material employing color development through a reaction between a color former and a color-developing agent.

The present application claims priority based on Japanese Patent Application No. 2012-255337 filed on Nov. 21, 2012, and the contents thereof are incorporated herein by reference in their entirety.

BACKGROUND ART

Recording materials that employ color development through a reaction between a color former and a color-developing agent allow recording in a short time using a relatively simple apparatus without performing complicated treatments such as development and fixation and are thus widely used in thermal recording paper for output recording in facsimiles, printers, etc., or pressure-sensitive copying paper or the like for forms for simultaneous multiple copying. These recording materials are required to immediately develop colors, maintain the whiteness of an uncolored part (hereinafter, referred to as a "background"), and offer high colorfastness of colored images. Particularly, recording materials excellent in the heat resistance of a background and images are desired in terms of long-term storage stability. For this purpose, attempts have been made to develop color former, color-developing agents, storage stabilizers, etc. Nevertheless, recording materials that have well-balanced, sufficiently satisfactory color-developing sensitivity, background and image stabilities, etc., have not been found yet.

Besides, as recording materials excellent in the background stability, 4-hydroxy-4'-isopropoxydiphenylsulfone, etc. are conventionally known, but their heat resistance is not still satisfactory.

On the other hand, although a phenol color-developing agent such as 4,4'-isopropylidene diphenol shows good color-developing performance, such an agent can correspond to an endocrine disruptor and is not allowed to be used for some users. Therefore, a color-developing agent having a structure not containing a phenol skeleton (which structure is hereinafter referred to as the non-phenol) is required.

Patent Document 1 describes a non-phenol color-developing agent. A synthesis method for this color-developing agent is, however, complicated, and in addition, this agent is inferior in plasticizer resistance. Patent Document 2 describes a sulfonamide color-developing agent. Although such a color-developing agent is good in the color developing performance, one having a sulfonyloxy phenyl group is poor in water resistance, and in addition, if a sulfonyloxy group having a hydrolyzable property is decomposed, a phenol compound is produced.

Therefore, the present inventors have found that a compound having structures of both N-phenyl benzenesulfonamide and carbanilide can be used as a color-developing agent. As the compound having such a structure, sulfonamide compounds described in Patent Document 3 are known, but these compounds are used for preventing infection with microorganisms such as bacteria, and use as a color-developing agent is not disclosed.

PRIOR ART DOCUMENTS

Patent Documents

Patent Document 1: Japanese unexamined Patent Application Publication No. 11-268421
Patent Document 2: Japanese unexamined Patent Application Publication (Translation of PCT Application) No. 2002-532441
Patent Document 3: International Publication No. WO2010/146236 pamphlet

SUMMARY OF THE INVENTION

Object to be Solved by the Invention

An object of the present invention is to provide a recording material or a recording sheet using, as a color-developing agent, a non-phenol compound good in color developing performance and plasticizer resistance.

Means to Solve the Object

The present inventors have found a compound having a non-phenol structure and difficult to be decomposed by water, and found that this compound is good as a color-developing agent in color developing performance, heat resistance and plasticizer resistance, resulting in accomplishing the present invention.

Specifically, the present invention relates to:
(1) A recording material containing a color former, wherein the recording material contains at least one compound selected from the group consisting of:
a compound represented by the following formula (I):

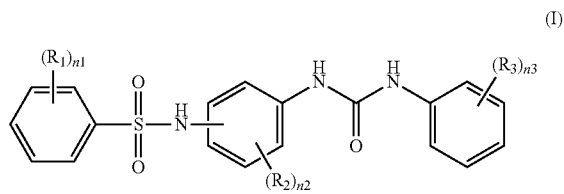

(wherein $R_1$ to $R_3$ represent a hydrogen atom, a halogen atom, a nitro group, a $C_1$-$C_6$ alkyl group, a $C_1$-$C_6$ alkoxyl group, a $C_2$-$C_6$ alkenyl group, a $C_1$-$C_6$ fluoroalkyl group, a $N(R_4)_2$ group (wherein $R_4$ represents a hydrogen atom, a phenyl group, a benzyl group, or a $C_1$-$C_6$ alkyl group), $NHCOR_5$ (wherein $R_5$ represents a $C_1$-$C_6$ alkyl group), an optionally substituted phenyl group, or an optionally substituted benzyl group; n1 and n3 each independently represent any integer of 1 to 5; and n2 represents any integer of 1 to 4);
a compound represented by the following formula (II):

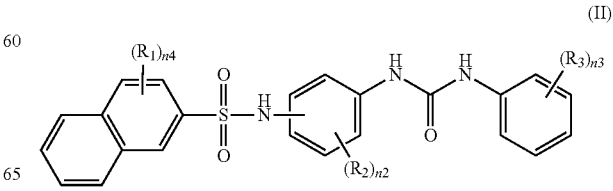

(wherein $R_1$ to $R_3$ represent the same as $R_1$ to $R_3$ defined in the formula (I); n2 and n3 represent the same as n2 and n3 defined in the formula (I); and n4 represents any integer of 1 to 7); and a compound represented by the following formula (III):

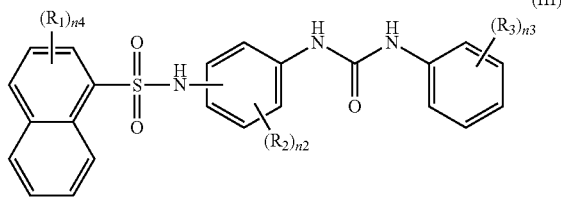

(III)

(wherein $R_1$ to $R_3$ represent the same as $R_1$ to $R_3$ defined in the formula (I); and n2, n3 and n4 represent the same as n2, n3 and n4 defined in the formula (I) and the formula (II)), (2) the recording material according to (1), wherein the formula (I) is the following formula (IV):

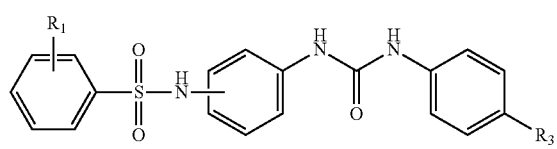

(IV)

(wherein $R_1$ and $R_3$ represent the same as $R_1$ and $R_3$ defined in the formula (I)), (3) the recording material according to (1) or (2), wherein the formula (I) is the following formula (V):

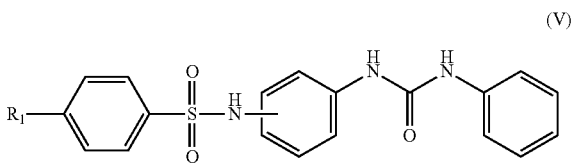

(V)

(wherein $R_1$ represents the same as $R_1$ defined in the formula (I)), and (4) a recording sheet having a recording material layer formed from the recording material according to any one of (1) to (3) on a support.

Besides, the present invention relates to:

(5) a method for using, as a color developing agent, at least one compound selected from the group consisting of:

a compound represented by the following formula (I):

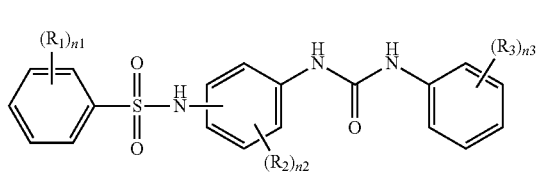

(I)

(wherein $R_1$ to $R_3$ represent the same as $R_1$ to $R_3$ defined in the above, and n1 and n3 represent the same as n1 and n3 defined in the above);

a compound represented by the following formula (II):

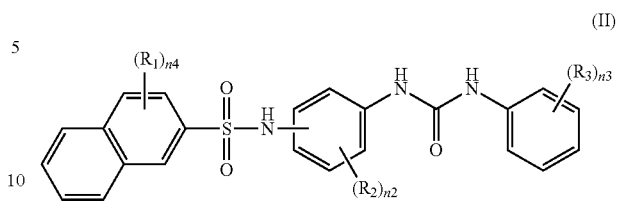

(II)

(wherein $R_1$ to $R_3$ represent the same as $R_1$ to $R_3$ defined in the above, and n2, n3 and n4 represent the same as n2, n3 and n4 defined in the above); and a compound represented by the following formula (III):

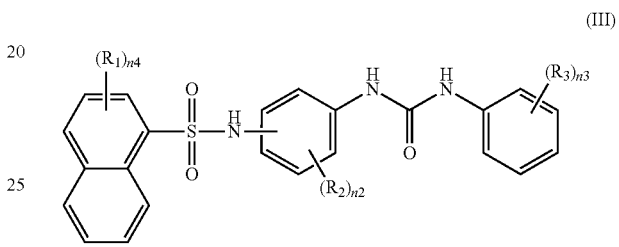

(III)

(wherein $R_1$ to $R_3$ represent the same as $R_1$ to $R_3$ defined in the above, and n2, n3 and n4 represent the same as n2, n3 and n4 defined in the above).

Furthermore, the present invention relates to:

(6) a benzenesulfonamide compound, which is at least one compound selected from the group consisting of:

a compound represented by the following formula (I):

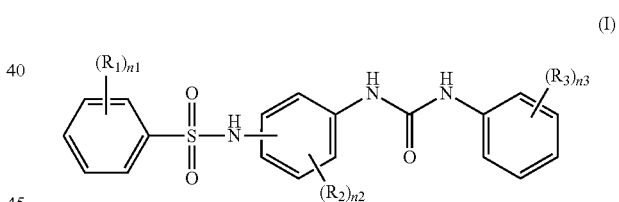

(I)

(wherein $R_1$ to $R_3$ and n1 to n3 represent the same as $R_1$ to $R_3$ and n1 to n3 defined in the above, with the proviso that a case where $R_2$ and $R_3$ each represent a hydrogen atom, and $R_1$ represents any of a hydrogen atom, a p-methyl group, a m-methyl group and a p-chloro group is excluded);

a compound represented by the following formula (II):

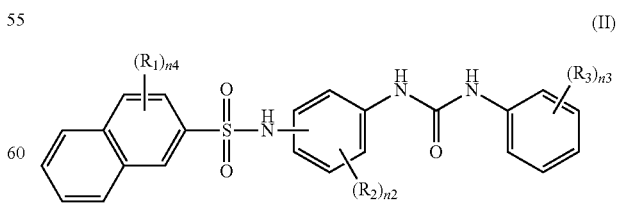

(II)

(wherein $R_1$ to $R_3$ represent the same as $R_1$ to $R_3$ defined in the above, n2 and n3 represent the same as n2 and n3 defined in the above, and n4 represents any integer of 1 to 7); and a compound represented by the following formula (III):

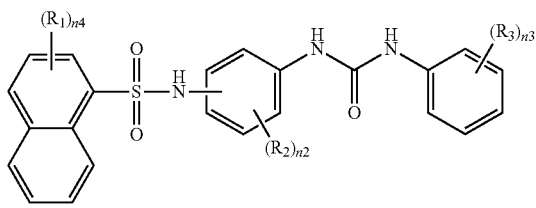

(III)

(wherein $R_1$ to $R_3$ represent the same as $R_1$ to $R_3$ defined in the above, and n2, n3 and n4 represent the same as n2, n3 and n4 defined in the above).

Effect of the Invention

According to the present invention, a recording material or a recording sheet that is not decomposed in water and shows good color developing performance, heat resistance and plasticizer resistance when used together with a color former can be obtained.

Incidentally, the plasticizer resistance has the following significance:

In a supermarket or the like, food, etc. is packaged in a cling film, a label seal of a thermal recording material having a price and the like printed thereon is adhered to the cling film, and some food items thus packaged are stacked in some cases. In such a case, since the film and the label seal are in contact with each other, the thermal material of the label seal can be influenced by a plasticizer or the like contained in the cling film, and hence, the print density can be sometimes lowered. The degree of this influence is numerically expressed as the plasticizer resistance. A method for measuring the plasticizer resistance involves bringing a cling film into close contact with a print once color-developed, and then measuring the situation of the print resulting from peeling off the cling film.

Japanese unexamined Patent Application Publication No. 11-268421 (Patent Document 1) describes a compound having the following structure, which is different from the present compound in a connecting direction of —$NHSO_2$—. When the plasticizer resistance of this compound is measured, the value is low, and the density of a color-developed print portion is lowered. Accordingly, the compound of the present invention good in the plasticizer resistance has been developed.

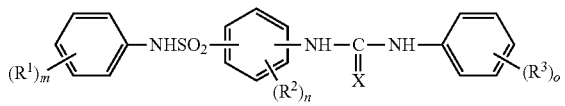

(1)

Mode of Carrying Out the Invention (Non-phenol compounds represented by formulas (I) to (III))

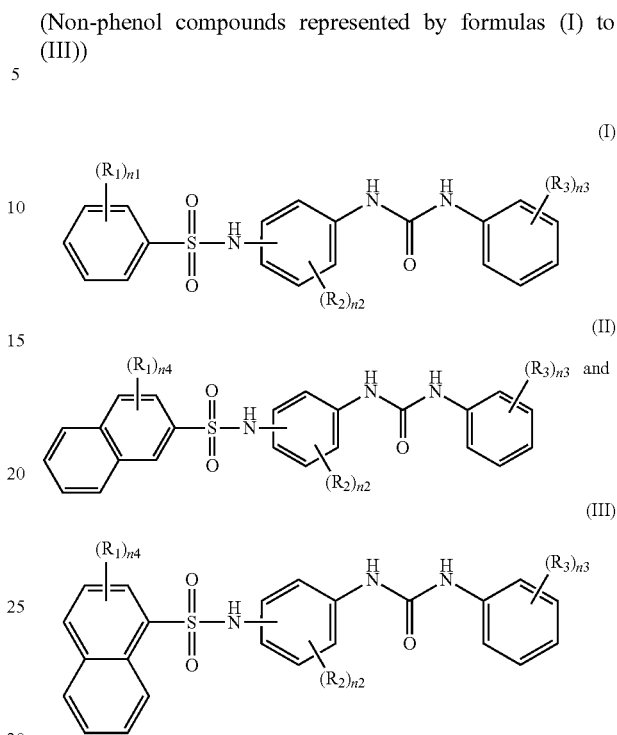

Non-phenol compounds represented by the formulas (I) to (III) are described below.

In the formulas (I), (II) and (III), examples of $R_1$ to $R_3$ include:

a hydrogen atom;

a halogen atom such as a fluorine atom, a chlorine atom, a bromine atom or an iodine atom;

a nitro group;

a straight, branched or cyclic $C_1$-$C_6$ alkyl group such as methyl, ethyl, propyl, isopropyl, butyl, isobutyl, sec-butyl, t-butyl, pentyl, isopentyl, neopentyl, hexyl, isohexyl, cyclopropyl, cyclobutyl, 2-methylcyclopropyl, cyclopropylmethyl, cyclopentyl, or cyclohexyl;

a straight, branched or cyclic $C_1$-$C_6$ alkoxy group such as methoxy, ethoxy, propoxy, isopropoxy, butoxy, isobutoxy, sec-butoxy, t-butoxy, pentyloxy, isopentyloxy, hexyloxy, cyclopropoxy, cyclobutoxy, 2-methylcyclopropoxy, cyclopropylmethoxy, cyclopentyloxy, or cyclohexyloxy;

a $C_2$-$C_6$ alkenyl group such as a vinyl group, an allyl group, an isopropenyl group, a 1-propenyl group, a 2-propenyl group, a 1-butenyl group, a 2-butenyl group, a 3-butenyl group, a 1,3-butanedienyl group, or a 2-methyl-2-propenyl group;

a $C_1$-$C_6$ fluoroalkyl group such as a trifluoromethyl group, a perfluoroethyl group, a perfluoropropyl group, a perfluorobutyl group, a perfluorohexyl group, or a perfluorocyclohexyl group;

a $N(R_4)_2$ group (wherein $R_4$ represents a hydrogen atom, a phenyl group, a benzyl group or a $C_1$-$C_6$ alkyl group);

$NHCOR_5$ (wherein $R_5$ represents a $C_1$-$C_6$ alkyl group);

an optionally substituted phenyl group; and an optionally substituted benzyl group.

Preferably, $R_1$ to $R_3$ each represent a hydrogen atom or a straight $C_1$-$C_6$ alkyl group, and more preferably, $R_1$ represents a hydrogen atom or a methyl group, and $R_2$ and $R_3$ each represent a hydrogen atom.

Examples of the $C_1$-$C_6$ alkyl group used as $R_4$ or $R_5$ above include the same as the specific examples of the $C_1$-$C_6$ alkyl group used as $R_1$ above.

Here, examples of the substituent with which a group is "optionally substituted" include:

a hydroxy group;

a halogen atom such as a fluorine atom, a chlorine atom, a bromine atom, or an iodine atom;

a $C_1$-$C_6$ alkyl group such as a methyl group, an ethyl group, a n-propyl group, an isopropyl group, a n-butyl group, a sec-butyl group, a t-butyl group, a n-pentyl group, an isopentyl group, a neopentyl group, a t-pentyl group, a n-hexyl group, an isohexyl group, a 1-methyl pentyl group, or a 2-methyl pentyl group; and a $C_1$-$C_6$ alkoxy group such as a methoxy group, an ethoxy group, a n-propoxy group, an isopropoxy group, a n-butoxy group, a sec-butoxy group, or a t-butoxy group.

Besides, it should be noted that benzenesulfonamide compounds, that is, a compound represented by the following formula (I):

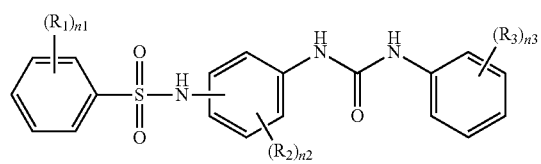

(I)

(wherein $R_1$ to $R_3$ and n1 to n3 represent the same as $R_1$ to $R_3$ and n1 to n3 defined in the above, with the proviso that a case where $R_2$ and $R_3$ each represent a hydrogen atom, and $R_1$ represents any of a hydrogen atom, a p-methyl group, a m-methyl group and a p-chloro group is excluded), a compound represented by the following formula (II):

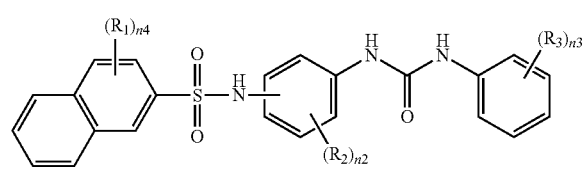

(II)

(wherein $R_1$ to $R_3$ represent the same as $R_1$ to $R_3$ defined in the above, n2 and n3 represent the same as n2 and n3 defined in the above, and n4 represents any integer of 1 to 7), and a compound represented by the following formula (III):

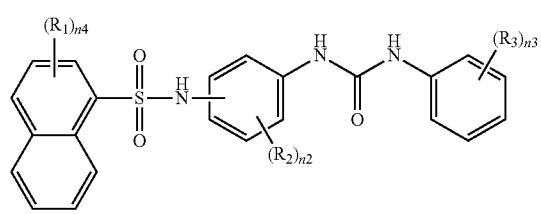

(III)

(wherein $R_1$ to $R_3$ represent the same as $R_1$ to $R_3$ defined in the above, and n2, n3 and n4 represent the same as n2, n3 and n4 defined in the above), are compounds that can be produced for the first time by the present invention.

Representative examples of the compounds represented by the formulas (I) to (III) include 4-methyl-N-(2-(3-phenylureido)phenyl)benzenesulfonamide and N-(2-(3-phenylureido)phenyl)benzenesulfonamide.

(Method for Producing Non-Phenol Compounds Represented by Formulas (I) to (III))

The non-phenol compounds represented by the formulas (I) to (III) can be produced by any method as long as the compounds can be produced, and as an example, a method for producing a compound represented by the following formula (VI) belonging to the compound represented by the formula (I) is described below.

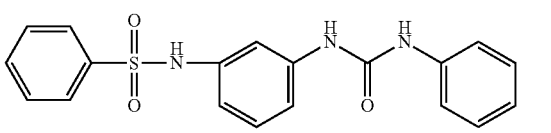

(VI)

(First Addition Reaction)

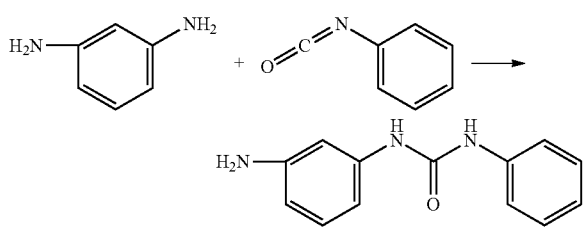

To a solution of m-phenylenediamine in ethyl acetate, phenyl isocyanate is added dropwise, and a reaction is performed at room temperature for 0.5 to 6 hours. After the reaction, deposited crystals are filtered off, and thus, 1-(3-aminophenyl)-3-phenylurea can be obtained as white crystals.

(Second Addition Reaction)

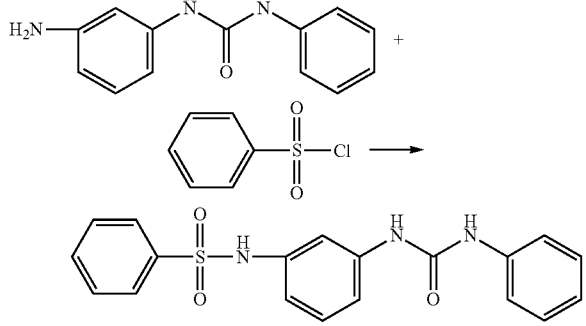

To ethyl acetate, the 1-(3-aminophenyl)-3-phenylurea obtained by the above-described first addition reaction and triethylamine are added, and benzenesulfonyl chloride is added thereto in small aliquots, and thereafter, the resultant is refluxed for 0.5 to 6 hours. After the completion of the reaction, a general post-treatment is performed, the resultant is crystallized with ethanol, and thus, white crystals can be obtained.

If benzenesulfonyl chloride, naphthalenesulfonyl chloride or the like having the $R_1$ group is used instead of the above-described benzenesulfonyl chloride, the $R_1$ group can be easily introduced, or a phenyl group can be easily substituted by a naphthyl group. Alternatively, if phenylenediamine having the $R_2$ group is used instead of the above-described m-phenylenediamine, the $R_2$ group can be easily introduced. Besides, if phenyl isocyanate having the $R_3$ group is used instead of the above-described phenyl isocyanate, the $R_3$ group can be easily introduced.

The triethylamine can be replaced with another basic compound. For example, pyridine, sodium hydroxide, potassium hydroxide, sodium carbonate, sodium bicarbonate, potassium carbonate, or potassium bicarbonate can be used.

Besides, the ethyl acetate can be replaced with a solvent that can be usually used in an organic reaction. For example, toluene, xylene, hexane, acetone, methyl ethyl ketone, methyl isobutyl ketone, THF, acetonitrile, monochlorobenzene, dichlorobenzene, dichloromethane, or chloroform can be used.

The first addition reaction can be performed at room temperature, but can be also performed by heating or cooling, and the temperature can be changed in accordance with the characteristics of the raw materials. Besides, with respect to the temperature of the second addition reaction, the reaction can be performed as a reflux reaction in an ethyl acetate solvent, but it needs not be the reflux reaction, and the temperature can be changed in accordance with the characteristics of the raw materials.

Instead of the ethanol, a usually usable organic solvent can be used as a solvent for the recrystallization. For example, methanol, isopropanol, toluene, acetonitrile, ethyl acetate, hexane, acetone, methyl ethyl ketone, methyl isobutyl ketone, diethyl ether, monochlorobenzene, dichlorobenzene, dichloromethane, or chloroform can be used. For the recrystallization, crystals can be deposited by cooling after dissolved by heating, can be deposited by adding/dropwise adding a poor solvent after dissolved in a good solvent, can be deposited by distilling off a solvent, or can be deposited by adding/dropwise adding another solvent after distilling off the solvent.

A factor that enables the compounds of the present invention to be easily obtained in high yield is that phenylenediamine is used as a raw material of the first addition reaction. Since the phenylenediamine is inexpensively available, it is industrially advantageous. Besides, the phenylenediamine and phenyl isocyanate are easily reacted with each other to produce aminophenyl-phenylurea, but this compound is difficult to dissolve in a solvent and is deposited as crystals, and a byproduct resulting from the reaction of two phenyl isocyanates is difficult to be produced. Furthermore, the product of the first addition reaction can be obtained in high purity merely by filtration. As a result, the product of the second addition reaction can be obtained in high purity and high yield.

(Another Method for First Addition Reaction)

The first addition reaction can be performed by another method as follows:

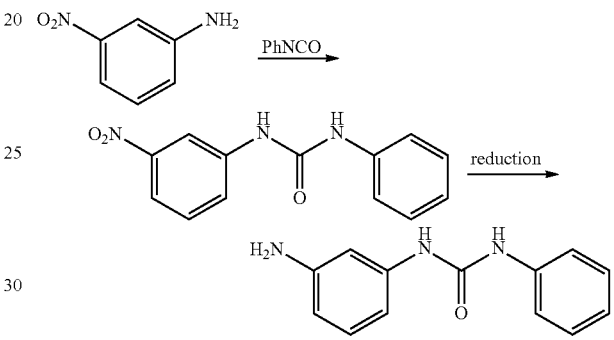

The non-phenol compounds of the present invention can be identified in their structure by measuring $^1$H-NMR, $^{13}$C-NMR, IR, MS or the like by using a known measuring apparatus. Besides, the purity can be measured by using a measuring apparatus for liquid chromatography (HPLC), thermal analysis (DSC) or the like.

Furthermore, examples of a compound that can be thus synthesized are shown in Table 1.

TABLE 1

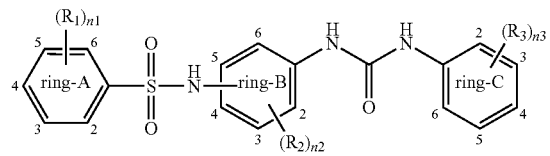

(Numbers shown around ring-A to ring-C in the formula above indicate positions on the rings. Similarly, numbers shown in the columns of ring-A to ring-C in the following tables indicate the positions on the rings.)

| COMPOUND | ring-A $(R_1)_{n1}$ | | | | | ring-B $(R_2)_{n2}$ and $NHSO_2$-ringA$SO_2$-ringA | | | | | ring-C $(R_3)_{n3}$ | | | | | EXAMPLE | MELTING POINT (° C.) |
|---|---|---|---|---|---|---|---|---|---|---|---|---|---|---|---|---|---|
| No | 2 | 3 | 4 | 5 | 6 | 2 | 3 | 4 | 5 | 6 | 2 | 3 | 4 | 5 | 6 | | |
| 1 | H | H | H | H | H | NHSO$_2$-ringA | H | H | H | H | H | H | H | H | H | 4 | 155-157 |
| 2 | CH$_3$ | H | H | H | H | NHSO$_2$-ringA | H | H | H | H | H | H | H | H | H | 3 | 147-150 |
| 3 | H | CH$_3$ | H | H | H | NHSO$_2$-ringA | H | H | H | H | H | H | H | H | H | 2 | 161-164 |
| 4 | H | H | CH$_3$ | H | H | NHSO$_2$-ringA | H | H | H | H | H | H | H | H | H | 1 | 171-173 |
| 5 | H | H | NHAc | H | H | NHSO$_2$-ringA | H | H | H | H | H | H | H | H | H | 26 | 196-200 |
| 6 | H | H | Et | H | H | NHSO$_2$-ringA | H | H | H | H | H | H | H | H | H | 27 | 86-89 |

TABLE 1-continued

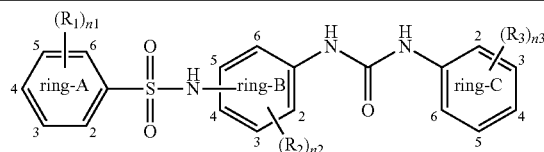

(Numbers shown around ring-A to ring-C in the formula above indicate positions on the rings. Similarly, numbers shown in the columns of ring-A to ring-C in the following tables indicate the positions on the rings.)

| COM-POUND No | ring-A $(R_1)_{n1}$ | | | | | ring-B $(R_2)_{n2}$ and NHSO$_2$-ringASO$_2$-ringA | | | | | ring-C $(R_3)_{n3}$ | | | | | EX-AM-PLE | MELT-ING POINT (° C.) |
|---|---|---|---|---|---|---|---|---|---|---|---|---|---|---|---|---|---|
| | 2 | 3 | 4 | 5 | 6 | 2 | 3 | 4 | 5 | 6 | 2 | 3 | 4 | 5 | 6 | | |
| 7 | H | H | OMe | H | H | NHSO$_2$-ringA | H | H | H | H | H | H | H | H | H | 28 | 164-166 |
| 8 | Cl | H | H | H | H | NHSO$_2$-ringA | H | H | H | H | H | H | H | H | H | | |
| 9 | H | Cl | H | H | H | NHSO$_2$-ringA | H | H | H | H | H | H | H | H | H | | |
| 10 | H | H | Cl | H | H | NHSO$_2$-ringA | H | H | H | H | H | H | H | H | H | 5 | 163-165 |
| 11 | H | H | H | H | H | H | NHSO$_2$-ringA | H | H | H | H | H | H | H | H | 9 | 195-197 |
| 12 | CH$_3$ | H | H | H | H | H | NHSO$_2$-ringA | H | H | H | H | H | H | H | H | 8 | 197-199 |
| 13 | H | CH$_3$ | H | H | H | H | NHSO$_2$-ringA | H | H | H | H | H | H | H | H | 7 | 190-191 |
| 14 | H | H | CH$_3$ | H | H | H | NHSO$_2$-ringA | H | H | H | H | H | H | H | H | 6 | 196-198 |
| 15 | Cl | H | H | H | H | H | NHSO$_2$-ringA | H | H | H | H | H | H | H | H | | |
| 16 | H | Cl | H | H | H | H | NHSO$_2$-ringA | H | H | H | H | H | H | H | H | | |
| 17 | H | H | Cl | H | H | H | NHSO$_2$-ringA | H | H | H | H | H | H | H | H | | |
| 18 | H | H | H | H | H | H | H | NHSO$_2$-ringA | H | H | H | H | H | H | H | 13 | 180-182 |
| 19 | CH$_3$ | H | H | H | H | H | H | NHSO$_2$-ringA | H | H | H | H | H | H | H | 12 | 169-172 |
| 20 | H | CH$_3$ | H | H | H | H | H | NHSO$_2$-ringA | H | H | H | H | H | H | H | 11 | 183-185 |
| 21 | H | H | CH$_3$ | H | H | H | H | NHSO$_2$-ringA | H | H | H | H | H | H | H | 10 | 204-206 |
| 22 | Cl | H | H | H | H | H | H | NHSO$_2$-ringA | H | H | H | H | H | H | H | | |
| 23 | H | Cl | H | H | H | H | H | NHSO$_2$-ringA | H | H | H | H | H | H | H | | |
| 24 | H | H | Cl | H | H | H | H | NHSO$_2$-ringA | H | H | H | H | H | H | H | | |
| 25 | H | H | H | H | H | H | NHSO$_2$-ringA | CH$_3$ | H | H | H | H | H | H | H | | |
| 26 | CH$_3$ | H | H | H | H | H | NHSO$_2$-ringA | CH$_3$ | H | H | H | H | H | H | H | | |
| 27 | H | CH$_3$ | H | H | H | H | NHSO$_2$-ringA | CH$_3$ | H | H | H | H | H | H | H | | |
| 28 | H | H | CH$_3$ | H | H | H | NHSO$_2$-ringA | CH$_3$ | H | H | H | H | H | H | H | 15 | 206-207 |
| 29 | Cl | H | H | H | H | H | NHSO$_2$-ringA | CH$_3$ | H | H | H | H | H | H | H | | |
| 30 | H | Cl | H | H | H | H | NHSO$_2$-ringA | CH$_3$ | H | H | H | H | H | H | H | | |
| 31 | H | H | Cl | H | H | H | NHSO$_2$-ringA | CH$_3$ | H | H | H | H | H | H | H | 14 | 173-175 |
| 32 | H | H | H | H | H | H | NHSO$_2$-ringA | H | H | CH$_3$ | H | H | H | H | H | | |
| 33 | CH$_3$ | H | H | H | H | H | NHSO$_2$-ringA | H | H | CH$_3$ | H | H | H | H | H | | |
| 34 | H | CH$_3$ | H | H | H | H | NHSO$_2$-ringA | H | H | CH$_3$ | H | H | H | H | H | | |
| 35 | H | H | CH$_3$ | H | H | H | NHSO$_2$-ringA | H | H | CH$_3$ | H | H | H | H | H | | |
| 36 | Cl | H | H | H | H | H | NHSO$_2$-ringA | H | H | CH$_3$ | H | H | H | H | H | | |
| 37 | H | Cl | H | H | H | H | NHSO$_2$-ringA | H | H | CH$_3$ | H | H | H | H | H | | |
| 38 | H | H | Cl | H | H | H | NHSO$_2$-ringA | H | H | CH$_3$ | H | H | H | H | H | | |

TABLE 1-continued

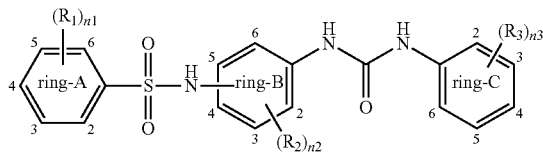

(Numbers shown around ring-A to ring-C in the formula above indicate positions on the rings. Similarly, numbers shown in the columns of ring-A to ring-C in the following tables indicate the positions on the rings.)

| COMPOUND | ring-A $(R_1)_{n1}$ | | | | | ring-B $(R_2)_{n2}$ and $NHSO_2$-ringASO$_2$-ringA | | | | | ring-C $(R_3)_{n3}$ | | | | | EXAMPLE | MELTING POINT |
|---|---|---|---|---|---|---|---|---|---|---|---|---|---|---|---|---|---|
| No | 2 | 3 | 4 | 5 | 6 | 2 | 3 | 4 | 5 | 6 | 2 | 3 | 4 | 5 | 6 | PLE | (° C.) |
| 39 | H | H | H | H | H | NHSO$_2$-ringA | H | H | H | H | CH$_3$ | H | H | H | H | | |
| 40 | CH$_3$ | H | H | H | H | NHSO$_2$-ringA | H | H | H | H | CH$_3$ | H | H | H | H | | |
| 41 | H | CH$_3$ | H | H | H | NHSO$_2$-ringA | H | H | H | H | CH$_3$ | H | H | H | H | | |
| 42 | H | H | CH$_3$ | H | H | NHSO$_2$-ringA | H | H | H | H | CH$_3$ | H | H | H | H | | |
| 43 | Cl | H | H | H | H | NHSO$_2$-ringA | H | H | H | H | CH$_3$ | H | H | H | H | | |
| 44 | H | Cl | H | H | H | NHSO$_2$-ringA | H | H | H | H | CH$_3$ | H | H | H | H | | |
| 45 | H | H | Cl | H | H | NHSO$_2$-ringA | H | H | H | H | CH$_3$ | H | H | H | H | | |
| 46 | H | H | H | H | H | H | NHSO$_2$-ringA | H | H | H | CH$_3$ | H | H | H | H | | |
| 47 | CH$_3$ | H | H | H | H | H | NHSO$_2$-ringA | H | H | H | CH$_3$ | H | H | H | H | | |
| 48 | H | CH$_3$ | H | H | H | H | NHSO$_2$-ringA | H | H | H | CH$_3$ | H | H | H | H | | |
| 49 | H | H | CH$_3$ | H | H | H | NHSO$_2$-ringA | H | H | H | CH$_3$ | H | H | H | H | | |
| 50 | Cl | H | H | H | H | H | NHSO$_2$-ringA | H | H | H | CH$_3$ | H | H | H | H | | |
| 51 | H | Cl | H | H | H | H | NHSO$_2$-ringA | H | H | H | CH$_3$ | H | H | H | H | | |
| 52 | H | H | Cl | H | H | H | NHSO$_2$-ringA | H | H | H | CH$_3$ | H | H | H | H | | |
| 53 | H | H | H | H | H | H | H | NHSO$_2$-ringA | H | H | CH$_3$ | H | H | H | H | | |
| 54 | CH$_3$ | H | H | H | H | H | H | NHSO$_2$-ringA | H | H | CH$_3$ | H | H | H | H | | |
| 55 | H | CH$_3$ | H | H | H | H | H | NHSO$_2$-ringA | H | H | CH$_3$ | H | H | H | H | | |
| 56 | H | H | CH$_3$ | H | H | H | H | NHSO$_2$-ringA | H | H | CH$_3$ | H | H | H | H | | |
| 57 | Cl | H | H | H | H | H | H | NHSO$_2$-ringA | H | H | CH$_3$ | H | H | H | H | | |
| 58 | H | Cl | H | H | H | H | H | NHSO$_2$-ringA | H | H | CH$_3$ | H | H | H | H | | |
| 59 | H | H | Cl | H | H | H | H | NHSO$_2$-ringA | H | H | CH$_3$ | H | H | H | H | | |
| 60 | H | H | H | H | H | NHSO$_2$-ringA | CH$_3$ | H | H | H | CH$_3$ | H | H | H | H | | |
| 61 | CH$_3$ | H | H | H | H | NHSO$_2$-ringA | CH$_3$ | H | H | H | CH$_3$ | H | H | H | H | | |
| 62 | H | CH$_3$ | H | H | H | NHSO$_2$-ringA | CH$_3$ | H | H | H | CH$_3$ | H | H | H | H | | |
| 63 | H | H | CH$_3$ | H | H | NHSO$_2$-ringA | CH$_3$ | H | H | H | CH$_3$ | H | H | H | H | | |
| 64 | Cl | H | H | H | H | NHSO$_2$-ringA | CH$_3$ | H | H | H | CH$_3$ | H | H | H | H | | |
| 65 | H | Cl | H | H | H | NHSO$_2$-ringA | CH$_3$ | H | H | H | CH$_3$ | H | H | H | H | | |
| 66 | H | H | Cl | H | H | NHSO$_2$-ringA | CH$_3$ | H | H | H | CH$_3$ | H | H | H | H | | |
| 67 | H | H | H | H | H | NHSO$_2$-ringA | H | H | CH$_3$ | CH$_3$ | H | H | H | H | H | | |
| 68 | CH$_3$ | H | H | H | H | NHSO$_2$-ringA | H | H | CH$_3$ | CH$_3$ | H | H | H | H | H | | |
| 69 | H | CH$_3$ | H | H | H | NHSO$_2$-ringA | H | H | CH$_3$ | CH$_3$ | H | H | H | H | H | | |
| 70 | H | H | CH$_3$ | H | H | NHSO$_2$-ringA | H | H | CH$_3$ | CH$_3$ | H | H | H | H | H | | |

TABLE 1-continued

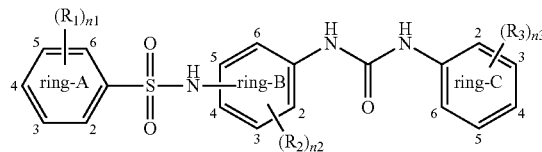

(Numbers shown around ring-A to ring-C in the formula above indicate positions on the rings. Similarly, numbers shown in the columns of ring-A to ring-C in the following tables indicate the positions on the rings.)

| COMPOUND No | ring-A $(R_1)_{n1}$ | | | | | ring-B $(R_2)_{n2}$ and $NHSO_2$-ringASO$_2$-ringA | | | | | ring-C $(R_3)_{n3}$ | | | | | EXAMPLE | MELTING POINT (° C.) |
|---|---|---|---|---|---|---|---|---|---|---|---|---|---|---|---|---|---|
| | 2 | 3 | 4 | 5 | 6 | 2 | 3 | 4 | 5 | 6 | 2 | 3 | 4 | 5 | 6 | | |
| 71 | Cl | H | H | H | H | H | NHSO$_2$-ringA | H | H | CH$_3$ | CH$_3$ | H | H | H | H | | |
| 72 | H | Cl | H | H | H | H | NHSO$_2$-ringA | H | H | CH$_3$ | CH$_3$ | H | H | H | H | | |
| 73 | H | H | Cl | H | H | H | NHSO$_2$-ringA | H | H | CH$_3$ | CH$_3$ | H | H | H | H | | |
| 74 | H | H | H | H | H | NHSO$_2$-ringA | H | H | H | H | H | CH$_3$ | H | H | H | | |
| 75 | CH$_3$ | H | H | H | H | NHSO$_2$-ringA | H | H | H | H | H | CH$_3$ | H | H | H | | |
| 76 | H | CH$_3$ | H | H | H | NHSO$_2$-ringA | H | H | H | H | H | CH$_3$ | H | H | H | | |
| 77 | H | H | CH$_3$ | H | H | NHSO$_2$-ringA | H | H | H | H | H | CH$_3$ | H | H | H | | |
| 78 | Cl | H | H | H | H | NHSO$_2$-ringA | H | H | H | H | H | CH$_3$ | H | H | H | | |
| 79 | H | Cl | H | H | H | NHSO$_2$-ringA | H | H | H | H | H | CH$_3$ | H | H | H | | |
| 80 | H | H | Cl | H | H | NHSO$_2$-ringA | H | H | H | H | H | CH$_3$ | H | H | H | | |
| 81 | H | H | H | H | H | H | NHSO$_2$-ringA | H | H | H | H | CH$_3$ | H | H | H | | |
| 82 | CH$_3$ | H | H | H | H | H | NHSO$_2$-ringA | H | H | H | H | CH$_3$ | H | H | H | | |
| 83 | H | CH$_3$ | H | H | H | H | NHSO$_2$-ringA | H | H | H | H | CH$_3$ | H | H | H | | |
| 84 | H | H | CH$_3$ | H | H | H | NHSO$_2$-ringA | H | H | H | H | CH$_3$ | H | H | H | | |
| 85 | Cl | H | H | H | H | H | NHSO$_2$-ringA | H | H | H | H | CH$_3$ | H | H | H | | |
| 86 | H | Cl | H | H | H | H | NHSO$_2$-ringA | H | H | H | H | CH$_3$ | H | H | H | | |
| 87 | H | H | Cl | H | H | H | NHSO$_2$-ringA | H | H | H | H | CH$_3$ | H | H | H | | |
| 88 | H | H | H | H | H | H | H | NHSO$_2$-ringA | H | H | H | CH$_3$ | H | H | H | | |
| 89 | CH$_3$ | H | H | H | H | H | H | NHSO$_2$-ringA | H | H | H | CH$_3$ | H | H | H | | |
| 90 | H | CH$_3$ | H | H | H | H | H | NHSO$_2$-ringA | H | H | H | CH$_3$ | H | H | H | | |
| 91 | H | H | CH$_3$ | H | H | H | H | NHSO$_2$-ringA | H | H | H | CH$_3$ | H | H | H | | |
| 92 | Cl | H | H | H | H | H | H | NHSO$_2$-ringA | H | H | H | CH$_3$ | H | H | H | | |
| 93 | H | Cl | H | H | H | H | H | NHSO$_2$-ringA | H | H | H | CH$_3$ | H | H | H | | |
| 94 | H | H | Cl | H | H | H | H | NHSO$_2$-ringA | H | H | H | CH$_3$ | H | H | H | | |
| 95 | H | H | H | H | H | NHSO$_2$-ringA | CH$_3$ | H | H | H | H | CH$_3$ | H | H | H | | |
| 96 | CH$_3$ | H | H | H | H | NHSO$_2$-ringA | CH$_3$ | H | H | H | H | CH$_3$ | H | H | H | | |
| 97 | H | CH$_3$ | H | H | H | NHSO$_2$-ringA | CH$_3$ | H | H | H | H | CH$_3$ | H | H | H | | |
| 98 | H | H | CH$_3$ | H | H | NHSO$_2$-ringA | CH$_3$ | H | H | H | H | CH$_3$ | H | H | H | | |
| 99 | Cl | H | H | H | H | NHSO$_2$-ringA | CH$_3$ | H | H | H | H | CH$_3$ | H | H | H | | |
| 100 | H | Cl | H | H | H | NHSO$_2$-ringA | CH$_3$ | H | H | H | H | CH$_3$ | H | H | H | | |
| 101 | H | H | Cl | H | H | NHSO$_2$-ringA | CH$_3$ | H | H | H | H | CH$_3$ | H | H | H | | |
| 102 | H | H | H | H | H | H | NHSO$_2$-ringA | H | H | CH$_3$ | H | CH$_3$ | H | H | H | | |

TABLE 1-continued

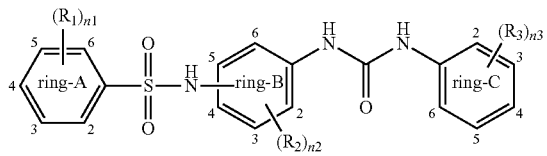

(Numbers shown around ring-A to ring-C in the formula above indicate positions on the rings. Similarly, numbers shown in the columns of ring-A to ring-C in the following tables indicate the positions on the rings.)

| COMPOUND No | ring-A $(R_1)_{n1}$ | | | | | ring-B $(R_2)_{n2}$ and $NHSO_2$-ringASO$_2$-ringA | | | | | ring-C $(R_3)_{n3}$ | | | | | EXAMPLE | MELTING POINT (°C.) |
|---|---|---|---|---|---|---|---|---|---|---|---|---|---|---|---|---|---|
| | 2 | 3 | 4 | 5 | 6 | 2 | 3 | 4 | 5 | 6 | 2 | 3 | 4 | 5 | 6 | | |
| 103 | CH$_3$ | H | H | H | H | H | NHSO$_2$-ringA | H | H | CH$_3$ | H | CH$_3$ | H | H | H | | |
| 104 | H | CH$_3$ | H | H | H | H | NHSO$_2$-ringA | H | H | CH$_3$ | H | CH$_3$ | H | H | H | | |
| 105 | H | H | CH$_3$ | H | H | H | NHSO$_2$-ringA | H | H | CH$_3$ | H | CH$_3$ | H | H | H | | |
| 106 | Cl | H | H | H | H | H | NHSO$_2$-ringA | H | H | CH$_3$ | H | CH$_3$ | H | H | H | | |
| 107 | H | Cl | H | H | H | H | NHSO$_2$-ringA | H | H | CH$_3$ | H | CH$_3$ | H | H | H | | |
| 108 | H | H | Cl | H | H | H | NHSO$_2$-ringA | H | H | CH$_3$ | H | CH$_3$ | H | H | H | | |
| 109 | H | H | H | H | H | NHSO$_2$-ringA | H | H | H | H | H | H | CH$_3$ | H | H | | |
| 110 | CH$_3$ | H | H | H | H | NHSO$_2$-ringA | H | H | H | H | H | H | CH$_3$ | H | H | | |
| 111 | H | CH$_3$ | H | H | H | NHSO$_2$-ringA | H | H | H | H | H | H | CH$_3$ | H | H | | |
| 112 | H | H | CH$_3$ | H | H | NHSO$_2$-ringA | H | H | H | H | H | H | CH$_3$ | H | H | | |
| 113 | Cl | H | H | H | H | NHSO$_2$-ringA | H | H | H | H | H | H | CH$_3$ | H | H | | |
| 114 | H | Cl | H | H | H | NHSO$_2$-ringA | H | H | H | H | H | H | CH$_3$ | H | H | | |
| 115 | H | H | Cl | H | H | NHSO$_2$-ringA | H | H | H | H | H | H | CH$_3$ | H | H | | |
| 116 | H | H | H | H | H | H | NHSO$_2$-ringA | H | H | H | H | H | CH$_3$ | H | H | | |
| 117 | CH$_3$ | H | H | H | H | H | NHSO$_2$-ringA | H | H | H | H | H | CH$_3$ | H | H | | |
| 118 | H | CH$_3$ | H | H | H | H | NHSO$_2$-ringA | H | H | H | H | H | CH$_3$ | H | H | | |
| 119 | H | H | CH$_3$ | H | H | H | NHSO$_2$-ringA | H | H | H | H | H | CH$_3$ | H | H | | |
| 120 | Cl | H | H | H | H | H | NHSO$_2$-ringA | H | H | H | H | H | CH$_3$ | H | H | | |
| 121 | H | Cl | H | H | H | H | NHSO$_2$-ringA | H | H | H | H | H | CH$_3$ | H | H | | |
| 122 | H | H | Cl | H | H | H | NHSO$_2$-ringA | H | H | H | H | H | CH$_3$ | H | H | | |
| 123 | H | H | H | H | H | H | H | NHSO$_2$-ringA | H | H | H | H | CH$_3$ | H | H | | |
| 124 | CH$_3$ | H | H | H | H | H | H | NHSO$_2$-ringA | H | H | H | H | CH$_3$ | H | H | | |
| 125 | H | CH$_3$ | H | H | H | H | H | NHSO$_2$-ringA | H | H | H | H | CH$_3$ | H | H | | |
| 126 | H | H | CH$_3$ | H | H | H | H | NHSO$_2$-ringA | H | H | H | H | CH$_3$ | H | H | | |
| 127 | Cl | H | H | H | H | H | H | NHSO$_2$-ringA | H | H | H | H | CH$_3$ | H | H | | |
| 128 | H | Cl | H | H | H | H | H | NHSO$_2$-ringA | H | H | H | H | CH$_3$ | H | H | | |
| 129 | H | H | Cl | H | H | H | H | NHSO$_2$-ringA | H | H | H | H | CH$_3$ | H | H | | |
| 130 | H | H | H | H | H | NHSO$_2$-ringA | CH$_3$ | H | H | H | H | H | CH$_3$ | H | H | | |
| 131 | CH$_3$ | H | H | H | H | NHSO$_2$-ringA | CH$_3$ | H | H | H | H | H | CH$_3$ | H | H | | |
| 132 | H | CH$_3$ | H | H | H | NHSO$_2$-ringA | CH$_3$ | H | H | H | H | H | CH$_3$ | H | H | | |
| 133 | H | H | CH$_3$ | H | H | NHSO$_2$-ringA | CH$_3$ | H | H | H | H | H | CH$_3$ | H | H | | |
| 134 | Cl | H | H | H | H | NHSO$_2$-ringA | CH$_3$ | H | H | H | H | H | CH$_3$ | H | H | | |

TABLE 1-continued

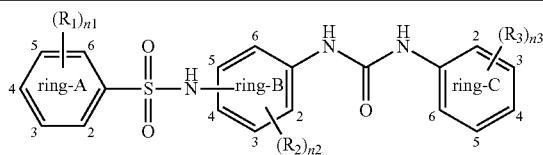

(Numbers shown around ring-A to ring-C in the formula above indicate positions on the rings. Similarly, numbers shown in the columns of ring-A to ring-C in the following tables indicate the positions on the rings.)

| COMPOUND No | ring-A (R₁)ₙ₁ | | | | | ring-B (R₂)ₙ₂ and NHSO₂-ringASO₂-ringA | | | | | ring-C (R₃)ₙ₃ | | | | | EXAMPLE | MELTING POINT (°C.) |
|---|---|---|---|---|---|---|---|---|---|---|---|---|---|---|---|---|---|
| | 2 | 3 | 4 | 5 | 6 | 2 | 3 | 4 | 5 | 6 | 2 | 3 | 4 | 5 | 6 | | |
| 135 | H | Cl | H | H | H | H | NHSO₂-ringA | CH₃ | H | H | H | CH₃ | H | H | | |
| 136 | H | H | Cl | H | H | H | NHSO₂-ringA | CH₃ | H | H | H | CH₃ | H | H | | |
| 137 | H | H | H | H | H | H | NHSO₂-ringA | H | H | CH₃ | H | CH₃ | H | H | | |
| 138 | CH₃ | H | H | H | H | H | NHSO₂-ringA | H | H | CH₃ | H | CH₃ | H | H | | |
| 139 | H | CH₃ | H | H | H | H | NHSO₂-ringA | H | H | CH₃ | H | CH₃ | H | H | | |
| 140 | H | H | CH₃ | H | H | H | NHSO₂-ringA | H | H | CH₃ | H | CH₃ | H | H | | |
| 141 | Cl | H | H | H | H | H | NHSO₂-ringA | H | H | CH₃ | H | CH₃ | H | H | | |
| 142 | H | Cl | H | H | H | H | NHSO₂-ringA | H | H | CH₃ | H | CH₃ | H | H | | |
| 143 | H | H | Cl | H | H | H | NHSO₂-ringA | H | H | CH₃ | H | CH₃ | H | H | | |
| 144 | H | H | H | H | H | NHSO₂-ringA | H | H | H | H | Cl | H | H | H | | |
| 145 | CH₃ | H | H | H | H | NHSO₂-ringA | H | H | H | H | Cl | H | H | H | | |
| 146 | H | CH₃ | H | H | H | NHSO₂-ringA | H | H | H | H | Cl | H | H | H | | |
| 147 | H | H | CH₃ | H | H | NHSO₂-ringA | H | H | H | H | Cl | H | H | H | | |
| 148 | Cl | H | H | H | H | NHSO₂-ringA | H | H | H | H | Cl | H | H | H | | |
| 149 | H | Cl | H | H | H | NHSO₂-ringA | H | H | H | H | Cl | H | H | H | | |
| 150 | H | H | Cl | H | H | NHSO₂-ringA | H | H | H | H | Cl | H | H | H | | |
| 151 | H | H | H | H | H | H | NHSO₂-ringA | H | H | H | H | Cl | H | H | | |
| 152 | CH₃ | H | H | H | H | H | NHSO₂-ringA | H | H | H | H | Cl | H | H | | |
| 153 | H | CH₃ | H | H | H | H | NHSO₂-ringA | H | H | H | H | Cl | H | H | | |
| 154 | H | H | CH₃ | H | H | H | NHSO₂-ringA | H | H | H | H | Cl | H | H | | |
| 155 | Cl | H | H | H | H | H | NHSO₂-ringA | H | H | H | H | Cl | H | H | | |
| 156 | H | Cl | H | H | H | H | NHSO₂-ringA | H | H | H | H | Cl | H | H | | |
| 157 | H | H | Cl | H | H | H | NHSO₂-ringA | H | H | H | H | Cl | H | H | | |
| 158 | H | H | H | H | H | H | H | NHSO₂-ringA | H | H | H | Cl | H | H | | |
| 159 | CH₃ | H | H | H | H | H | H | NHSO₂-ringA | H | H | H | Cl | H | H | | |
| 160 | H | CH₃ | H | H | H | H | H | NHSO₂-ringA | H | H | H | Cl | H | H | | |
| 161 | H | H | CH₃ | H | H | H | H | NHSO₂-ringA | H | H | H | Cl | H | H | | |
| 162 | Cl | H | H | H | H | H | H | NHSO₂-ringA | H | H | H | Cl | H | H | | |
| 163 | H | Cl | H | H | H | H | H | NHSO₂-ringA | H | H | H | Cl | H | H | | |
| 164 | H | H | Cl | H | H | H | H | NHSO₂-ringA | H | H | H | Cl | H | H | | |
| 165 | H | H | H | H | H | H | NHSO₂-ringA | CH₃ | H | H | H | Cl | H | H | | |
| 166 | CH₃ | H | H | H | H | H | NHSO₂-ringA | CH₃ | H | H | H | Cl | H | H | | |

TABLE 1-continued

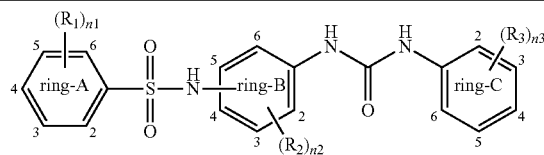

(Numbers shown around ring-A to ring-C in the formula above indicate positions on the rings. Similarly, numbers shown in the columns of ring-A to ring-C in the following tables indicate the positions on the rings.)

| COM-POUND | ring-A $(R_1)_{n1}$ | | | | | ring-B $(R_2)_{n2}$ and $NHSO_2$-ringASO$_2$-ringA | | | | | ring-C $(R_3)_{n3}$ | | | | | EX-AM- | MELT-ING POINT |
|---|---|---|---|---|---|---|---|---|---|---|---|---|---|---|---|---|---|
| No | 2 | 3 | 4 | 5 | 6 | 2 | 3 | 4 | 5 | 6 | 2 | 3 | 4 | 5 | 6 | PLE | (° C.) |
| 167 | H | CH$_3$ | H | H | H | H | NHSO$_2$-ringA | CH$_3$ | H | H | Cl | H | H | H | H | | |
| 168 | H | H | CH$_3$ | H | H | H | NHSO$_2$-ringA | CH$_3$ | H | H | Cl | H | H | H | H | | |
| 169 | Cl | H | H | H | H | H | NHSO$_2$-ringA | CH$_3$ | H | H | Cl | H | H | H | H | | |
| 170 | H | Cl | H | H | H | H | NHSO$_2$-ringA | CH$_3$ | H | H | Cl | H | H | H | H | | |
| 171 | H | H | Cl | H | H | H | NHSO$_2$-ringA | CH$_3$ | H | H | Cl | H | H | H | H | | |
| 172 | H | H | H | H | H | H | NHSO$_2$-ringA | H | H | CH$_3$ | Cl | H | H | H | H | | |
| 173 | CH$_3$ | H | H | H | H | H | NHSO$_2$-ringA | H | H | CH$_3$ | Cl | H | H | H | H | | |
| 174 | H | CH$_3$ | H | H | H | H | NHSO$_2$-ringA | H | H | CH$_3$ | Cl | H | H | H | H | | |
| 175 | H | H | CH$_3$ | H | H | H | NHSO$_2$-ringA | H | H | CH$_3$ | Cl | H | H | H | H | | |
| 176 | Cl | H | H | H | H | H | NHSO$_2$-ringA | H | H | CH$_3$ | Cl | H | H | H | H | | |
| 177 | H | Cl | H | H | H | H | NHSO$_2$-ringA | H | H | CH$_3$ | Cl | H | H | H | H | | |
| 178 | H | H | Cl | H | H | H | NHSO$_2$-ringA | H | H | CH$_3$ | Cl | H | H | H | H | | |
| 179 | H | H | H | H | H | NHSO$_2$-ringA | H | H | H | H | H | Cl | H | H | H | | |
| 180 | CH$_3$ | H | H | H | H | NHSO$_2$-ringA | H | H | H | H | H | Cl | H | H | H | | |
| 181 | H | CH$_3$ | H | H | H | NHSO$_2$-ringA | H | H | H | H | H | Cl | H | H | H | | |
| 182 | H | H | CH$_3$ | H | H | NHSO$_2$-ringA | H | H | H | H | H | Cl | H | H | H | | |
| 183 | Cl | H | H | H | H | NHSO$_2$-ringA | H | H | H | H | H | Cl | H | H | H | | |
| 184 | H | Cl | H | H | H | NHSO$_2$-ringA | H | H | H | H | H | Cl | H | H | H | | |
| 185 | H | H | Cl | H | H | NHSO$_2$-ringA | H | H | H | H | H | Cl | H | H | H | | |
| 186 | H | H | H | H | H | H | NHSO$_2$-ringA | H | H | H | H | Cl | H | H | H | | |
| 187 | CH$_3$ | H | H | H | H | H | NHSO$_2$-ringA | H | H | H | H | Cl | H | H | H | | |
| 188 | H | CH$_3$ | H | H | H | H | NHSO$_2$-ringA | H | H | H | H | Cl | H | H | H | | |
| 189 | H | H | CH$_3$ | H | H | H | NHSO$_2$-ringA | H | H | H | H | Cl | H | H | H | | |
| 190 | Cl | H | H | H | H | H | NHSO$_2$-ringA | H | H | H | H | Cl | H | H | H | | |
| 191 | H | Cl | H | H | H | H | NHSO$_2$-ringA | H | H | H | H | Cl | H | H | H | | |
| 192 | H | H | Cl | H | H | H | NHSO$_2$-ringA | H | H | H | H | Cl | H | H | H | | |
| 193 | H | H | H | H | H | H | H | NHSO$_2$-ringA | H | H | H | Cl | H | H | H | | |
| 194 | CH$_3$ | H | H | H | H | H | H | NHSO$_2$-ringA | H | H | H | Cl | H | H | H | | |
| 195 | H | CH$_3$ | H | H | H | H | H | NHSO$_2$-ringA | H | H | H | Cl | H | H | H | | |
| 196 | H | H | CH$_3$ | H | H | H | H | NHSO$_2$-ringA | H | H | H | Cl | H | H | H | | |
| 197 | Cl | H | H | H | H | H | H | NHSO$_2$-ringA | H | H | H | Cl | H | H | H | | |
| 198 | H | Cl | H | H | H | H | H | NHSO$_2$-ringA | H | H | H | Cl | H | H | H | | |

TABLE 1-continued

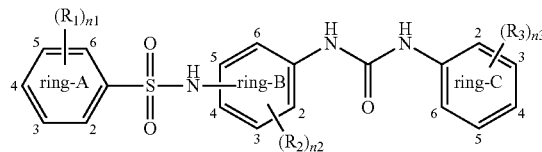

(Numbers shown around ring-A to ring-C in the formula above indicate positions on the rings. Similarly, numbers shown in the columns of ring-A to ring-C in the following tables indicate the positions on the rings.)

| COMPOUND | ring-A $(R_1)_{n1}$ | | | | | ring-B $(R_2)_{n2}$ and $NHSO_2$-ringASO$_2$-ringA | | | | | ring-C $(R_3)_{n3}$ | | | | | EXAMPLE | MELTING POINT |
|---|---|---|---|---|---|---|---|---|---|---|---|---|---|---|---|---|---|
| No | 2 | 3 | 4 | 5 | 6 | 2 | 3 | 4 | 5 | 6 | 2 | 3 | 4 | 5 | 6 | PLE | (° C.) |
| 199 | H | H | Cl | H | H | H | H | NHSO$_2$-ringA | H | H | H | Cl | H | H | H | | |
| 200 | H | H | H | H | H | H | NHSO$_2$-ringA | CH$_3$ | H | H | H | Cl | H | H | H | | |
| 201 | CH$_3$ | H | H | H | H | H | NHSO$_2$-ringA | CH$_3$ | H | H | H | Cl | H | H | H | | |
| 202 | H | CH$_3$ | H | H | H | H | NHSO$_2$-ringA | CH$_3$ | H | H | H | Cl | H | H | H | | |
| 203 | H | H | CH$_3$ | H | H | H | NHSO$_2$-ringA | CH$_3$ | H | H | H | Cl | H | H | H | | |
| 204 | Cl | H | H | H | H | H | NHSO$_2$-ringA | CH$_3$ | H | H | H | Cl | H | H | H | | |
| 205 | H | Cl | H | H | H | H | NHSO$_2$-ringA | CH$_3$ | H | H | H | Cl | H | H | H | | |
| 206 | H | H | Cl | H | H | H | NHSO$_2$-ringA | CH$_3$ | H | H | H | Cl | H | H | H | | |
| 207 | H | H | H | H | H | H | NHSO$_2$-ringA | H | H | CH$_3$ | H | Cl | H | H | H | | |
| 208 | CH$_3$ | H | H | H | H | H | NHSO$_2$-ringA | H | H | CH$_3$ | H | Cl | H | H | H | | |
| 209 | H | CH$_3$ | H | H | H | H | NHSO$_2$-ringA | H | H | CH$_3$ | H | Cl | H | H | H | | |
| 210 | H | H | CH$_3$ | H | H | H | NHSO$_2$-ringA | H | H | CH$_3$ | H | Cl | H | H | H | | |
| 211 | Cl | H | H | H | H | H | NHSO$_2$-ringA | H | H | CH$_3$ | H | Cl | H | H | H | | |
| 212 | H | Cl | H | H | H | H | NHSO$_2$-ringA | H | H | CH$_3$ | H | Cl | H | H | H | | |
| 213 | H | H | Cl | H | H | H | NHSO$_2$-ringA | H | H | CH$_3$ | H | Cl | H | H | H | | |
| 214 | H | H | H | H | H | NHSO$_2$-ringA | H | H | H | H | H | H | Cl | H | H | 22 | 160-161 |
| 215 | CH$_3$ | H | H | H | H | NHSO$_2$-ringA | H | H | H | H | H | H | Cl | H | H | 21 | 192-194 |
| 216 | H | CH$_3$ | H | H | H | NHSO$_2$-ringA | H | H | H | H | H | H | Cl | H | H | 20 | 174-181 |
| 217 | H | H | CH$_3$ | H | H | NHSO$_2$-ringA | H | H | H | H | H | H | Cl | H | H | 19 | 100-103 |
| 218 | Cl | H | H | H | H | NHSO$_2$-ringA | H | H | H | H | H | H | Cl | H | H | | |
| 219 | H | Cl | H | H | H | NHSO$_2$-ringA | H | H | H | H | H | H | Cl | H | H | 23 | 103-106 |
| 220 | H | H | Cl | H | H | NHSO$_2$-ringA | H | H | H | H | H | H | Cl | H | H | | |
| 221 | H | H | H | H | H | H | NHSO$_2$-ringA | H | H | H | H | H | Cl | H | H | | |
| 222 | CH$_3$ | H | H | H | H | H | NHSO$_2$-ringA | H | H | H | H | H | Cl | H | H | | |
| 223 | H | CH$_3$ | H | H | H | H | NHSO$_2$-ringA | H | H | H | H | H | Cl | H | H | | |
| 224 | H | H | CH$_3$ | H | H | H | NHSO$_2$-ringA | H | H | H | H | H | Cl | H | H | | |
| 225 | Cl | H | H | H | H | H | NHSO$_2$-ringA | H | H | H | H | H | Cl | H | H | | |
| 226 | H | Cl | H | H | H | H | NHSO$_2$-ringA | H | H | H | H | H | Cl | H | H | | |
| 227 | H | H | Cl | H | H | H | NHSO$_2$-ringA | H | H | H | H | H | Cl | H | H | | |
| 228 | H | H | H | H | H | H | H | NHSO$_2$-ringA | H | H | H | H | Cl | H | H | | |
| 229 | CH$_3$ | H | H | H | H | H | H | NHSO$_2$-ringA | H | H | H | H | Cl | H | H | | |
| 230 | H | CH$_3$ | H | H | H | H | H | NHSO$_2$-ringA | H | H | H | H | Cl | H | H | | |

TABLE 1-continued

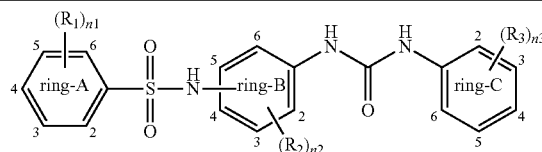

(Numbers shown around ring-A to ring-C in the formula above indicate positions on the rings. Similarly, numbers shown in the columns of ring-A to ring-C in the following tables indicate the positions on the rings.)

| COMPOUND | ring-A $(R_1)_{n1}$ | | | | | ring-B $(R_2)_{n2}$ and $NHSO_2$-ringA$SO_2$-ringA | | | | | ring-C $(R_3)_{n3}$ | | | | | EXAMPLE | MELTING POINT (°C.) |
|---|---|---|---|---|---|---|---|---|---|---|---|---|---|---|---|---|---|
| No | 2 | 3 | 4 | 5 | 6 | 2 | 3 | 4 | 5 | 6 | 2 | 3 | 4 | 5 | 6 | | |
| 231 | H | H | $CH_3$ | H | H | H | H | $NHSO_2$-ringA | H | H | H | H | Cl | H | H | | |
| 232 | Cl | H | H | H | H | H | H | $NHSO_2$-ringA | H | H | H | H | Cl | H | H | | |
| 233 | H | Cl | H | H | H | H | H | $NHSO_2$-ringA | H | H | H | H | Cl | H | H | | |
| 234 | H | H | Cl | H | H | H | H | $NHSO_2$-ringA | H | H | H | H | Cl | H | H | | |
| 235 | H | H | H | H | H | H | $NHSO_2$-ringA | $CH_3$ | H | H | H | H | Cl | H | H | | |
| 236 | $CH_3$ | H | H | H | H | H | $NHSO_2$-ringA | $CH_3$ | H | H | H | H | Cl | H | H | | |
| 237 | H | $CH_3$ | H | H | H | H | $NHSO_2$-ringA | $CH_3$ | H | H | H | H | Cl | H | H | | |
| 238 | H | H | $CH_3$ | H | H | H | $NHSO_2$-ringA | $CH_3$ | H | H | H | H | Cl | H | H | | |
| 239 | Cl | H | H | H | H | H | $NHSO_2$-ringA | $CH_3$ | H | H | H | H | Cl | H | H | | |
| 240 | H | Cl | H | H | H | H | $NHSO_2$-ringA | $CH_3$ | H | H | H | H | Cl | H | H | | |
| 241 | H | H | Cl | H | H | H | $NHSO_2$-ringA | $CH_3$ | H | H | H | H | Cl | H | H | | |
| 242 | H | H | H | H | H | H | $NHSO_2$-ringA | H | H | $CH_3$ | H | H | Cl | H | H | | |
| 243 | $CH_3$ | H | H | H | H | H | $NHSO_2$-ringA | H | H | $CH_3$ | H | H | Cl | H | H | | |
| 244 | H | $CH_3$ | H | H | H | H | $NHSO_2$-ringA | H | H | $CH_3$ | H | H | Cl | H | H | | |
| 245 | H | H | $CH_3$ | H | H | H | $NHSO_2$-ringA | H | H | $CH_3$ | H | H | Cl | H | H | | |
| 246 | Cl | H | H | H | H | H | $NHSO_2$-ringA | H | H | $CH_3$ | H | H | Cl | H | H | | |
| 247 | H | Cl | H | H | H | H | $NHSO_2$-ringA | H | H | $CH_3$ | H | H | Cl | H | H | | |
| 248 | H | H | Cl | H | H | H | $NHSO_2$-ringA | H | H | $CH_3$ | H | H | Cl | H | H | | |
| 249 | H | H | H | H | H | $NHSO_2$-ringA | H | H | H | H | H | H | $CH_3O$ | H | H | | |
| 250 | $CH_3$ | H | H | H | H | $NHSO_2$-ringA | H | H | H | H | H | H | $CH_3O$ | H | H | | |
| 251 | H | $CH_3$ | H | H | H | $NHSO_2$-ringA | H | H | H | H | H | H | $CH_3O$ | H | H | | |
| 252 | H | H | $CH_3$ | H | H | $NHSO_2$-ringA | H | H | H | H | H | H | $CH_3O$ | H | H | 16 | 97-106 |
| 253 | Cl | H | H | H | H | $NHSO_2$-ringA | H | H | H | H | H | H | $CH_3O$ | H | H | | |
| 254 | H | Cl | H | H | H | $NHSO_2$-ringA | H | H | H | H | H | H | $CH_3O$ | H | H | | |
| 255 | H | H | Cl | H | H | $NHSO_2$-ringA | H | H | H | H | H | H | $CH_3O$ | H | H | | |
| 256 | H | H | H | H | H | H | $NHSO_2$-ringA | H | H | H | H | H | $CH_3O$ | H | H | | |
| 257 | $CH_3$ | H | H | H | H | H | $NHSO_2$-ringA | H | H | H | H | H | $CH_3O$ | H | H | | |
| 258 | H | $CH_3$ | H | H | H | H | $NHSO_2$-ringA | H | H | H | H | H | $CH_3O$ | H | H | | |
| 259 | H | H | $CH_3$ | H | H | H | $NHSO_2$-ringA | H | H | H | H | H | $CH_3O$ | H | H | | |
| 260 | Cl | H | H | H | H | H | $NHSO_2$-ringA | H | H | H | H | H | $CH_3O$ | H | H | | |
| 261 | H | Cl | H | H | H | H | $NHSO_2$-ringA | H | H | H | H | H | $CH_3O$ | H | H | | |
| 262 | H | H | Cl | H | H | H | $NHSO_2$-ringA | H | H | H | H | H | $CH_3O$ | H | H | | |

TABLE 1-continued

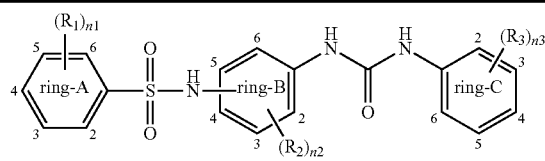

(Numbers shown around ring-A to ring-C in the formula above indicate positions on the rings. Similarly, numbers shown in the columns of ring-A to ring-C in the following tables indicate the positions on the rings.)

| COMPOUND | ring-A $(R_1)_{n1}$ | | | | | ring-B $(R_2)_{n2}$ and $NHSO_2$-ringASO$_2$-ringA | | | | | ring-C $(R_3)_{n3}$ | | | | | EXAMPLE | MELTING POINT (°C.) |
|---|---|---|---|---|---|---|---|---|---|---|---|---|---|---|---|---|---|
| No | 2 | 3 | 4 | 5 | 6 | 2 | 3 | 4 | 5 | 6 | 2 | 3 | 4 | 5 | 6 | | |
| 263 | H | H | H | H | H | H | H | NHSO$_2$-ringA | H | H | H | H | CH$_3$O | H | H | | |
| 264 | CH$_3$ | H | H | H | H | H | H | NHSO$_2$-ringA | H | H | H | H | CH$_3$O | H | H | | |
| 265 | H | CH$_3$ | H | H | H | H | H | NHSO$_2$-ringA | H | H | H | H | CH$_3$O | H | H | | |
| 266 | H | H | CH$_3$ | H | H | H | H | NHSO$_2$-ringA | H | H | H | H | CH$_3$O | H | H | | |
| 267 | Cl | H | H | H | H | H | H | NHSO$_2$-ringA | H | H | H | H | CH$_3$O | H | H | | |
| 268 | H | Cl | H | H | H | H | H | NHSO$_2$-ringA | H | H | H | H | CH$_3$O | H | H | | |
| 269 | H | H | Cl | H | H | H | H | NHSO$_2$-ringA | H | H | H | H | CH$_3$O | H | H | | |
| 270 | H | H | H | H | H | H | NHSO$_2$-ringA | CH$_3$ | H | H | H | H | CH$_3$O | H | H | | |
| 271 | CH$_3$ | H | H | H | H | H | NHSO$_2$-ringA | CH$_3$ | H | H | H | H | CH$_3$O | H | H | | |
| 272 | H | CH$_3$ | H | H | H | H | NHSO$_2$-ringA | CH$_3$ | H | H | H | H | CH$_3$O | H | H | | |
| 273 | H | H | CH$_3$ | H | H | H | NHSO$_2$-ringA | CH$_3$ | H | H | H | H | CH$_3$O | H | H | | |
| 274 | Cl | H | H | H | H | H | NHSO$_2$-ringA | CH$_3$ | H | H | H | H | CH$_3$O | H | H | | |
| 275 | H | Cl | H | H | H | H | NHSO$_2$-ringA | CH$_3$ | H | H | H | H | CH$_3$O | H | H | | |
| 276 | H | H | Cl | H | H | H | NHSO$_2$-ringA | CH$_3$ | H | H | H | H | CH$_3$O | H | H | | |
| 277 | H | H | H | H | H | H | NHSO$_2$-ringA | H | H | CH$_3$ | H | H | CH$_3$O | H | H | | |
| 278 | CH$_3$ | H | H | H | H | H | NHSO$_2$-ringA | H | H | CH$_3$ | H | H | CH$_3$O | H | H | | |
| 279 | H | CH$_3$ | H | H | H | H | NHSO$_2$-ringA | H | H | CH$_3$ | H | H | CH$_3$O | H | H | | |
| 280 | H | H | CH$_3$ | H | H | H | NHSO$_2$-ringA | H | H | CH$_3$ | H | H | CH$_3$O | H | H | | |
| 281 | Cl | H | H | H | H | H | NHSO$_2$-ringA | H | H | CH$_3$ | H | H | CH$_3$O | H | H | | |
| 282 | H | Cl | H | H | H | H | NHSO$_2$-ringA | H | H | CH$_3$ | H | H | CH$_3$O | H | H | | |
| 283 | H | H | Cl | H | H | H | NHSO$_2$-ringA | H | H | CH$_3$ | H | H | CH$_3$O | H | H | | |
| 284 | H | H | H | H | H | NHSO$_2$-ringA | H | H | H | H | H | H | F | H | H | | |
| 285 | CH$_3$ | H | H | H | H | NHSO$_2$-ringA | H | H | H | H | H | H | F | H | H | | |
| 286 | H | CH$_3$ | H | H | H | NHSO$_2$-ringA | H | H | H | H | H | H | F | H | H | | |
| 287 | H | H | CH$_3$ | H | H | NHSO$_2$-ringA | H | H | H | H | H | H | F | H | H | 17 | 149-153 |
| 288 | Cl | H | H | H | H | NHSO$_2$-ringA | H | H | H | H | H | H | F | H | H | | |
| 289 | H | Cl | H | H | H | NHSO$_2$-ringA | H | H | H | H | H | H | F | H | H | | |
| 290 | H | H | Cl | H | H | NHSO$_2$-ringA | H | H | H | H | H | H | F | H | H | | |
| 291 | H | H | H | H | H | H | NHSO$_2$-ringA | H | H | H | H | H | F | H | H | | |
| 292 | CH$_3$ | H | H | H | H | H | NHSO$_2$-ringA | H | H | H | H | H | F | H | H | | |
| 293 | H | CH$_3$ | H | H | H | H | NHSO$_2$-ringA | H | H | H | H | H | F | H | H | | |
| 294 | H | H | CH$_3$ | H | H | H | NHSO$_2$-ringA | H | H | H | H | H | F | H | H | | |

TABLE 1-continued

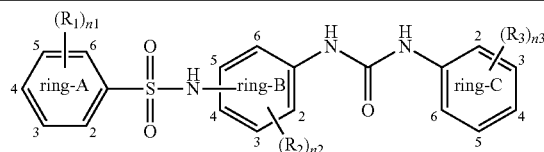

(Numbers shown around ring-A to ring-C in the formula above indicate positions on the rings. Similarly, numbers shown in the columns of ring-A to ring-C in the following tables indicate the positions on the rings.)

| COMPOUND No | ring-A (R₁)ₙ₁ 2 | 3 | 4 | 5 | 6 | ring-B (R₂)ₙ₂ and NHSO₂-ringASO₂-ringA 2 | 3 | 4 | 5 | 6 | ring-C (R₃)ₙ₃ 2 | 3 | 4 | 5 | 6 | EXAMPLE | MELTING POINT (°C.) |
|---|---|---|---|---|---|---|---|---|---|---|---|---|---|---|---|---|---|
| 295 | Cl | H | H | H | H | H | NHSO₂-ringA | H | H | H | H | H | F | H | H | | |
| 296 | H | Cl | H | H | H | H | NHSO₂-ringA | H | H | H | H | H | F | H | H | | |
| 297 | H | H | Cl | H | H | H | NHSO₂-ringA | H | H | H | H | H | F | H | H | | |
| 298 | H | H | H | H | H | H | H | NHSO₂-ringA | H | H | H | H | F | H | H | | |
| 299 | CH₃ | H | H | H | H | H | H | NHSO₂-ringA | H | H | H | H | F | H | H | | |
| 300 | H | CH₃ | H | H | H | H | H | NHSO₂-ringA | H | H | H | H | F | H | H | | |
| 301 | H | H | CH₃ | H | H | H | H | NHSO₂-ringA | H | H | H | H | F | H | H | | |
| 302 | Cl | H | H | H | H | H | H | NHSO₂-ringA | H | H | H | H | F | H | H | | |
| 303 | H | Cl | H | H | H | H | H | NHSO₂-ringA | H | H | H | H | F | H | H | | |
| 304 | H | H | Cl | H | H | H | H | NHSO₂-ringA | H | H | H | H | F | H | H | | |
| 305 | H | H | H | H | H | H | NHSO₂-ringA | CH₃ | H | H | H | H | F | H | H | | |
| 306 | CH₃ | H | H | H | H | H | NHSO₂-ringA | CH₃ | H | H | H | H | F | H | H | | |
| 307 | H | CH₃ | H | H | H | H | NHSO₂-ringA | CH₃ | H | H | H | H | F | H | H | | |
| 308 | H | H | CH₃ | H | H | H | NHSO₂-ringA | CH₃ | H | H | H | H | F | H | H | | |
| 309 | Cl | H | H | H | H | H | NHSO₂-ringA | CH₃ | H | H | H | H | F | H | H | | |
| 310 | H | Cl | H | H | H | H | NHSO₂-ringA | CH₃ | H | H | H | H | F | H | H | | |
| 311 | H | H | Cl | H | H | H | NHSO₂-ringA | CH₃ | H | H | H | H | F | H | H | | |
| 312 | H | H | H | H | H | H | NHSO₂-ringA | H | H | CH₃ | H | H | F | H | H | | |
| 313 | CH₃ | H | H | H | H | H | NHSO₂-ringA | H | H | CH₃ | H | H | F | H | H | | |
| 314 | H | CH₃ | H | H | H | H | NHSO₂-ringA | H | H | CH₃ | H | H | F | H | H | | |
| 315 | H | H | CH₃ | H | H | H | NHSO₂-ringA | H | H | CH₃ | H | H | F | H | H | | |
| 316 | Cl | H | H | H | H | H | NHSO₂-ringA | H | H | CH₃ | H | H | F | H | H | | |
| 317 | H | Cl | H | H | H | H | NHSO₂-ringA | H | H | CH₃ | H | H | F | H | H | | |
| 318 | H | H | Cl | H | H | H | NHSO₂-ringA | H | H | CH₃ | H | H | F | H | H | | |
| 319 | H | H | H | H | H | NHSO₂-ringA | H | H | H | H | H | H | CF₃ | H | H | | |
| 320 | CH₃ | H | H | H | H | NHSO₂-ringA | H | H | H | H | H | H | CF₃ | H | H | | |
| 321 | H | CH₃ | H | H | H | NHSO₂-ringA | H | H | H | H | H | H | CF₃ | H | H | | |
| 322 | H | H | CH₃ | H | H | NHSO₂-ringA | H | H | H | H | H | H | CF₃ | H | H | 18 | 91-96 |
| 323 | Cl | H | H | H | H | NHSO₂-ringA | H | H | H | H | H | H | CF₃ | H | H | | |
| 324 | H | Cl | H | H | H | NHSO₂-ringA | H | H | H | H | H | H | CF₃ | H | H | | |
| 325 | H | H | Cl | H | H | NHSO₂-ringA | H | H | H | H | H | H | CF₃ | H | H | | |
| 326 | H | H | H | H | H | H | NHSO₂-ringA | H | H | H | H | H | CF₃ | H | H | | |

TABLE 1-continued

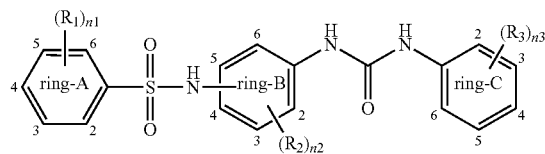

(Numbers shown around ring-A to ring-C in the formula above indicate positions on the rings. Similarly, numbers shown in the columns of ring-A to ring-C in the following tables indicate the positions on the rings.)

| COM-POUND No | ring-A $(R_1)_{n1}$ 2 | 3 | 4 | 5 | 6 | ring-B $(R_2)_{n2}$ and NHSO$_2$-ringASO$_2$-ringA 2 | 3 | 4 | 5 | 6 | ring-C $(R_3)_{n3}$ 2 | 3 | 4 | 5 | 6 | EX-AM-PLE | MELT-ING POINT (° C.) |
|---|---|---|---|---|---|---|---|---|---|---|---|---|---|---|---|---|---|
| 327 | CH$_3$ | H | H | H | H | H | NHSO$_2$-ringA | H | H | H | H | H | CF$_3$ | H | H | | |
| 328 | H | CH$_3$ | H | H | H | H | NHSO$_2$-ringA | H | H | H | H | H | CF$_3$ | H | H | | |
| 329 | H | H | CH$_3$ | H | H | H | NHSO$_2$-ringA | H | H | H | H | H | CF$_3$ | H | H | | |
| 330 | Cl | H | H | H | H | H | NHSO$_2$-ringA | H | H | H | H | H | CF$_3$ | H | H | | |
| 331 | H | Cl | H | H | H | H | NHSO$_2$-ringA | H | H | H | H | H | CF$_3$ | H | H | | |
| 332 | H | H | Cl | H | H | H | NHSO$_2$-ringA | H | H | H | H | H | CF$_3$ | H | H | | |
| 333 | H | H | H | H | H | H | H | NHSO$_2$-ringA | H | H | H | H | CF$_3$ | H | H | | |
| 334 | CH$_3$ | H | H | H | H | H | H | NHSO$_2$-ringA | H | H | H | H | CF$_3$ | H | H | | |
| 335 | H | CH$_3$ | H | H | H | H | H | NHSO$_2$-ringA | H | H | H | H | CF$_3$ | H | H | | |
| 336 | H | H | CH$_3$ | H | H | H | H | NHSO$_2$-ringA | H | H | H | H | CF$_3$ | H | H | | |
| 337 | Cl | H | H | H | H | H | H | NHSO$_2$-ringA | H | H | H | H | CF$_3$ | H | H | | |
| 338 | H | Cl | H | H | H | H | H | NHSO$_2$-ringA | H | H | H | H | CF$_3$ | H | H | | |
| 339 | H | H | Cl | H | H | H | H | NHSO$_2$-ringA | H | H | H | H | CF$_3$ | H | H | | |
| 340 | H | H | H | H | H | H | NHSO$_2$-ringA | CH$_3$ | H | H | H | H | CF$_3$ | H | H | | |
| 341 | CH$_3$ | H | H | H | H | H | NHSO$_2$-ringA | CH$_3$ | H | H | H | H | CF$_3$ | H | H | | |
| 342 | H | CH$_3$ | H | H | H | H | NHSO$_2$-ringA | CH$_3$ | H | H | H | H | CF$_3$ | H | H | | |
| 343 | H | H | CH$_3$ | H | H | H | NHSO$_2$-ringA | CH$_3$ | H | H | H | H | CF$_3$ | H | H | | |
| 344 | Cl | H | H | H | H | H | NHSO$_2$-ringA | CH$_3$ | H | H | H | H | CF$_3$ | H | H | | |
| 345 | H | Cl | H | H | H | H | NHSO$_2$-ringA | CH$_3$ | H | H | H | H | CF$_3$ | H | H | | |
| 346 | H | H | Cl | H | H | H | NHSO$_2$-ringA | CH$_3$ | H | H | H | H | CF$_3$ | H | H | | |
| 347 | H | H | H | H | H | H | NHSO$_2$-ringA | H | H | CH$_3$ | H | H | CF$_3$ | H | H | | |
| 348 | CH$_3$ | H | H | H | H | H | NHSO$_2$-ringA | H | H | CH$_3$ | H | H | CF$_3$ | H | H | | |
| 349 | H | CH$_3$ | H | H | H | H | NHSO$_2$-ringA | H | H | CH$_3$ | H | H | CF$_3$ | H | H | | |
| 350 | H | H | CH$_3$ | H | H | H | NHSO$_2$-ringA | H | H | CH$_3$ | H | H | CF$_3$ | H | H | | |
| 351 | Cl | H | H | H | H | H | NHSO$_2$-ringA | H | H | CH$_3$ | H | H | CF$_3$ | H | H | | |
| 352 | H | Cl | H | H | H | H | NHSO$_2$-ringA | H | H | CH$_3$ | H | H | CF$_3$ | H | H | | |
| 353 | H | H | Cl | H | H | H | NHSO$_2$-ringA | H | H | CH$_3$ | H | H | CF$_3$ | H | H | | |

Compound No. 354 Example 24 Melting point: 165-168° C.

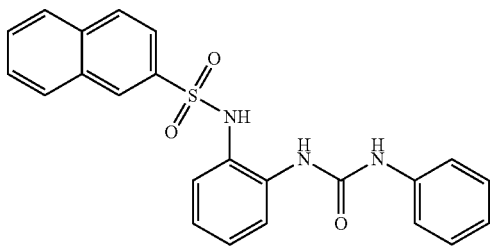 [SMILES: O=C(Nc1ccccc1)Nc1ccccc1NS(=O)(=O)c1ccc2ccccc2c1]

No. 355 Example 25 Melting point: 199-201° C.

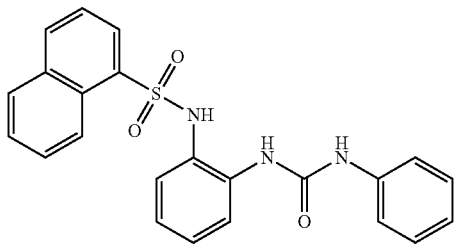 [SMILES: O=C(Nc1ccccc1)Nc1ccccc1NS(=O)(=O)c1cccc2ccccc12]

(Stability of Non-Phenol Compounds Represented by Formulas (I) to (III))

The non-phenol compounds of the present invention are stable as a compound. Specifically, they are not hydrolyzed even when stored in contact with water, and there is no need to consider the safety of a hydrolysate. Besides, since these compounds do not have a structure of a phenol skeleton, there is no possibility that they correspond to an endocrine disruptor.

(Recording Material)

A recording material of the present invention can be used for any purpose as long as it is a recording material containing a color former and at least one of the non-phenol compounds represented by the formulas (I), (II) and (III), and for example, it can be used as a thermal recording material or a pressure-sensitive copying material.

The proportion of the compound(s) of at least one of the non-phenol compounds represented by the formulas (I), (II) and (III) to the color former used is usually 0.01 to 10 parts by mass, preferably 0.5 to 10 parts by mass, and more preferably 1.0 to 5 parts by mass, with respect to 1 part by mass of the color former.

(Other Components in Recording Material)

The recording material of the present invention can contain, in addition to the color former and the non-phenol compound(s) represented by the formula (I), (II) or (III), one or more of color-developing agents, image stabilizers, sensitizers, fillers, dispersants, antioxidants, desensitizers, anti-tack agents, antifoaming agents, light stabilizers, fluorescent brightening agents, etc., known in the art, as needed. The amount of each of the components used is in the range of usually 0.1 to 15 parts by mass, preferably 1 to 10 parts by mass, with respect to 1 part by mass of the color former.

These agents may be contained in a color-developing layer or may be contained in any layer, for example, a protective layer, when they consist of a multilayer structure. Particularly, when an overcoat layer or an undercoat layer is provided in the upper and/or lower parts of the color-developing layer, these layers can contain antioxidants, light stabilizers, etc. Furthermore, these antioxidants or light stabilizers can be contained in a form encapsulated in microcapsules, as needed, in these layers.

Examples of the color former used in the recording material of the present invention can include, but not limited to, fluoran, phthalide, lactam, triphenylmethane, phenothiazine, and spiropyran leuco dyes. Any color former that forms a color by contact with the color-developing agent, which is an acidic substance, can be used. Moreover, these color formers can be used alone to produce a recording material with the color to be formed, as a matter of course. Alternatively, two or more thereof can be mixed for use. For example, three primary color (red, blue, and green) formers or black color formers can be mixed and used to produce a recording material that develops a true black color.

Examples of the fluoran color formers include 3,3-bis(p-dimethylaminophenyl)-phthalide, 3,3-bis(p-dimethylaminophenyl)-6-dimethylaminophthalide (also known as crystal violet lactone), 3,3-bis(p-dimethylaminophenyl)-6-diethylaminophthalide, 3,3-bis(p-dimethylaminophenyl)-6-chlorophthalide, 3,3-bis(p-dibutylaminophenyl)-phthalide, 3-cyclohexylamino-6-chlorofluoran, 3-dimethylamino-5,7-dimethylfluoran, 3-N-methyl-N-isopropylamino-6-methyl-7-anilinofluoran, 3-N-methyl-N-isobutylamino-6-methyl-7-anilinofluoran, 3-N-methyl-N-isoamylamino-6-methyl-7-anilinofluoran, 3-diethylamino-7-chlorofluoran, 3-diethylamino-6,8-dimethylfluoran, 3-diethylamino-7-methylfluoran, 3-diethylamino-7,8-benzofluoran, 3-diethylamino-6-methyl-7-chlorofluoran, 3-dibutylamino-6-methyl-7-bromofluoran, 3-(N-p-tolyl-N-ethylamino)-6-methyl-7-anilinofluoran, 3-pyrrolidino-6-methylamino-7-anilinofluoran, 2-{N-(3'-trifluoromethylphenyl)amino}-6-diethylaminofluoran, 2-{3,6-bis(diethylamino)-9-(o-chloroanilino)xanthylbenzoic acid lactam}, 3-diethylamino-6-methyl-7-(m-trichloromethylanilino)fluoran, 3-diethylamino-7-(o-chloroanilino)fluoran, 3-dibutylamino-7-(o-chloroanilino)fluoran, 3-N-methyl-N-amylamino-6-methyl-7-anilinofluoran, 3-N-methyl-N-cyclohexylamino-6-methyl-7-anilinofluoran, 3-diethylamino-6-methyl-7-anilinofluoran, 3-diethylamino-6-methyl-7-(2',4'-dimethylanilino)fluoran, 3-(N,N-diethylamino)-5-methyl-7-(N,N-dibenzylamino)fluoran, 3-(N,N-diethylamino)-7-(N,N-dibenzylamino)fluoran, 3-(N-ethyl-N-isobutylamino)-6-methyl-7-anilinofluoran, 3-(N-ethyl-N-propylamino)-6-methyl-7-anilinofluoran, 3-(N-methyl-N-propylamino)-6-methyl-7-anilinofluoran, 3-(N-ethyl-N-isopentylamino)-6-methyl-7-anilinofluoran, 3-(N-ethyl-N-toluidino)-6-methyl-7-anilino-fluoran, 3-pyrrolidino-6-methyl-7-anilinofluoran, 3-piperidino-6-methyl-7-anilinofluoran, 3-dimethylamino-7-(m-trifluoromethylanilino)fluoran, 3-dipentylamino-6-methyl-7-anilinofluoran, 3-(N-ethoxypropyl-N-ethylamino)-6-methyl-7-anilinofluoran, 3-dibutylamino-7-(o-fluoroanilino)fluoran, 3-diethylaminobenzo[a]fluoran, 3-diethylamino-5-methyl-7-benzylaminofluoran, 3-diethylamino-5-chlorofluoran, 3-diethylamino-6-(N,N'-dibenzylamino)fluoran, 3,6-dimethoxyfluoran, 2,4-dimethyl-6-(4-dimethylaminophenyl)aminofluoran, 3-diethylamino-7-(m-trifluoromethylanilino)fluoran, 3-diethylamino-6-methyl-7-octylaminofluoran, 3-diethylamino-6-methyl-7-(m-tolylamino)fluoran, 3-diethylamino-6-methyl-7-(2,4-xylylamino)fluoran, 3-diethylamino-7-(o-fluoroanilino)fluoran, 3-diphenylamino-6-methyl-7-anilinofluoran, benzoylleucomethylene blue, 6'-chloro-8'-methoxy-benzindolino-spiropyran, 6'-bromo-3'-methoxy-benzindolino-spiropyran, 3-(2'-hydroxy-4'-dimethylaminophenyl)-3-(2'-methoxy-5'-chlorophenyl)phthalide, 3-(2'-hydroxy-4'-dimethylaminophenyl)-3-(2'-methoxy-5'-nitrophenyl) phthalide, 3-(2'-hydroxy-4'-diethylaminophenyl)-3-(2'- methoxy-5'-methylphenyl)phthalide, 3-(2'-methoxy-4'-dimethylaminophenyl)-3-(2'-hydroxy-4'-chloro-5'-methylphenyl)phthalide, 3-morpholino-7-(N-propyl-trifluoromethylanilino)fluoran, 3-pyrrolidino-7-trifluoromethylanilinofluoran, 3-diethylamino-5-chloro-7-(N-benzyl-trifluoromethylanilino)fluoran, 3-pyrrolidino-7-(di-p-chlorophenyl)methylaminofluoran, 3-diethylamino-5-chloro-7-(α-phenylethylamino)fluoran, 3-(N-ethyl-p-toluidino)-7-(α-phenylethylamino)fluoran, 3-diethylamino-7-(o-methoxycarbonylphenylamino)fluoran, 3-diethylamino-5-methyl-7-(α-phenylethylamino)fluoran, 3-diethylamino-7-piperidinofluoran, 2-chloro-3-(N-methyl-toluidino)-7-(p-n-butylanilino)fluoran, 3-(N-methyl-N-isopropylamino)-6-methyl-7-anilinofluoran, 3-dibutylamino-6-methyl-7-anilinofluoran, 3-dipentylamino-6-methyl-7-anilinofluoran, 3,6-bis(dimethylamino)fluorenespiro(9,3')-6'-dimethylaminophthalide, 3-(N-benzyl-N-cyclohexylamino)-5,6-benzo-7-α-naphthylamino-4'-bromofluoran, 3-diethylamino-6-chloro-7-anilinofluoran, 3-N-ethyl-N-(2-ethoxypropyl)amino-6-methyl-7-anilinofluoran, 3-N-ethyl-N-tetrahydrofurfurylamino-6-methyl-7-anilinofluoran, 3-diethylamino-6-methyl-7-mesidino-4',5'-benzofluoran, and 3-(N-ethyl-p-toluidino)-7-(methylphenylamino)fluoran.

Among these color formers, preferable examples thereof can include 3,3-bis(p-dimethylaminophenyl)-6-dimethylaminophthalide, 3-cyclohexylamino-6-chlorofluoran, 3-diethylamino-7-chlorofluoran, 3-diethylamino-6,8-dimethylfluoran, 3-diethylamino-7-methylfluoran, 3-diethylamino-7,8-benzofluoran, 3-diethylamino-6-methyl-7-chlorofluoran, 3-dibutylamino-6-methyl-7-bromofluoran, 3-diethylamino-7-(o-chloroanilino)fluoran, 3-dibutylamino-7-(o-chloroanilino)fluoran, 3-N-methyl-N-cyclohexylamino-6-methyl-7-anilinofluoran, 3-(N,N-diethylamino)-5-methyl-7-(N,N-dibenzylamino)fluoran, 3-(N,N-diethylamino)-7-(N,N-dibenzylamino)fluoran, 3-(N-ethyl-N-isobutylamino)-6-methyl-7-anilinofluoran, 3-(N-methyl-N-propylamino)-6-methyl-7-anilinofluoran, 3-(N-ethyl-N-isopentylamino)-6-methyl-7-anilinofluoran, 3-(N-ethyl-N-toluidino)-6-methyl-7-anilino-fluoran, 3-(N-ethoxypropyl-N-ethylamino)-6-methyl-7-anilinofluoran, 3-dibutylamino-7-(o-fluoroanilino)fluoran, 3-diethylamino-7-(m-trifluoromethylanilino)fluoran, 3-diethylamino-6-methyl-7-octylaminofluoran, 3-diethylamino-6-methyl-7-(m-tolylamino)fluoran, 3-diethylamino-7-(o-fluoroanilino)fluoran, 3-diphenylamino-6-methyl-7-anilinofluoran, benzoylleucomethylene blue, 3-dibutylamino-6-methyl-7-anilinofluoran, 3-N-ethyl-N-tetrahydrofurfurylamino-6-methyl-7-anilinofluoran, and 3-(N-ethyl-p-toluidino)-7-(methylphenylamino)fluoran.

Moreover, examples of near infrared absorbing dyes include 3-[4-[4-(4-anilino)-anilino]anilino]-6-methyl-7-chlorofluoran, 3,3-bis[2-(4-dimethylaminophenyl)-2-(4-methoxyphenyl)vinyl]-4,5,6,7-tetrachlorophthalide, and 3,6,6'-tris(dimethylamino)spiro(fluorene-9,3'-phthalide).

At least one of the non-phenol compounds represented by the formulas (I), (II) and (III) of the present invention is suitably used as a color-developing agent mainly in a thermal recording material, and these compounds alone can be used or these compounds can be used together with a plurality of known color-developing agents. The ratio among them is arbitrary.

Examples of other color-developing agents can specifically include the followings: bisphenol compounds such as bisphenol A, 4,4'-sec-butylidenebisphenol, 4,4'-cyclohexylidenebisphenol, 2,2'-bis(4-hydroxyphenyl)-3,3'-dimethylbutane, 2,2'-dihydroxydiphenyl, pentamethylene-bis(4-hydroxybenzoate), 2,2-dimethyl-3,3-di(4-hydroxyphenyl)pentane, 2,2-di(4-hydroxyphenyl)hexane, 2,2-bis(4-hydroxyphenyl)propane, 2,2-bis(4-hydroxyphenyl)butane, 2,2-bis(4-hydroxy-3-methylphenyl)propane, 4,4'-(1-phenylethylidene)bisphenol, 4,4'-ethylidenebisphenol, (hydroxyphenyl)methylphenol, 2,2'-bis(4-hydroxy-3-phenyl-phenyl)propane, 4,4'-(1,3-phenylenediisopropylidene)bisphenol, 4,4'-(1,4-phenylenediisopropylidene)bisphenol, and butyl 2,2-bis(4-hydroxyphenyl)acetate; sulfur-containing bisphenol compounds such as 4,4'-dihydroxydiphenyl thioether, 1,7-di(4-hydroxyphenylthio)-3,5-dioxaheptane, 2,2'-bis(4-hydroxyphenylthio)diethyl ether, and 4,4'-dihydroxy-3,3'-dimethyldiphenyl thioether; 4-hydroxybenzoic acid esters such as benzyl 4-hydroxybenzoate, ethyl 4-hydroxybenzoate, propyl 4-hydroxybenzoate, isopropyl 4-hydroxybenzoate, butyl 4-hydroxybenzoate, isobutyl 4-hydroxybenzoate, chlorobenzyl 4-hydroxybenzoate, methylbenzyl 4-hydroxybenzoate, and diphenylmethyl 4-hydroxybenzoate; metal salts of benzoic acid such as zinc benzoate and zinc 4-nitrobenzoate, salicylic acids such as 4-[2-(4-methoxyphenyloxy)ethyloxy]salicylic acid; metal salts of salicylic acid such as zinc salicylate and zinc bis[4-(octyloxycarbonylamino)-2-hydroxybenzoate]; hydroxysulfones such as 4,4'-dihydroxydiphenylsulfone, 2,4'-dihydroxydiphenylsulfone, 4-hydroxy-4'-methyldiphenylsulfone, 4-hydroxy-4'-isopropoxydiphenylsulfone, 4-hydroxy-4'-butoxydiphenylsulfone, 4,4'-dihydroxy-3,3'-diallyldiphenylsulfone, 3,4-dihydroxy-4'-methyldiphenylsulfone, 4,4'-dihydroxy-3,3',5,5'-tetrabromodiphenylsulfone, 4-allyloxy-4'-hydroxydiphenylsulfone, 2-(4-hydroxyphenylsulfonyl)phenol, 4,4'-sulfonylbis[2-(2-propenyl)]phenol, 4-[[4-(propoxy)phenyl}sulfonyl]phenol, 4-[{4-(allyloxy)phenyl}sulfonyl]phenol, 4-[{4-(benzyloxy)phenyl}sulfonyl]phenol, and 2,4-bis(phenylsulfonyl)-5-methyl-phenol; polyvalent metal salts of hydroxysulfones such as 4-phenylsulfonylphenoxy-zinc magnesium, -aluminum, and -titanium; 4-hydroxyphthalic acid diesters such as dimethyl 4-hydroxyphthalate, dicyclohexyl 4-hydroxyphthalate, and diphenyl 4-hydroxyphthalate; hydroxynaphthoic acid esters such as 2-hydroxy-6-carboxynaphthalene; trihalomethylsulfones such as tribromomethylphenylsulfone; sulfonylureas such as 4,4'-bis(p-toluenesulfonylaminocarbonylamino)diphenylmethane and N-(4-methylphenylsulfonyl)-N'-(3-(4-methylphenylsulfonyloxy)phenyl)urea; hydroxyacetophenone, p-phenylphenol, benzyl 4-hydroxyphenylacetate, p-benzylphenol, hydroquinone-monobenzyl ether, 2,4-dihydroxy-2'-methoxybenzanilide, tetracyanoquinodimethanes, N-(2-hydroxyphenyl)-2-[(4-hydroxyphenyl)thio]acetamide, N-(4-hydroxyphenyl)-2-[(4-hydroxyphenyl)thio]acetamide, 4-hydroxybenzenesulfonanilide, 4'-hydroxy-4-methylbenzenesulfonanilide, 4,4'-bis(4-methyl-3-phenoxycarbonyl)aminophenylureido))diphenylsulfone, 3-(3-phenylureido)benzenesulfonanilide, octadecylphosphoric acid, and dodecylphosphoric acid; and cross-linked diphenylsulfone compounds represented by the following formula or mixtures thereof:

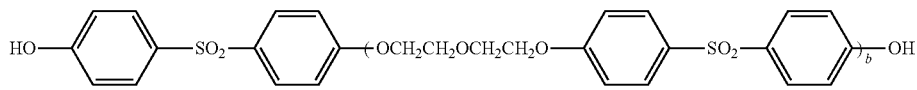

(b represents an integer of 0 to 6)

Among them, preferable examples thereof include 4-hydroxy-4'-isopropoxydiphenylsulfone and cross-linked diphenylsulfone compounds or mixtures thereof.

Examples of the image stabilizer can include: epoxy group-containing diphenylsulfones such as 4-benzyloxy-4'-(2-methylglycidyloxy)-diphenylsulfone and 4,4'-diglycidyloxydiphenylsulfone; 1,4-diglycidyloxybenzene, 4-[α-(hydroxymethyl)benzyloxy]-4'-hydroxydiphenylsulfone, 2-propanol derivatives, salicylic acid derivatives, metal salts (particularly, zinc salts) of oxynaphthoic acid derivatives, metal salts of 2,2-methylenebis(4,6-t-butylphenyl)phosphate, and other water-insoluble zinc compounds; hindered phenol compounds such as 2,2-bis(4'-hydroxy-3',5'-dibromophenyl)propane, 4,4'-sulfonylbis(2,6-dibromophenol), 4,4'-butylidene(6-t-butyl-3-methylphenol), 2,2'-methylene-bis(4-methyl-6-t-butylphenol), 2,2'-methylene-bis(4-ethyl-6-t-butylphenol), 2,2'-di-t-butyl-5,5'-dimethyl-4,4'-sulfonyl-diphenol, 1,1,3-tris(2-methyl-4-hydroxy-5-cyclohexylphenyl)butane, and 1,1,3-tris(2-methyl-4-hydroxy-5-t-butylphenyl)butane, and phenol novolac compounds, epoxy resins, and UU (color-developing agent manufactured by CHEMIPRO KASEI).

The examples further include a cross-linked diphenylsulfone compound represented by the following formula or a mixture thereof:

loxydiphenylsulfone; 2,4'-dihydroxydiphenylsulfone diethers such as 2,4'-dimethoxydiphenylsulfone, 2,4'-diethoxydiphenylsulfone, 2,4'-dipropoxydiphenylsulfone, 2,4'-diisopropoxydiphenylsulfone, 2,4'-dibutoxydiphenylsulfone, 2,4'-diisobutoxydiphenylsulfone, 2,4'-dipentyloxydiphenylsulfone, 2,4'-dihexyloxydiphenylsulfone, and 2,4'-diallyloxydiphenylsulfone;

1,2-bis(phenoxy)ethane, 1,2-bis(4-methylphenoxy)ethane, 1,2-bis(3-methylphenoxy)ethane, 1,2-bis(phenoxymethyl)benzene, 1,2-bis(4-methoxyphenylthio)ethane, 1,2-bis(4-methoxyphenoxy)propane, 1,3-phenoxy-2-propanol, 1,4-diphenylthio-2-butene, 1,4-diphenylthiobutane, 1,4-diphenoxy-2-butene, 1,5-bis(4-methoxyphenoxy)-3-oxapentane, 1,3-dibenzoyloxypropane, dibenzoyloxymethane, 4,4'-ethylenedioxy-bis-benzoic acid dibenzyl ester, bis[2-(4-methoxy-phenoxy)ethyl]ether, 2-naphthylbenzyl ether, 1,3-bis(2-vinyloxyethoxy)benzene, 1,4-diethoxynaphthalene, 1,4-dibenzyloxynaphthalene, 1,4-dimethoxynaphthalene, 1,4-bis(2-vinyloxyethoxy)benzene, p-(2-vinyloxyethoxy) biphenyl, p-aryloxybiphenyl, p-propargyloxybiphenyl, p-benzyloxybenzyl alcohol, 4-(m-methylphenoxymethyl)biphenyl, 4-methylphenyl-biphenyl ether, di-β-naphthylphenylenediamine, diphenylamine, carbazole, 2,3-di-m-tolylbutane, 4-benzylbiphenyl, 4,4'-dimethylbiphenyl, terphenyls such as m-terphenyl and p-terphenyl;

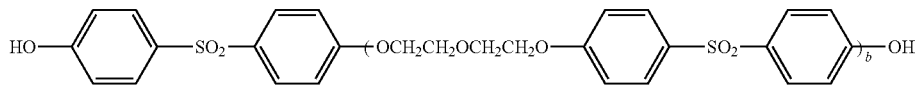

(b represents an integer of 0 to 6)

The image stabilizer is preferably a compound that is solid at room temperature, particularly preferably has a melting point of 60° C. or higher, and is poorly soluble in water.

Examples of the sensitizer can include: higher fatty acid amides such as stearic acid amide, stearic acid anilide, and palmitic acid amide; amides such as benzamide, acetoacetic acid anilide, thioacetanilide acrylic acid amide, ethylenebisamide, ortho-toluenesulfonamide, and para-toluenesulfonamide; phthalic acid diesters such as dimethyl phthalate, dibenzyl isophthalate, dimethyl isophthalate, dimethyl terephthalate, diethyl isophthalate, diphenyl isophthalate, and dibenzyl terephthalate; oxalic acid diesters such as dibenzyl oxalate, di(4-methylbenzyl)oxalate, di(4-chlorobenzyl)oxalate, a mixture of dibenzyl oxalate and di(4-chlorobenzyl)oxalate in equal amounts, and a mixture of di(4-chlorobenzyl)oxalate and di(4-methylbenzyl)oxalate in equal amounts; bis(t-butylphenols) such as 2,2'-methylenebis(4-methyl-6-t-butylphenol) and 4,4'-methylene-bis-2,6-di-t-butylphenol; 4,4'-dihydroxydiphenylsulfone diethers such as 4,4'-dimethoxydiphenylsulfone, 4,4'-diethoxydiphenylsulfone, 4,4'-dipropoxydiphenylsulfone, 4,4'-diisopropoxydiphenylsulfone, 4,4'-dibutoxydiphenylsulfone, 4,4'-diisobutoxydiphenylsulfone, 4,4'-dipentyloxydiphenylsulfone, 4,4'-dihexyloxydiphenylsulfone, and 4,4'-diallyl- 1,2-bis(3,4-dimethylphenyl)ethane, 2,3,5,6-tetramethyl-4'-methyldiphenylmethane, 4-acetylbiphenyl, dibenzoylmethane, triphenylmethane, phenyl 1-hydroxy-naphthoate, methyl 1-hydroxy-2-naphthoate, N-octadecylcarbamoyl-p-methoxycarbonylbenzene, benzyl p-benzyloxybenzoate, phenyl β-naphthoate, methyl p-nitrobenzoate, diphenylsulfone, carbonic acid derivatives such as diphenyl carbonate, guaiacol carbonate, di-p-tolyl carbonate, and phenyl-α-naphthyl carbonate;

1,1-diphenylpropanol, 1,1-diphenylethanol, N-octadecylcarbamoylbenzene, dibenzyl disulfide, stearic acid, Amide AP-1(7:3 mixture of stearic acid amide and palmitic acid amide), stearates such as aluminum stearate, calcium stearate, and zinc stearate; and zinc palmitate, behenic acid, zinc behenate, montanic acid wax, and polyethylene wax.

Preferable examples thereof can include 2-naphthylbenzyl ether, m-terphenyl, 4-benzylbiphenyl, benzyl oxalate, di(4-chlorobenzyl)oxalate, a mixture of benzyl oxalate and di(4-chlorobenzyl)oxalate in equal amounts, di(4-methylbenzyl)oxalate, a mixture of di(4-chlorobenzyl)oxalate and di(4-methylbenzyl)oxalate in equal amounts, phenyl 1-hydroxy-2-naphthoate, 1,2-bis(phenoxy)ethane, 1,2-bis(3- methylphenoxy)ethane, 1,2-bis(phenoxymethyl)benzene, dimethyl terephthalate, stearic acid amide, Amide AP-1(7:3 mixture of stearic acid amide and palmitic acid amide), diphenylsulfone, and 4-acetylbiphenyl.

More preferable examples thereof can include di(4-methylbenzyl)oxalate, 1,2-bis(3-methylphenoxy)ethane, 1,2-bis(phenoxymethyl)benzene, diphenylsulfone, and 2-naphthylbenzyl ether.

Examples of the filler can include silica, clay, kaolin, fired kaolin, talc, satin white, aluminum hydroxide, calcium carbonate, magnesium carbonate, zinc oxide, titanium oxide, barium sulfate, magnesium silicate, aluminum silicate, plastic pigments, diatomaceous earth, talc, and aluminum hydroxide. Among them, preferable examples thereof can include fired kaolin and calcium carbonate. The proportion of the filler used is 0.1 to 15 parts by mass, preferably 1 to 10 parts by mass, with respect to 1 part by mass of the color former. Moreover, these fillers may be mixed for use.

Examples of the dispersant can include: polyvinyl alcohols having various degrees of saponification and polymerization, such as polyvinyl alcohol, acetoacetylated polyvinyl alcohol, carboxy-modified polyvinyl alcohol, sulfonic acid-modified polyvinyl alcohol, amide-modified polyvinyl alcohol, and butyral-modified vinyl alcohol, cellulose derivatives such as methylcellulose, carboxymethylcellulose, hydroxyethylcellulose, ethylcellulose, acetylcellulose, and hydroxymethylcellulose, and sodium polyacrylate, polyacrylic acid ester, polyacrylamide, starch, sulfosuccinic acid esters such as dioctyl sodium sulfosuccinate, sodium dodecylbenzenesulfonate, a sodium salt of lauryl alcohol sulfonic acid ester, fatty acid salt, styrene-maleic anhydride copolymers, styrene-butadiene copolymers, polyvinyl chloride, polyvinyl acetate, polyacrylic acid ester, polyvinylbutyral, polyurethane, polystyrene and copolymers thereof, polyamide resins, silicone resins, petroleum resins, terpene resins, ketone resins, and coumarone resins.

The dispersant is used after being dissolved in a solvent such as water, alcohol, ketone, ester, or hydrocarbon. Alternatively, the dispersant may be used in a state emulsified in water or other solvents or in the form of paste dispersed therein.

Examples of the antioxidant can include 2,2'-methylenebis(4-methyl-6-t-butylphenol), 2,2'-methylenebis(4-ethyl-6-t-butylphenol), 4,4'-propylmethylenebis(3-methyl-6-t-butylphenol), 4,4'-butylidenebis(3-methyl-6-t-butylphenol), 4,4'-thiobis(2-t-butyl-5-methylphenol), 1,1,3-tris(2-methyl-4-hydroxy-5-t-butylphenyl)butane, 1,1,3-tris(2-methyl-4-hydroxy-5-cyclohexylphenyl)butane, 4-{4-[1,1-bis(4-hydroxyphenyl)ethyl]-α,α-dimethylbenzyl}phenol, 1,1,3-tris(2-methyl-4-hydroxy-5-cyclohexylphenyl)butane, 2,2'-methylenebis(6-tert-butyl-4-methylphenol), 2,2'-methylenebis(6-tert-butyl-4-ethylphenol), 4,4'-thiobis(6-tert-butyl-3-methylphenol), 1,3,5-tris[{4-(1,1-dimethylethyl)-3-hydroxy-2,6-dimethylphenyl}methyl]-1,3,5-triazine-2,4,6(1H,3H,5H)-trione, and 1,3,5-tris[{3,5-bis(1,1-dimethylethyl)-4-hydroxyphenyl}methyl]-1,3,5-triazine-2,4,6(1H,3H,5H)-trione.

Examples of the desensitizer can include aliphatic higher alcohols, polyethylene glycol, and guanidine derivatives.

Examples of the anti-tack agent can include stearic acid, zinc stearate, calcium stearate, carnauba wax, paraffin wax, and ester wax.

Examples of the antifoaming agent can include higher alcohol, fatty acid ester, oil, silicone, polyether, modified hydrocarbon, and paraffin antifoaming agents.

Examples of the light stabilizer can include: salicylic acid UV absorbers such as phenyl salicylate, p-t-butylphenyl salicylate, and p-octylphenyl salicylate; benzophenone UV absorbers such as 2,4-dihydroxybenzophenone, 2-hydroxy-4-methoxybenzophenone, 2-hydroxy-4-benzyloxybenzophenone, 2-hydroxy-4-octyloxybenzophenone, 2-hydroxy-4-dodecyloxybenzophenone, 2,2'-dihydroxy-4-methoxybenzophenone, 2,2'-dihydroxy-4,4'-dimethoxybenzophenone, 2-hydroxy-4-methoxy-5-sulfobenzophenone, and bis(2-methoxy-4-hydroxy-5-benzoylphenyl)methane; benzotriazole UV absorbers such as 2-(2'-hydroxy-5'-methylphenyl)benzotriazole, 2-(2'-hydroxy-5'-t-butylphenyl)benzotriazole, 2-(2'-hydroxy-3',5'-di-t-butylphenyl)benzotriazole, 2-(2'-hydroxy-3'-t-butyl-5'-methylphenyl)-5-chlorobenzotriazole, 2-(2'-hydroxy-3',5'-di-t-butylphenyl)-5-chlorobenzotriazole, 2-(2'-hydroxy-3',5'-di-t-amylphenyl)benzotriazole, 2-(2'-hydroxy-5'-tert-butylphenyl)benzotriazole, 2-(2'-hydroxy-5'-(1",1",3",3"-tetramethylbutyl)phenyl)benzotriazole, 2-[2'-hydroxy-3'-(3",4",5",6"-tetrahydrophthalimidomethyl)-5'-methylphenyl]benzotriazole, 2-(2'-hydroxy-5'-t-octylphenyl)benzotriazole, 2-[2'-hydroxy-3',5'-bis(α,α-dimethylbenzyl)phenyl]-2H-benzotriazole, 2-(2'-hydroxy-3'-dodecyl-5'-methylphenyl)benzotriazole, 2-(2'-hydroxy-3-undecyl-5'-methylphenyl)benzotriazole, 2-(2'hydroxy-3'-tridecyl-5'-methylphenyl)benzotriazole, 2-(2-hydroxy-3'-tetradecyl-5'-methylphenyl)benzotriazole, 2-(2'-hydroxy-3'-pentadecyl-5'-methylphenyl)benzotriazole, 2-(2'-hydroxy-3'-hexadecyl-5'-methylphenyl)benzotriazole, 2-[2'-hydroxy-4'-(2"-ethylhexyl)oxyphenyl]benzotriazole, 2-[2'-hydroxy-4'-(2"-ethylheptyl)oxyphenyl]benzotriazole, 2-[2'-hydroxy-4'-(2"-ethyloctyl)oxyphenyl]benzotriazole, 2-[2'-hydroxy-4'-(2"-propyloctyl)oxyphenyl]benzotriazole, 2-[2'-hydroxy-4'-(2"-propylheptyl)oxyphenyl]benzotriazole, 2-[2'-hydroxy-4'-(2"-propylhexyl)oxyphenyl]benzotriazole, 2-[2'-hydroxy-4'-(1"-ethylhexyl)oxyphenyl]benzotriazole, 2-[2'-hydroxy-4'-(1"-ethylheptyl)oxyphenyl]benzotriazole, 2-[2'-hydroxy-4'-(1'-ethyloctyl)oxyphenyl]benzotriazole, 2-[2'-hydroxy-4'-(1"-propyloctyl)oxyphenyl]benzotriazole, 2-[2'-hydroxy-4'-(1"-propylheptyl)oxyphenyl]benzotriazole, 2-[2'-hydroxy-4'-(1"-propylhexyl)oxyphenyl]benzotriazole, 2,2'-methylenebis[4-(1,1,3,3-tetramethylbutyl)-6-(2H-benzotriazol-2-yl)]phenol, and a condensate of polyethylene glycol and methyl-3-[3-t-butyl-5-(2H-benzotriazol-2-yl)-4-hydroxyphenyl]propionate; cyanoacrylate UV absorbers such as 2'-ethylhexyl-2-cyano-3,3-diphenylacrylate and ethyl-2-cyano-3,3-diphenylacrylate; hindered amine UV absorbers such as bis(2,2,6,6-tetramethyl-4-piperidyl)sebacate, succinic acid-bis(2,2,6,6-tetramethyl-4-piperidyl)ester, and 2-(3,5-di-t-butyl)malonic acid-bis(1,2,2,6,6-pentamethyl-4-piperidyl)ester; and 1, 8-dihydroxy-2-acetyl-3-methyl-6-methoxynaphthalene.

Examples of the fluorescent brightening agent can include 4,4'-bis[2-anilino-4-(2-hydroxyethyl)amino-1,3,5-triazinyl-6-amino]stilbene-2,2'-disulfonic acid disodium salt, 4,4'-bis[2-anilino-4-bis(hydroxyethyl)amino-1,3,5-triazinyl-6-amino]stilbene-2,2'-disulfonic acid disodium salt, 4,4'-bis[2-anilino-4-bis(hydroxypropyl)amino-1,3,5-triazinyl-6-amino]stilbene-2,2'-disulfonic acid disodium salt, 4,4'-bis[2-methoxy-4-(2-hydroxyethyl)amino-1,3,5-triazinyl-6-amino]stilbene-2,2'-disulfonic acid disodium salt, 4,4'-bis[2-methoxy-4-(2-hydroxypropyl)amino-1,3,5-triazinyl-6-amino]stilbene-2,2'-disulfonic acid disodium salt, 4,4'-bis[2-m-sulfoanilino-4-bis(hydroxyethyl)amino-1,3,5-triazinyl-6-amino]stilbene-2,2'-disulfonic acid disodium salt, 4-[2-p-sulfoanilino-4-bis(hydroxyethyl)amino-1,3,5-triazinyl-6- amino]-4'-[2-m-sulfoanilino-4-bis(hydroxyethyl)amino-1,3, 5-triazinyl-6-amino]stilbene-2,2'-disulfonic acid tetrasodium salt, 4,4'-bis[2-p-sulfoanilino-4-bis(hydroxyethyl)amino-1,3,5-triazinyl-6-amino]stilbene-2,2'-disulfonic acid tetrasodium salt, 4,4'-bis[2-(2,5-disulfoanilino)-4-phenoxyamino-1,3,5-triazinyl-6-amino]stilbene-2,2'-disulfonic acid hexasodium salt, 4,4'-bis[2-(2,5-disulfoanilino)-4-(p-methoxycarbonylphenoxy)amino-1,3,5-triazinyl-6-amino]stilbene-2,2'-disulfonic acid hexasodium salt, 4,4'-bis[2-(p-sulfophenoxy)-4-bis(hydroxyethyl)amino-1,3,5-triazinyl-6-amino]stilbene-2,2'-disulfonic acid hexasodium salt, 4,4'-bis[2-(2,5-disulfoanilino)-4-formalinylamino-1,3,5-triazinyl-6-amino]stilbene-2,2'-disulfonic acid hexasodium salt, and 4,4'-bis[2-(2,5-disulfoanilino)-4-bis(hydroxyethyl)amino-1,3,5-triazinyl-6-amino]stilbene-2,2'-disulfonic acid hexasodium salt.

(Method for Producing Recording Material)

When the present invention is used in thermal recording paper, it may be used in the same way as a known use method. For example, the thermal recording paper can be produced by separately dispersing fine particles of the compound of the present invention and fine particles of a color former in aqueous solutions of water-soluble binders such as polyvinyl alcohol or cellulose, mixing these suspension solutions, applying the mixture to a support such as paper, and drying it.

When the present invention is used in pressure-sensitive copying paper, it can be produced in the same way as in use of a known color-developing agent or sensitizer. For example, a color former microencapsulated by a method known in the art is dispersed in an appropriate dispersant and applied to paper to prepare a sheet of the color former. Moreover, a dispersion solution of a color-developing agent is applied to paper to prepare a sheet of the color-developing agent. Both the sheets thus prepared are combined to prepare pressure-sensitive copying paper. The pressure-sensitive copying paper may be a unit consisting of: upper paper carrying a microcapsule containing a solution of a color former in an organic solvent, wherein the microcapsule is applied on the underside of the upper paper; and lower paper carrying a color-developing agent (acidic substance) applied on the top surface of the lower paper. Alternatively, the pressure-sensitive copying paper may be so-called self-contained paper comprising the microcapsule and the color-developing agent applied on the same paper surface.

Those conventionally known are used as the color-developing agent used in the production or the color-developing agent mixed with the compound of the present invention for use. Examples thereof can include: inorganic acidic substances such as Japanese acid clay, activated clay, attapulgite, bentonite, colloidal silica, aluminum silicate, magnesium silicate, zinc silicate, tin silicate, fired kaolin, and talc; aliphatic carboxylic acids such as oxalic acid, maleic acid, tartaric acid, citric acid, succinic acid, and stearic acid; aromatic carboxylic acids such as benzoic acid, p-t-butylbenzoic acid, phthalic acid, gallic acid, salicylic acid, 3-isopropylsalicylic acid, 3-phenylsalicylic acid, 3-cyclohexylsalicylic acid, 3,5-di-t-butylsalicylic acid, 3-methyl-5-benzylsalicylic acid, 3-phenyl-5-(2,2-dimethylbenzyl)salicylic acid, 3,5-di-(2-methylbenzyl)salicylic acid, and 2-hydroxy-1-benzyl-3-naphthoic acid, and metal (e.g., zinc, magnesium, aluminum, and titanium) salts of these aromatic carboxylic acids; phenol resin color-developing agents such as p-phenylphenol-formalin resins and p-butylphenol-acetylene resins, and mixtures of these phenol resin color-developing agents and the metal salts of the aromatic Paper, synthetic paper, a film, a plastic film, a foamed plastic film, nonwoven cloth, recycled paper (e.g., recycled paper pulps), or the like, conventionally known can be used as the support used in the present invention. Moreover, the combination thereof can also be used as the support.

If paper is used as the support, a dispersion solution containing a dispersion solution of a color former, a dispersion solution of a color-developing agent, and a dispersion solution of a filler can be directly applied to the paper, or the dispersion solution can be applied after applying a dispersion solution for an undercoat layer to the paper and drying it. Preferably, the dispersion solution for the undercoat layer is applied before applying the dispersion solution because better color-developing sensitivity is thus attained.

The dispersion solution for the undercoat layer is used for improving the smoothness on the surface of the support and is not particularly limited, but preferably contains a filler, a dispersant and water, and specifically, fired kaolin or calcium carbonate is preferred as the filler, and polyvinyl alcohol is preferred as the dispersant.

Examples of methods for forming a recording material layer on the support include a method comprising applying a dispersion solution containing a dispersion solution of a color former, a dispersion solution of a color-developing agent, and a dispersion solution of a filler to a support, followed by drying, a method comprising spraying such a dispersion solution onto a support with a spray or the like, followed by drying, and a method comprising dipping a support in such a dispersion solution for a given time, followed by drying. Moreover, examples of the application method include hand coating, a size press coater method, a roll coater method, an air knife coater method, a blend coater method, a flow coater method, a curtain coater method, a comma direct method, a gravure direct method, a gravure reverse method, and a reverse roll coater method.

EXAMPLES

Hereinafter, a recording material of the present invention is described in detail with reference to Examples. However, the present invention is not necessarily limited to them.

Incidentally, Ansilex®-93 was used as the fired kaolin. It is noted that the following abbreviations are used for compounds of the following structures:

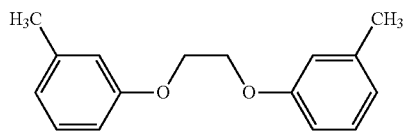

Abbreviation: EGMTE

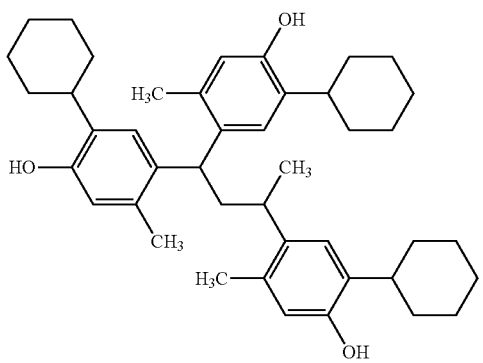

Abbreviation: DH-43

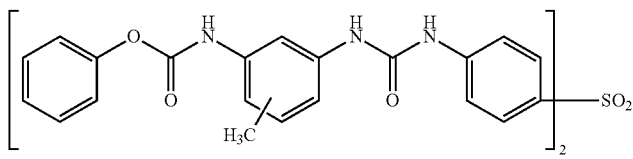

Abbreviation: UU

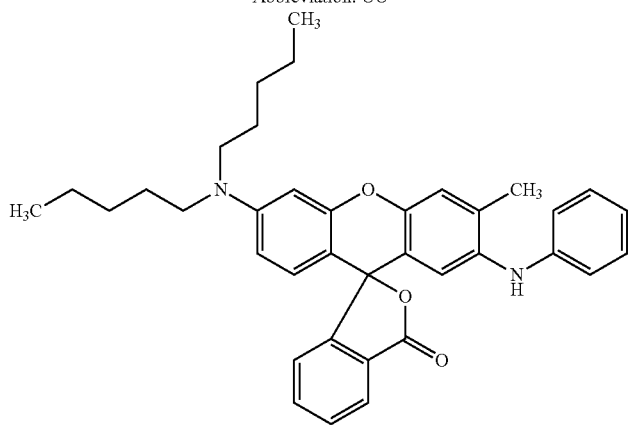

Abbreviation: Black-305

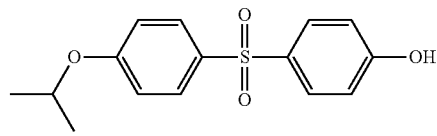

Abbreviation: D-8
(manufactured by Nippon Soda Co., Ltd.)

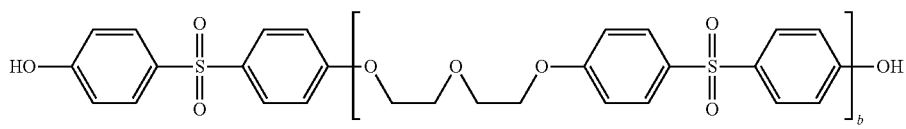

($b$ represents an integer of 0 to 6)
Cross-linked diphenylsulfone compounds or mixtures thereof
Abbreviation: D-90 (manufactured by Nippon Soda Co., Ltd.)

(1) Synthesis of benzenesulfonamide Compounds

Example 1

Synthesis of 4-methyl-N-(2-(3-phenylureido)phenyl) benzenesulfonamide (Compound No. 4 in Table 1)

To 200 ml of ethyl acetate, 10.8 g (0.1 mol) of o-phenylenediamine (manufactured by Tokyo Chemical Industry Co., Ltd., purity 98%) was added, and the resultant was cooled to 5° C. To this solution, 11.9 g (0.1 mol) of phenyl isocyanate (manufactured by Wako Pure Chemical Industries, Ltd., purity 98%) was added dropwise while preventing the temperature from increasing to 10° C. or more. After the completion of the dropwise addition, a reaction was performed at room temperature for 30 minutes. After the completion of the reaction, crystals deposited during the reaction were filtered off to obtain 1-(2-aminophenyl)-3-phenylurea as white crystals (22.1 g, yield 99% with respect to o-phenylenediamine).

To 200 ml of ethyl acetate, 22.1 g of the 1-(2-aminophenyl)-3-phenylurea and 7.9 g (0.1 mol) of pyridine were added. After adding 19.1 g (0.1 mol) of p-toluenesulfonyl chloride (manufactured by Wako Pure Chemical Industries, Ltd., purity 97%) to this solution in small aliquots at room temperature, a reaction was performed at 40° C. for 2 hours. After the completion of the reaction, the reaction solution was washed with 200 ml of water, and then, an aqueous layer was removed by a separation operation. Substances not dissolved in an organic layer were removed by suction filtration, and the solvent was distilled off under reduced pressure. To the residue, 500 ml of methanol was added to reflux once for dissolving impurities, and then, the solvent was distilled off until crystals were deposited. The deposited crystals were filtered off and vacuum dried to obtain the title compound as white crystals (27.4 g, yield 71% with respect to o-phenylenediamine). Melting point: 171-173° C.

$^1$H-NMR (d$_6$-DMSO): δ 2.32 (3H), 6.49 (1H), 6.78 (1H), 6.98 (1H), 7.16 (1H), 7.28-7.35 (4H), 7.46 (2H), 7.56 (2H), 7.96 (1H), 8.25 (1H), 9.45 (1H), 9.48 (1H).

Example 2

Synthesis of 3-methyl-N-(2-(3-phenylureido)phenyl)benzenesulfonamide (Compound No. 3 in Table 1)

To 87 ml of ethyl acetate, 1.2 g (5 mmol) of 1-(2-aminophenyl)-3-phenylurea synthesized in the same manner as in Example 1 and 0.9 g (9 mmol) of triethylamine were added. To this solution, 1.7 g (9 mmol) of m-toluenesulfonyl chloride (manufactured by Wako Pure Chemical Industries, Ltd., purity 97%) was added dropwise at room temperature. After refluxing for 4 hours, the reaction solution was washed with 2N hydrochloric acid. After removing an aqueous layer, the solvent was distilled off under reduced pressure. To the residue, 20 ml of ethanol was added to deposit crystals. The crystals were filtered off and vacuum dried to obtain the title compound as white crystals (2.42 g, yield 73% with respect to o-phenylenediamine). Melting point: 161-164° C.

$^1$H-NMR (d$_6$-DMSO): δ 2.33 (3H), 6.48 (1H), 6.79 (1H), 6.98 (1H), 7.17 (1H), 7.30 (2H), 7.43-7.49 (5H), 7.54 (1H), 8.00-8.02 (1H), 8.28 (1H), 9.50 (2H).

Example 3

Synthesis of 2-methyl-N-(2-(3-phenylureido)phenyl)benzenesulfonamide (Compound No. 2 in Table 1)

To 170 ml of ethyl acetate, 3.9 g (15 mmol) of 1-(2-aminophenyl)-3-phenylurea synthesized in the same manner as in Example 1 and 1.8 g (18 mmol) of triethylamine were added. To this solution, 3.3 g (8.5 mmol) of o-toluenesulfonyl chloride (manufactured by Wako Pure Chemical Industries, Ltd., purity 95%) was added dropwise at room temperature. After refluxing for 4 hours, the reaction solution was washed with 2N hydrochloric acid. After removing an aqueous layer, the solvent was distilled off under reduced pressure, and to the residue, 20 ml of ethanol was added to deposit crystals. The crystals were filtered off and vacuum dried to obtain the title compound as white crystals (2.8 g, yield 43%). Melting point: 147-150° C.

$^1$H-NMR (d$_5$-DMSO): δ 2.52 (3H), 6.38 (1H), 6.75 (1H), 6.99 (1H), 7.16 (1H), 7.29-7.32 (3H), 7.40-7.42 (1H), 7.48-7.53 (3H), 7.65 (1H), 7.98 (1H), 8.34 (1H), 9.47 (1H), 9.55 (1H).

Example 4

Synthesis of N-(2-(3-phenylureido)phenyl)benzenesulfonamide (Compound No. 1 in Table 1)

To 150 ml of ethyl acetate, 3.4 g (13 mmol) of 1-(2-aminophenyl)-3-phenylurea synthesized in the same manner as in Example 1 and 1.5 g (15 mmol) of triethylamine were added. To this solution, 2.7 g (15 mmol) of benzenesulfonyl chloride (manufactured by Tokyo Chemical Industry Co., Ltd., purity 99%) was added dropwise at room temperature. After refluxing for 4 hours, the reaction solution was washed with 2N hydrochloric acid. After removing an aqueous layer, the solvent was distilled off under reduced pressure, and to the residue, 20 ml of ethanol was added to deposit crystals. The crystals were filtered off and vacuum dried to obtain the title compound as white crystals (3.6 g, yield 65% with respect to o-phenylenediamine). Melting point: 155-157° C.

$^1$H-NMR (d$_6$-DMSO): δ 6.41 (1H), 6.75 (1H), 6.97 (1H), 7.16 (1H), 7.29 (2H), 7.46-7.48 (2H), 7.54-7.57 (2H), 7.63-7.65 (1H), 7.68-7.70 (2H), 8.00-8.02 (1H), 8.28 (1H), 9.51 (1H), 9.54 (1H).

Example 4-2

Another Method for Synthesizing N-(2-(3-phenylureido)phenyl)benzenesulfonamide (Compound No. 1 in Table 1)

To a mixed solvent of 10 ml of ethyl acetate and 70 ml of water, 10.8 g (0.1 mol) of o-phenylenediamine (manufactured by Tokyo Chemical Industry Co., Ltd., purity 98%) and 5.8 g (0.055 mol) of sodium carbonate were added, and after nitrogen purge, the resultant was cooled to an internal temperature of 20° C. To this solution, 17.7 g (0.1 mol) of benzenesulfonyl chloride was added dropwise while preventing the internal temperature from increasing beyond 20° C. After increasing the temperature to 50° C., a reaction was performed at that temperature for 2 hours. After the completion of the reaction, the solution was cooled to 20° C., crystals were filtered off by the suction filtration, and the crystals were washed with distilled water and ethyl acetate until the filtrate became colorless to obtain N-(2-aminophenyl)benzenesulfonamide as pale yellow crystals.

The N-(2-aminophenyl)benzenesulfonamide was returned to the reaction vessel, and after adding 50 ml of ethyl acetate thereto, azeotropic dehydration was performed. After cooling the reaction solution to 50° C., 11.9 g of phenyl isocyanate was added dropwise thereto, and a reaction was performed at that temperature for 1 hour. After the completion of the reaction, 50 ml of an aliphatic hydrocarbon solvent was added thereto, the resultant was cooled to 5° C., and then crystals were filtered off by the suction filtration. The crystals were vacuum dried to obtain the title compound as white crystals (35.0 g, yield 95% with respect to o-phenylenediamine). Melting point: 155-157° C.

Example 5

Synthesis of 4-chloro-N-(2-(3-phenylureido)phenyl)benzenesulfonamide (Compound No. 10 in Table 1)

To 150 ml of ethyl acetate, 3.4 g (13 mmol) of 1-(2-aminophenyl)-3-phenylurea synthesized in the same manner as in Example 1 and 1.5 g (15 mmol) of triethylamine were added. To this solution, 3.2 g (15 mmol) of 4-chlorophenylsulfonyl chloride (manufactured by Wako Pure Chemical Industries, Ltd., purity 95%) was added dropwise at room temperature. After refluxing for 4 hours, the reaction solution was washed with 2N hydrochloric acid. After removing an aqueous layer, the solvent was distilled off under reduced pressure, and to the residue, 20 ml of ethanol was added to deposit crystals. The crystals were filtered off and vacuum dried to obtain the title compound as white crystals (5.2 g, yield 86% with respect to o-phenylenediamine). Melting point: 163-165° C.

$^1$H-NMR (d$_6$-DMSO): δ 6.50 (1H), 6.82 (1H), 6.99 (1H), 7.19 (1H), 7.30 (2H), 7.47 (2H), 7.63-7.69 (4H), 8.01-8.03 (1H), 8.28 (1H), 9.47 (1H), 9.65 (1H).

Example 6

Synthesis of 4-methyl-N-(3-(3-phenylureido)phenyl)benzenesulfonamide (Compound No. 14 in Table 1)

4.3 g (40 mmol) of m-phenylenediamine (manufactured by Tokyo Chemical Industry Co., Ltd., purity 98%) was dissolved in 75 ml of dichloromethane, and the resultant was stirred at an internal temperature of 10° C. or less. To this solution, 4.8 g (40 mmol) of phenyl isocyanate was added dropwise at 10° C. or less, and a reaction was performed at room temperature for 2 hours. After the completion of the reaction, an insoluble substance was filtered off, and the filtrate was concentrated under reduced pressure to obtain 1-(3-aminophenyl)-3-phenylurea of interest as pale yellow crystals (7.8 g, yield 86% with respect to m-phenylenediamine).

To 160 ml of ethyl acetate, 3.8 g (17 mmol) of the 1-(3-aminophenyl)-3-phenylurea and 1.7 g (17 mmol) of triethylamine were added. To this solution, 3.2 g (17 mmol) of p-toluenesulfonyl chloride was added in small aliquots at room temperature. After refluxing for 5 hours, the reaction solution was washed with 2N hydrochloric acid. After removing an aqueous layer, the solvent was distilled off under reduced pressure, and to the residue, 20 ml of ethanol was added to deposit crystals. The crystals were filtered off and vacuum dried to obtain the title compound as white crystals (2.7 g, yield 43% with respect to m-phenylenediamine). Melting point: 196-198° C.

$^1$H-NMR (d$_6$-DMSO): δ 2.33 (3H), 6.68-6.70 (1H), 6.97-6.99 (1H), 7.09-7.12 (2H), 7.26-7.29 (3H), 7.34-7.36 (2H), 7.42-7.44 (2H), 7.66-7.68 (2H), 8.55 (1H), 8.69 (1H), 10.2 (1H).

Example 7

Synthesis of 3-methyl-N-(3-(3-phenylureido)phenyl)benzenesulfonamide (Compound No. 13 in Table 1)

To 90 ml of ethyl acetate, 2.0 g (9 mmol) of 1-(3-aminophenyl)-3-phenylurea synthesized in the same manner as in Example 6 and 0.88 g (9 mmol) of triethylamine were added. To this solution, 1.7 g (9 mmol) of m-toluenesulfonyl chloride was added dropwise at room temperature. After refluxing for 4 hours, the reaction solution was washed with 2N hydrochloric acid. After removing an aqueous layer, the solvent was distilled off under reduced pressure, and to the residue, 20 ml of ethanol was added to deposit crystals. The crystals were filtered off and vacuum dried to obtain the title compound as white crystals (2.0 g, yield 60% with respect to m-phenylenediamine). Melting point: 190-191° C.

$^1$H-NMR (d$_6$-DMSO): δ 2.35 (3H), 6.69-6.70 (1H), 6.97 (1H), 7.10-7.11 (2H), 7.28 (2H), 7.32 (1H), 7.42-7.44 (4H), 7.57-7.59 (1H), 7.64 (1H), 8.56 (1H), 8.70 (1H), 10.2 (1H).

Example 8

Synthesis of 2-methyl-N-(3-(3-phenylureido)phenyl)benzenesulfonamide (Compound No. 12 in Table 1)

To 120 ml of ethyl acetate, 2.7 g (12 mmol) of 1-(3-aminophenyl)-3-phenylurea synthesized in the same manner as in Example 6 and 1.2 g (12 mmol) of triethylamine were added. To this solution, 2.3 g (12 mmol) of o-toluenesulfonyl chloride was added dropwise at room temperature. After refluxing for 4 hours, the reaction solution was washed with 2N hydrochloric acid. After removing an aqueous layer, the solvent was distilled off under reduced pressure, and to the residue, 20 ml of ethanol was added to deposit crystals. The crystals were filtered off and vacuum dried to obtain the title compound as white crystals (3.6 g, yield 78% with respect to m-phenylenediamine). Melting point: 197-199° C.

$^1$H-NMR (d$_6$-DMSO): δ 2.60 (3H), 6.67-6.68 (1H), 6.95-6.98 (1H), 7.07-7.09 (2H), 7.25-7.29 (3H), 7.34-7.38 (2H), 7.41-7.43 (2H), 7.47-7.51 (1H), 7.89 (1H), 8.54 (1H), 8.67 (1H), 10.4 (1H).

Example 9

Synthesis of N-(3-(3-phenylureido)phenyl)benzenesulfonamide (Compound No. 11 in Table 1)

To 130 ml of ethyl acetate, 3.0 g (13 mmol) of 1-(3-aminophenyl)-3-phenylurea synthesized in the same manner as in Example 6 and 1.3 g (13 mmol) of triethylamine were added. To this solution, 2.3 g (13 mmol) of benzenesulfonyl chloride was added dropwise at room temperature. After refluxing for 4 hours, the reaction solution was washed with 2N hydrochloric acid. After removing an aqueous layer, the solvent was distilled off under reduced pressure, and to the residue, 20 ml of ethanol was added to deposit crystals. The crystals were filtered off and vacuum dried to obtain the title compound as pale yellow crystals (2.4 g, yield 49% with respect to m-phenylenediamine). Melting point: 195-197° C.

$^1$H-NMR (d$_6$-DMSO): δ 6.68-6.70 (1H), 6.97 (1H), 7.09-7.12 (2H), 7.25-7.29 (3H), 7.41-7.43 (2H), 7.54-7.61 (3H), 7.78-7.80 (2H), 8.55 (1H), 8.70 (1H), 10.3 (1H).

Example 10

Synthesis of 4-methyl-N-(4-(3-phenylureido)phenyl)benzenesulfonamide (Compound No. 21 in Table 1)

4.3 g (40 mmol) of p-phenylenediamine (manufactured by Tokyo Chemical Industry Co., Ltd., purity 97%) was dissolved in 80 ml of dichloromethane, and the resultant was stirred at an internal temperature of 10° C. or less. To this solution, 4.8 g (40 mmol) of phenyl isocyanate was added dropwise at 10° C. or less, and a reaction was performed at room temperature for 1 hour. After the completion of the reaction, an insoluble substance was filtered off, and the filtrate was dried under reduced pressure to obtain 1-(4-aminophenyl)-3-phenylurea of interest as white crystals (8.7 g, yield 96% with respect to p-phenylenediamine).

To 200 ml of ethyl acetate, 2.0 g (9 mmol) of the 1-(4-aminophenyl)-3-phenylurea and 7.9 g (9 mmol) of pyridine were added, and to this solution, 6.0 g (30 mmol) of p-toluenesulfonyl chloride (manufactured by Wako Pure Chemical Industries, Ltd., purity 97%) was added in small aliquots at room temperature. After performing a reaction for 2 hours, deposited crystals were filtered off and dissolved in 50 ml of acetone. After adding 1.0 g of activated carbon thereto and heating the resultant to 40° C., the activated carbon was removed by Celite filtration. The solvent was distilled off under reduced pressure, and the resultant was vacuum dried to obtain the title compound as white crystals (2.5 g, yield 68% with respect to p-phenylenediamine). Melting point: 204-206° C.

$^1$H-NMR (d$_6$-DMSO): δ 2.33 (3H), 6.93-6.98 (3H), 7.24-7.30 (4H), 7.33 (2H), 7.41 (2H), 7.59(2H), 8.56 (1H), 8.59 (1H), 9.92 (1H).

Example 11

Synthesis of 3-methyl-N-(4-(3-phenylureido)phenyl)benzenesulfonamide (Compound No. 20 in Table 1)

To 90 ml of ethyl acetate, 2.0 g (9 mmol) of 1-(4-aminophenyl)-3-phenylurea synthesized in the same manner as in Example 10 and 0.88 g (9 mmol) of triethylamine were added. To this solution, 1.7 g (9 mmol) of m-toluenesulfonyl chloride was added dropwise at room temperature. After refluxing for 4 hours, the reaction solution was washed with 2N hydrochloric acid. After removing an aqueous layer, the solvent was distilled off under reduced pressure, and to the residue, 20 ml of ethanol was added to deposit crystals. The crystals were filtered off and vacuum dried to obtain the title compound as white crystals (2.1 g, yield 63% with respect to p-phenylenediamine). Melting point: 183-185° C.

$^1$H-NMR (d$_6$-DMSO): δ 2.34 (3H), 6.95-6.99 (3H), 7.24-7.31 (4H), 7.40-7.42 (4H), 7.50 (1H), 7.55 (1H), 8.57 (1H), 8.60 (1H), 9.97 (1H).

Example 12

Synthesis of 2-methyl-N-(4-(3-phenylureido)phenyl)benzenesulfonamide (Compound No. 19 in Table 1)

To 100 ml of ethyl acetate, 2.3 g (10 mmol) of 1-(4-aminophenyl)-3-phenylurea synthesized in the same manner as in Example 10 and 1.0 g (10 mmol) of triethylamine were added. To this solution, 1.9 g (10 mmol) of o-toluenesulfonyl chloride was added dropwise at room temperature. After refluxing for 4 hours, the reaction solution was washed with 2N hydrochloric acid. After removing an aqueous layer, the solvent was distilled off under reduced pressure, and to the residue, 20 ml of ethanol was added to deposit crystals. The crystals were filtered off and vacuum dried to obtain the title compound as white crystals (3.2 g, yield 84% with respect to p-phenylenediamine). Melting point: 169-172° C.

$^1$H-NMR (d$_6$-DMSO): δ 2.50 (3H), 6.93-6.98 (3H), 7.23-7.41 (8H), 7.46-7.48 (1H), 7.80-7.81 (1H), 8.54 (1H), 8.59 (1H), 10.1 (1H).

Example 13

Synthesis of N-(4-(3-phenylureido)phenyl)benzenesulfonamide (Compound No. 18 in Table 1)

To 40 ml of ethyl acetate, 4.6 g (20 mmol) of 1-(4-aminophenyl)-3-phenylurea synthesized in the same manner as in Example 10 and 1.6 g (20 mmol) of pyridine were added, followed by stirring. To this solution, 3.6 g (20 mmol) of benzenesulfonyl chloride (manufactured by Tokyo Chemical Industry Co., Ltd., purity 99%) was added dropwise at room temperature. After performing a reaction for 2 hours, the reaction solution was washed with 40 ml of water, and an aqueous layer was removed by separation. After the solvent was distilled off from an organic layer under reduced pressure, the residue was dissolved in acetone, and activated carbon was added thereto, followed by stirring. After removing the activated carbon by Celite filtration, the solvent was distilled off. To the residue, ethyl acetate/n-hexane was added, and the thus deposited crystals were filtered off and vacuum dried to obtain the title compound as white crystals (6.7 g, yield 82% with respect to p-phenylenediamine). Melting point: 180-182° C.

$^1$H-NMR (d$_6$-DMSO): δ 6.93-6.99 (3H), 7.24-7.31 (4H), 7.41 (2H), 7.54 (2H), 7.60 (1H), 7.71 (2H), 8.57 (1H), 8.59 (1H), 10.01 (1H).

Example 14

Synthesis of 4-methyl-N-(4-methyl-3-(3-phenylureido)phenyl)benzenesulfonamide (Compound No. 35 in Table 1)

To 100 ml of ethyl acetate, 4.9 g (40 mmol) of 2,4-diaminotoluene (manufactured by Wako Pure Chemical Industries, Ltd., purity 95%) and 4.0 g (40 mmol) of triethylamine were added. To this solution, 7.6 g (40 mmol) of p-toluenesulfonyl chloride was added in small aliquots, and a reaction was performed at room temperature for 4 hours. After the completion of the reaction, deposited crystals were filtered off to obtain 12.5 g of N-(3-amino-4-methylphenyl)-4-methylbenzenesulfonamide as beige crystals.

6.5 g (24 mmol) of the N-(3-amino-4-methylphenyl)-4-methylbenzenesulfonamide was dissolved in chloroform, and the resultant was cooled to 10° C. or less. To this solution, 2.8 g (24 mmol) of phenyl isocyanate was added dropwise at 10° C. or less, and then the resultant was heated to room temperature to perform a reaction for 4 hours. After the completion of the reaction, 2N hydrochloric acid was added thereto to adjust an aqueous layer to be acid, and to extract it with chloroform. After distilling off the solvent, the residue was purified by silica gel column chromatography to obtain the title compound as white crystals (3.6 g, yield 45% with respect to N-(3-amino-4-methylphenyl)-4-methylbenzenesulfonamide). Melting point: 173-175° C.

$^1$H-NMR (d$_6$-DMSO): δ 2.11 (3H), 2.32 (3H), 6.70 (1H), 6.97-6.99 (2H), 7.29-7.34 (4H), 7.45 (2H), 7.66 (2H), 7.78 (1H), 7.84 (1H), 9.01 (1H), 10.0 (1H).

Example 15

Synthesis of 4-methyl-N-(2-methyl-5-(3-phenylureido)phenyl)benzenesulfonamide (Compound No. 28 in Table 1)

6.1 g (50 mmol) of 2,4-diaminotoluene was dissolved in 250 ml of ethyl acetate, and the resultant was cooled to 10° C. or less. To this solution, 3.0 g (25 mmol) of phenyl isocyanate was added dropwise at 10° C. or less, and a reaction was performed at room temperature for 3 hours. After filtering off deposited crystals, the crystals were dissolved in 150 ml of acetone. An insoluble substance was filtered off, and the solvent was distilled off from the filtrate to obtain 1-(3-amino-4-methylphenyl)-3-phenylurea of interest as pale brown crystals (3.0 g).

To 200 ml of ethyl acetate, 3.0 g (13 mmol) of the 1-(3-amino-4-methylphenyl)-3-phenylurea and 1.3 g (13 mmol) of triethylamine were added. To this solution, 2.4 g (13 mmol) of p-toluenesulfonyl chloride was added in small aliquots at room temperature, and then a reaction was performed at 60° C. for 6 hours. After the completion of the reaction, deposited crystals were filtered off and vacuum dried to obtain the title compound as white crystals (2.6 g, yield 53% with respect to 1-(3-amino-4-methylphenyl)-3-phenylurea). Melting point: 206-207° C.

$^1$H-NMR (d$_6$-DMSO): δ 1.87 (3H), 2.36 (3H), 6.96-7.00 (2H), 7.18 (1H), 7.24-7.29 (3H), 7.35 (2H), 7.42 (2H), 7.56 (2H), 8.53 (1H), 8.61 (1H), 9.45 (1H).

Example 16

Synthesis of N-(2-(3-(4-methoxyphenyl)ureido)phenyl)-4-methylbenzenesulfonamide (Compound No. 252 in Table 1)

To 40 ml of ethyl acetate, 2.2 g (20 mmol) of o-phenylenediamine was added, and the resultant was cooled to 5° C. To this solution, 3.0 g (20 mmol) of 4-methoxyphenyl isocyanate (manufactured by Wako Pure Chemical Industries, Ltd., purity 97%) was added dropwise at 10° C. or less, and then a reaction was performed at room temperature for 30 minutes. Subsequently, after adding 2.0 g (20 mmol) of triethylamine thereto, 19.1 g (100 mmol) of p-toluenesulfonyl chloride was added in small aliquots at room temperature, and a reaction was performed at 40° C. for 2 hours. After the completion of the reaction, the reaction solution was washed with water, the solvent was then distilled off, and the residue was vacuum dried to obtain the title compound as white crystals (4.5 g, yield 55% with respect to o-phenylenediamine). Melting point: 97-108° C.

$^1$H-NMR ($d_6$-DMSO): δ 2.35 (3H), 3.73 (3H), 6.48 (1H), 6.77 (1H), 6.89 (2H), 7.15 (1H), 7.35 (2H), 7.38 (2H), 7.57 (2H), 7.99 (1H), 8.18 (1H), 9.30 (1H), 9.46 (1H).

Example 17

Synthesis of N-(2-(3-(4-fluorophenyl)ureido)phenyl)-4-methylbenzenesulfonamide (Compound No. 287 in Table 1)

To 10 ml of acetonitrile, 0.8 g (7.3 mmol) of o-phenylenediamine was added, and to this solution, a solution of 1.0 g (7.3 mmol) of 4-fluorophenyl isocyanate (manufactured by Tokyo Chemical Industry Co., Ltd., purity 98%) in 5 ml of acetonitrile was added dropwise at room temperature, and then a reaction was performed for 1.5 hours. After the completion of the reaction, deposited crystals were filtered off and vacuum dried to obtain 1-(2-aminophenyl)-3-(4-fluorophenyl)urea as white crystals (1.5 g).

To 10 ml of ethyl acetate, 1.5 g (6 mmol) of the 1-(2-aminophenyl)-3-(4-fluorophenyl)urea and 0.6 g (7.5 mmol) of pyridine were added, and to this solution, a solution of 1.4 g (7.3 mmol) of p-toluenesulfonyl chloride in 10 ml of ethyl acetate was added dropwise at room temperature, and then a reaction was performed at 60° C. for 2 hours. After the completion of the reaction, the reaction solution was washed with water and the solvent was distilled off. To the residue, 20 ml of methanol and 10 ml of water were added, and the resultant was heated to 60° C. once and then cooled to 5° C. to deposit crystals. The deposited crystals were filtered off and vacuum dried to obtain the title compound as white crystals (2.2 g, yield 75% with respect to o-phenylenediamine). Melting point: 149-153° C.

$^1$H-NMR ($d_6$-DMSO): δ 2.32 (3H), 6.48 (1H), 6.80 (1H), 7.17 (1H), 7.33 (2H), 7.56 (2H), 7.63-7.68 (4H), 7.98 (1H), 8.33 (1H), 9.48 (1H), 9.88 (1H).

Example 18

Synthesis of 4-methyl-N-(2-(3-(4-trifluoromethyl)phenyl)ureido)phenyl)benzenesulfonamide (Compound No. 322 in Table 1)

To 10 ml of acetonitrile, 0.6 g (5.3 mmol) of o-phenylenediamine was added, and to this solution, a solution of 1.0 g (5.3 mmol) of 4-(trifluoromethyl)phenyl isocyanate (manufactured by Tokyo Chemical Industry Co., Ltd., purity 98%) in 5 ml of acetonitrile was added dropwise at room temperature, and then a reaction was performed at room temperature for 1.5 hours. After the completion of the reaction, deposited crystals were filtered off and vacuum dried to obtain 1-(2-aminophenyl)-3-(4-(trifluoromethyl)phenyl)urea as white crystals (1.4 g).

To 10 ml of ethyl acetate, 1.4 g (4.7 mmol) of the 1-(2-aminophenyl)-3-(4-(trifluoromethylphenyl)urea and 0.4 g (5 mmol) of pyridine were added. To this solution, a solution of 1.0 g (5.2 mmol) of p-toluenesulfonyl chloride in 5 ml of ethyl acetate was added dropwise at room temperature, and then a reaction was performed for 2 hours. After the completion of the reaction, the reaction solution was washed with water, and the solvent was distilled off. To the residue, 20 ml of methanol and 10 ml of water were added, and the resultant was heated to 60° C. once and then cooled to 5° C. to deposit crystals. The deposited crystals were filtered off and vacuum dried to obtain the title compound as white crystals (1.9 g, yield 79% with respect to o-phenylenediamine). Melting point: 91-96° C.

$^1$H-NMR ($d_6$-DMSO): δ 2.31 (3H), 6.50 (1H), 6.80 (1H), 7.17 (1H), 7.33 (2H), 7.56 (2H), 7.63-7.68 (4H), 7.98 (1H), 8.35 (1H), 9.48 (1H), 9.88 (1H).

Example 19

Synthesis of N-(2-(3-(4-chlorophenyl)ureido)phenyl)-4-methylbenzenesulfonamide (Compound No. 217 in Table 1)

6.5 g (60 mmol) of o-phenylenediamine was added to 120 ml of dichloromethane, and the resultant was cooled to 5° C. To this solution, 9.2 g (60 mmol) of 4-chlorophenyl isocyanate was added dropwise at 10° C. or less, and then a reaction was performed at room temperature for 1 hour. After the completion of the reaction, deposited crystals were filtered off and vacuum dried to obtain 1-(2-aminophenyl)-3-(4-chlorophenyl)urea as white crystals (14.8 g).

To 100 ml of ethyl acetate, 12.9 g (50 mmol) of the 1-(2-aminophenyl)-3-(4-chlorophenyl)urea and 4.0 g (50 mmol) of pyridine were added. To this solution, a solution of 9.5 g (50 mmol) of p-toluenesulfonyl chloride in 100 ml of ethyl acetate was added dropwise at room temperature, and then a reaction was performed at 60° C. for 2 hours. After the completion of the reaction, the solvent was distilled off, 50 ml of methanol and 25 ml of water were added to the residue, and the resultant was heated to 60° C. once and then cooled to 5° C. The thus deposited crystals were filtered off and dried under reduced pressure to obtain the title compound as white crystals (18.4 g, yield 84% with respect to o-phenylenediamine). Melting point: 100-103° C.

$^1$H-NMR ($d_6$-DMSO): δ 2.34 (3H), 6.50 (1H), 6.80 (1H), 7.17 (1H), 7.35 (4H), 7.51 (2H), 7.57 (2H), 7.99 (1H), 8.26 (1H), 9.47 (1H), 9.62 (1H).

Example 20

Synthesis of N-(2-(3-(4-chlorophenyl)ureido)phenyl)-3-methylbenzenesulfonamide (Compound No. 216 in Table 1)

To 40 ml of ethyl acetate, 5.2 g (20 mmol) of 1-(2-aminophenyl)-3-(4-chlorophenyl)urea synthesized in the same manner as in Example 19 and 1.6 g (20 mmol) of pyridine were added. To this solution, 3.8 g (20 mmol) of m-toluenesulfonyl chloride was added dropwise at room temperature, and then a reaction was performed at 40° C. for 2 hours. After the completion of the reaction, the reaction solution was washed with water, the solvent was distilled off from an organic layer, and the residue was recrystallized from ethyl acetate/n-hexane. The thus deposited crystals were filtered off and vacuum dried to obtain the title compound as white crystals (7.6 g, yield 85% with respect to o-phenylenediamine). Melting point: 174-181° C.

$^1$H-NMR (d$_6$-DMSO): δ 2.33 (3H), 6.49 (1H), 6.80 (1H), 7.18 (1H), 7.35 (2H), 7.41-7.53 (6H), 7.99 (1H), 8.28 (1H), 9.51 (1H), 9.64 (1H).

Example 21

Synthesis of N-(2-(3-(4-chlorophenyl)ureido)phenyl)-2-methylbenzenesulfonamide (Compound No. 215 in Table 1)

To 40 ml of ethyl acetate, 5.2 g (20 mmol) of 1-(2-aminophenyl)-3-(4-chlorophenyl)urea synthesized in the same manner as in Example 19 and 1.6 g (20 mmol) of pyridine were added. To this solution, 3.8 g (20 mmol) of o-toluenesulfonyl chloride was added dropwise at room temperature, and then a reaction was performed at 40° C. for 2 hours. After the completion of the reaction, the reaction solution was washed with water, the solvent was distilled off from an organic layer, and the residue was recrystallized from ethyl acetate/n-hexane. The thus deposited crystals were filtered off and vacuum dried to obtain the title compound as white crystals (6.2 g, yield 68% with respect to o-phenylenediamine). Melting point: 192-194° C.

$^1$H-NMR (d$_6$-DMSO): δ 2.51 (3H), 6.39 (1H), 6.77 (1H), 7.17 (1H), 7.30-7.36 (3H), 7.41 (1H), 7.50-7.55 (3H), 7.65 (1H), 7.96 (1H), 8.33 (1H), 9.47 (1H), 9.69 (1H).

Example 22

Synthesis of N-(2-(3-(4-chlorophenyl)ureido)phenyl)benzenesulfonamide (Compound No. 214 in Table 1)

To 120 ml of ethyl acetate, 3.1 g (12 mmol) of 1-(2-aminophenyl)-3-(4-chlorophenyl)urea synthesized in the same manner as in Example 19 and 1.2 g (12 mmol) of triethylamine were added. To this solution, 2.1 g (12 mmol) of benzenesulfonyl chloride was added dropwise at room temperature, and the resultant was then refluxed for 7 hours. After the completion of the reaction, the reaction solution was washed with 2N hydrochloric acid, the solvent was distilled off from an organic layer, and the residue was crystallized from ethanol. The thus obtained crystals were filtered off and vacuum dried to obtain the title compound as white crystals (2.1 g, yield 43% with respect to 1-(2-aminophenyl)-3-(4-chlorophenyl)urea). Melting point: 160-161° C.

$^1$H-NMR (d$_6$-DMSO): δ 6.43 (1H), 6.75-6.79 (1H), 7.17 (1H), 7.34-7.36 (2H), 7.50-7.58 (4H), 7.64-7.71 (3H), 8.00-8.02 (1H), 8.30 (1H), 9.57 (1H), 9.67 (1H).

Example 23

Synthesis of 4-chloro-N-(2-(3-(4-chlorophenyl)ureido)phenyl)benzenesulfonamide (Compound No. 220 in Table 1)

To 120 ml of ethyl acetate, 3.1 g (12 mmol) of 1-(2-aminophenyl)-3-(4-chlorophenyl)urea synthesized in the same manner as in Example 19 and 1.2 g (12 mmol) of triethylamine were added. To this solution, 2.4 g (13.6 mmol) of 4-chlorobenzenesulfonyl chloride was added at room temperature, and the resultant was then refluxed for 4 hours. After the completion of the reaction, the reaction solution was washed with 2N hydrochloric acid, the solvent was distilled off from an organic layer, and the residue was crystallized from ethanol. The thus obtained crystals were filtered off and vacuum dried to obtain the title compound as white crystals (3.0 g, yield 58% with respect to 1-(2-aminophenyl)-3-(4-chlorophenyl)urea). Melting point: 103-106° C.

$^1$H-NMR (d$_6$-DMSO): δ 6.50 (1H), 6.82 (1H), 7.18 (1H), 7.32-7.34 (2H), 7.47-7.50 (2H), 7.61-7.67 (4H), 7.97-7.99 (1H), 8.26 (1H), 9.60 (1H), 9.65 (1H).

Example 24

Synthesis of N-(2-(3-phenylureido)phenyl)naphthalene-2-sulfonamide (Compound No. 354)

To 150 ml of ethyl acetate, 3.4 g (15 mmol) of 1-(2-aminophenyl)-3-phenylurea synthesized in the same manner as in Example 1 and 1.5 g (15 mmol) of triethylamine were added. To this solution, 3.4 g (15 mmol) of 2-naphthalene sulfonyl chloride (manufactured by Wako Pure Chemical Industries, Ltd., purity 95%) was added dropwise at room temperature, and the resultant was refluxed for 4 hours. After the completion of the reaction, the reaction solution was washed with 2N hydrochloric acid, the solvent was distilled off from an organic layer, and the residue was crystallized from ethanol. The thus obtained crystals were filtered off and vacuum dried to obtain the title compound as white crystals (3.8 g, yield 61% with respect to 1-(2-aminophenyl)-3-phenylurea). Melting point: 165-168° C.

$^1$H-NMR (d$_6$-DMSO): δ 6.42 (1H), 6.67 (1H), 6.98 (1H), 7.13 (1H), 7.29 (2H), 7.46 (2H), 7.62 (1H), 7.67-7.71 (1H), 7.80-7.82 (1H), 8.01-8.03 (2H), 8.07-8.13 (2H), 8.29 (1H), 8.34 (1H), 9.53 (1H), 9.67 (1H).

Example 25

Synthesis of N-(2-(3-phenylureido)phenyl)naphthalene-1-sulfonamide (Compound No. 355)

To 150 ml of ethyl acetate, 3.4 g (15 mmol) of 1-(2-aminophenyl)-3-phenylurea synthesized in the same manner as in Example 1 and 1.5 g (15 mmol) of triethylamine were added. To this solution, 3.4 g (15 mmol) of 1-naphthalene sulfonyl chloride (manufactured by Tokyo Chemical Industry Co., Ltd., purity 98%) was added in small aliquots at room temperature, and the resultant was refluxed for 5 hours. After the completion of the reaction, the reaction solution was washed with 2N hydrochloric acid, the solvent was distilled off from an organic layer, and the residue was crystallized from ethanol. The thus obtained crystals were filtered off and vacuum dried to obtain the title compound as white crystals (5.2 g, yield 83% with respect to 1-(2-aminophenyl)-3-phenylurea). Melting point: 199-201° C.

$^1$H-NMR (d$_6$-DMSO): δ 6.17 (1H), 6.61 (1H), 7.00 (1H), 7.10 (1H), 7.32 (2H), 7.47-7.49 (2H), 7.56 (1H), 7.66-7.70

(2H), 7.91-7.96 (2H), 8.10-8.12 (1H), 8.24-8.26 (1H), 8.32 (1H), 8.69-8.72 (1H), 9.47 (1H), 9.84 (1H).

Example 26

Synthesis of N-(4-(N-(2-(3-phenylureido)phenyl)sulfamoyl)phenyl)acetamide (Compound No. 5 in Table 1)

To 100 ml of ethyl acetate, 2.5 g (11 mmol) of 1-(2-aminophenyl)-3-phenylurea synthesized in the same manner as in Example 1 and 1.1 g (11 mmol) of triethylamine were added. To this solution, 2.6 g (11 mmol) of p-acetamidobenzenesulfonyl chloride (manufactured by Tokyo Chemical Industry Co., Ltd., purity 97%) was added in small aliquots at room temperature, and the resultant was refluxed for 5 hours. After the completion of the reaction, the reaction solution was washed with 2N hydrochloric acid, the solvent was distilled off from an organic layer, and the residue was crystallized from ethanol. The thus obtained crystals were filtered off and vacuum dried to obtain the title compound as white crystals (3.7 g, yield 79% with respect to 1-(2-aminophenyl)-3-phenylurea). Melting point: 196-200° C.

$^1$H-NMR ($d_6$-DMSO): δ 2.08 (3H), 6.46 (1H), 6.78 (1H), 6.98 (1H), 7.17 (1H), 7.30 (2H), 7.48 (2H), 7.61 (2H), 7.73 (2H), 8.02 (1H), 8.29 (1H), 9.42 (1H), 9.51 (1H), 10.3 (1H).

Example 27

Synthesis of 4-ethyl-N-(2-(3-phenylureido)phenyl)benzenesulfonamide (Compound No. 6 in Table 1)

To 150 ml of ethyl acetate, 3.4 g (15 mmol) of 1-(2-aminophenyl)-3-phenylurea synthesized in the same manner as in Example 1 and 1.5 g (15 mmol) of triethylamine were added. To this solution, 3.1 g (15 mmol) of p-ethylbenzenesulfonyl chloride (manufactured by Wako Pure Chemical Industries, Ltd., purity 98%) was added in small aliquots at room temperature, and the resultant was refluxed for 5 hours. After the completion of the reaction, the reaction solution was washed with 2N hydrochloric acid, the solvent was distilled off from an organic layer, and the residue was crystallized from acetone. The thus obtained crystals were filtered off and vacuum dried to obtain the title compound as white crystals (4.1 g, yield 68% with respect to 1-(2-aminophenyl)-3-phenylurea). Melting point: 86-89° C.

$^1$H-NMR ($d_6$-DMSO): δ 1.16 (3H), 2.65 (2H), 6.50 (1H), 6.78 (1H), 6.98 (1H), 7.16 (1H), 7.30 (2H), 7.38 (2H), 7.48 (2H), 7.61 (2H), 8.00 (1H), 8.26 (1H), 9.47 (1H), 9.48 (1H).

Example 28

Synthesis of 4-methoxy-N-(2-(3-phenylureido)phenyl)benzenesulfonamide (Compound No. 7 in Table 1)

To 150 ml of ethyl acetate, 3.4 g (15 mmol) of 1-(2-aminophenyl)-3-phenylurea synthesized in the same manner as in Example 1 and 1.5 g (15 mmol) of triethylamine were added. To this solution, 3.1 g (15 mmol) of p-methoxybenzenesulfonyl chloride (manufactured by Wako Pure Chemical Industries, Ltd., purity 98%) was added in small aliquots at room temperature, and the resultant was refluxed for 3 hours. After the completion of the reaction, the reaction solution was washed with 2N hydrochloric acid, the solvent was distilled off from an organic layer, and the residue was crystallized from ethanol. The thus obtained crystals were filtered off and vacuum dried to obtain the title compound as white crystals (4.5 g, yield 76% with respect to 1-(2-aminophenyl)-3-phenylurea). Melting point: 164-166° C.

$^1$H-NMR ($d_6$-DMSO): δ 3.79 (3H), 6.50 (1H), 6.79 (1H), 6.98 (1H), 7.05-7.07 (2H), 7.17 (1H), 7.30 (2H), 7.48 (2H), 7.61 (2H), 8.01 (1H), 8.28 (1H), 9.38 (1H), 9.50 (1H).

(2) Preparation and Test of Thermal Recording Paper (Part 1)

1) Preparation of Thermal Recording Paper

[Evaluation Sample 1]

| Dispersion solution of color former (solution A) | |
| --- | --- |
| 3-Di-n-butylamino-6-methyl-7-anilinofluoran | 16 parts |
| 10% Aqueous solution of polyvinyl alcohol | 84 parts |
| Dispersion solution of color-developing agent (solution B) | |
| Compound of Example 1 | 16 parts |
| 10% Aqueous solution of polyvinyl alcohol | 84 parts |
| Dispersion solution of filler (solution C) | |
| Fired kaolin | 27.8 parts |
| 10% Aqueous solution of polyvinyl alcohol | 26.2 parts |
| Water | 71 parts |

(parts: parts by mass)

Each mixture having the composition of the solution A, B, or C was sufficiently ground with a sand grinder to prepare dispersion solutions of the components of the solutions A to C, and 1 part by mass of the solution A, 2 parts by mass of the solution B, and 4 parts by mass of the solution C were mixed to prepare a coating solution. This coating solution was applied to white paper using a wire rod (manufactured by Webster, Wire Bar No. 12), the paper was dried, and then, calendering treatment was performed to prepare thermal recording paper (coating solution: approximately 5.5 g/m$^2$ in terms of dry mass).

[Evaluation Samples 2 to 28]

Thermal paper was prepared in the same manner as described with respect to the evaluation sample 1 above except that the compound of each of Examples 2 to 28 was used instead of the compound of Example 1 in the dispersion solution of the color-developing agent (solution B) of the evaluation sample 1. The relationship between the evaluation sample No. and the color-developing agent is shown in Table 2-1.

[Evaluation Sample 29]

Thermal paper was prepared in the same manner as described with respect to the evaluation sample 1 above except that D-8 was used instead of the compound of Example 1 in the dispersion solution of the color-developing agent (solution B) of the evaluation sample 1.

2) Saturated Color Development Test

In each thermal recording paper prepared as the evaluation samples 1 to 29, saturated color development was caused in a checkered pattern by using a thermal printing tester (manufactured by Ohkura Electric Co., Ltd., Model TH-PMD) under conditions of a printing voltage of 17 V and a pulse width of 1.8 ms. The optical concentration attained after the color development was measured by a spectrophotometer (Spectroeye LT, manufactured by X-rite). The results are shown in Table 2-1.

TABLE 2-1

RESULTS OF SATURATED COLOR DEVELOPMENT TEST

| EVALUATION SAMPLE | COLOR-DEVELOPING AGENT | SATURATED CONCENTRATION |
|---|---|---|
| 1 | EXAMPLE 1 | 1.19 |
| 2 | EXAMPLE 2 | 1.18 |
| 3 | EXAMPLE 3 | 1.20 |
| 4 | EXAMPLE 4 | 1.22 |
| 5 | EXAMPLE 5 | 1.14 |
| 6 | EXAMPLE 6 | 1.09 |
| 7 | EXAMPLE 7 | 1.05 |
| 8 | EXAMPLE 8 | 1.04 |
| 9 | EXAMPLE 9 | 1.13 |
| 10 | EXAMPLE 10 | 1.07 |
| 11 | EXAMPLE 11 | 1.09 |
| 12 | EXAMPLE 12 | 1.08 |
| 13 | EXAMPLE 13 | 1.21 |
| 14 | EXAMPLE 14 | 0.96 |
| 15 | EXAMPLE 15 | 1.04 |
| 16 | EXAMPLE 16 | 1.14 |
| 17 | EXAMPLE 17 | 1.22 |
| 18 | EXAMPLE 18 | 1.22 |
| 19 | EXAMPLE 19 | 1.17 |
| 20 | EXAMPLE 20 | 1.16 |
| 21 | EXAMPLE 21 | 1.13 |
| 22 | EXAMPLE 22 | 1.23 |
| 23 | EXAMPLE 23 | 1.23 |
| 24 | EXAMPLE 24 | 1.12 |
| 25 | EXAMPLE 25 | 0.99 |
| 26 | EXAMPLE 26 | 0.91 |
| 28 | EXAMPLE 28 | 1.18 |
| 29 | D-8 | 1.28 |

It was revealed from the results shown in Table 2-1 that the compounds of the present invention show good color development when used together with a color former and their color development is comparable to that of D-8, that is, a conventionally used color-developing agent.

3) Plasticizer Resistance Test

A portion of each thermal recording paper prepared as the evaluation samples 2, 3, 7, 8, 11, 13, 16, 18, 19, 23, 24 and 28 was cut off, and the saturated color development was caused in the same manner as described above. Subsequently, a vinyl chloride cling film (one containing a plasticizer) was brought into close contact with the color-developed surface and the other surface of each test paper, and the test paper was kept in that state at 40° C. for 4 hours. After the test, the optical concentration was measured by the spectrophotometer (Spectroeye LT, manufactured by X-rite). The measurement results are shown in Table 2-2.

TABLE 2-2

RESULTS OF PLASTICIZER RESISTANCE TEST

| EVALUATION SAMPLE | SATURATED CONCENTRATION |
|---|---|
| 2 | 0.66 |
| 3 | 0.59 |
| 7 | 0.53 |
| 8 | 0.58 |
| 11 | 0.73 |
| 13 | 0.93 |
| 16 | 0.84 |
| 18 | 0.84 |
| 19 | 0.93 |
| 23 | 0.92 |
| 24 | 0.77 |
| 28 | 0.77 |

It was revealed from the results shown in Table 2-2 that the compounds of the present invention are good in the plasticizer resistance.

(3) Preparation and Test of Thermal Recording Paper (Part 2)

1) Preparation of Thermal Recording Paper

[Evaluation Sample 30] Dispersion Solution for Undercoat Layer

| Fired kaolin | 27.8 parts |
|---|---|
| 10% Aqueous solution of polyvinyl alcohol | 26.2 parts |
| Water | 71 parts |
| Dispersion solution of color former (solution A) | |
| 3-Di-n-butylamino-6-methyl-7-anilinofluoran | 16 parts |
| 10% Aqueous solution of polyvinyl alcohol | 84 parts |
| Dispersion solution of color-developing agent (solution B) | |
| Compound of Example 1 | 16 parts |
| 10% Aqueous solution of polyvinyl alcohol | 84 parts |
| Dispersion solution of filler (solution C) | |
| Fired kaolin | 27.8 parts |
| 10% Aqueous solution of polyvinyl alcohol | 26.2 parts |
| Water | 71 parts |

(parts: parts by mass)

The dispersion solution for an undercoat layer was applied to white paper in an amount of approximately 8 g/m$^2$ in terms of dry mass, and the paper was dried to form the undercoat layer thereon.

Next, each mixture having the composition of the solution A, B, or C was sufficiently ground with a sand grinder to prepare dispersion solutions of the components of the solutions A to C, and 1 part by mass of the solution A, 2 parts by mass of the solution B, and 4 parts by mass of the solution C were mixed to prepare a coating solution. This coating solution was applied to the paper having the undercoat layer thereon by using the wire rod (manufactured by Webster, Wire Bar No. 12), the paper was dried, and then, calendering treatment was performed to prepare thermal recording paper (coating solution: approximately 5.5 g/m$^2$ in terms of dry mass).

[Evaluation Samples 31 and 32]

Thermal paper was prepared in the same manner as described with respect to the evaluation sample 30 above except that the compound of Example 4 or D-8 was used instead of the compound of Example 1 in the dispersion solution of the color-developing agent (solution B) of the evaluation sample 30. The relationship between the evaluation sample No. and the color-developing agent is shown in Table 3.

[Evaluation sample 33]

| Dispersion solution of color former (solution A) | |
|---|---|
| 3-Di-n-butylamino-6-methyl-7-anilinofluoran | 16 parts |
| 10% Aqueous solution of polyvinyl alcohol | 84 parts |
| Dispersion solution of color-developing agent (solution B) | |
| Compound of Example 1 | 16 parts |
| 10% Aqueous solution of polyvinyl alcohol | 84 parts |
| Dispersion solution of filler (solution C) | |
| Fired kaolin | 27.8 parts |
| 10% Aqueous solution of polyvinyl alcohol | 26.2 parts |
| Water | 71 parts |
| Dispersion solution of assistant (solution D) | |
| DH-43 | 16 parts |
| 10% Aqueous solution of polyvinyl alcohol | 84 parts |

(parts: parts by mass)

Each mixture having the composition of the solution A, B, C, or D was sufficiently ground with a sand grinder to prepare dispersion solutions of the components of the solutions A to D, and 1 part by mass of the solution A, 2 parts by mass of the solution B, 4 parts by mass of the solution C and 1 part by mass of the solution D were mixed to prepare a coating solution. This coating solution was applied to white paper using the wire rod (manufactured by Webster, Wire Bar No. 12), the paper was dried, and then, calendering treatment was performed to prepare thermal recording paper (coating solution: approximately 5.5 g/m² in terms of dry mass).

[Evaluation Samples 34 to 44]

Thermal paper was prepared in the same manner as described with respect to the evaluation sample 33 above except that the compound shown as a color-developing agent in Table 3 was used instead of the compound of Example 1 and the compound shown as an additive in Table 3 was used instead of DH-43 in the dispersion solution of the color-developing agent (solution B) of the evaluation sample 33. The relationship among the evaluation sample No., the color-developing agent and the additive is shown in Table 3.

[Evaluation Samples 45 to 47]

Thermal paper was prepared in the same manner as described with respect to the evaluation sample 1 above except that Black-305 was used instead of 3-di-n-butylamino-6-methyl-7-anilinofluoran in the dispersion solution of the color former (solution A) of the evaluation sample 1. The relationship among the evaluation sample No., the color-developing agent and the color former is shown in Table 3.

TABLE 3

LIST OF ADDITIVES

| EVALUATION SAMPLE | COLOR-DEVELOPING AGENT | UNDER-COAT | ADDITIVE | color former |
|---|---|---|---|---|
| 1 | EXAMPLE 1 | | | 3-Di-n-butylamino-6-methyl-7-anilinofluoran |
| 4 | EXAMPLE 4 | | | |
| 29 | D-8 | | | |
| 30 | EXAMPLE 1 | formed | | |
| 31 | EXAMPLE 4 | formed | | |
| 32 | D-8 | formed | | |
| 33 | EXAMPLE 1 | | DH-43 | |
| 34 | EXAMPLE 4 | | DH-43 | |
| 35 | D-8 | | DH-43 | |
| 36 | EXAMPLE 1 | | D-90 | |
| 37 | EXAMPLE 4 | | D-90 | |
| 38 | D-8 | | D-90 | |
| 39 | EXAMPLE 1 | | UU | |
| 40 | EXAMPLE 4 | | UU | |
| 41 | D-8 | | UU | |
| 42 | EXAMPLE 1 | | EGMTE | |
| 43 | EXAMPLE 4 | | EGMTE | |
| 44 | D-8 | | EGMTE | |
| 45 | EXAMPLE 1 | | | Black-305 |
| 46 | EXAMPLE 4 | | | |
| 47 | D-8 | | | |

2) Background Stability Test

Each test paper of the evaluation samples 1, 4 and 49 to 47 was subjected to a stability test under conditions shown below before and after a test. The results are summarized in Table 4.

[Before Test]

A portion of each thermal recording paper prepared as the evaluation samples 1, 4 and 29 to 47 was cut off, and the optical concentration of the background was measured by the spectrophotometer (Spectroeye LT, manufactured by X-rite).

[Heat Resistance Test]

A portion of each thermal recording paper prepared as the evaluation samples 1, 4 and 29 to 47 was cut off and kept in a thermostat (trade name: DK-400, manufactured by Yamato Scientific Co., Ltd.) at respective temperatures of 80° C., 90° C. and 100° C. for 24 hours. The optical concentration of the background after thus being kept was measured by the spectrophotometer (Spectroeye LT, manufactured by X-rite).

TABLE 4

RESULTS OF BACKGROUND HEAT RESISTANCE TEST

| EVALUATION SAMPLE | BEFORE TEST | BACKGROUND HEAT RESISTANCE | | |
|---|---|---|---|---|
| | | 80° C. | 90° C. | 100° C. |
| 1 | 0.08 | 0.09 | 0.09 | 0.09 |
| 4 | 0.09 | 0.10 | 0.11 | 0.13 |
| 29 | 0.11 | 0.14 | 0.21 | 0.30 |
| 30 | 0.07 | 0.08 | 0.08 | 0.09 |
| 31 | 0.09 | 0.10 | 0.11 | 0.13 |
| 32 | 0.11 | 0.14 | 0.21 | 0.30 |
| 33 | 0.08 | 0.10 | 0.10 | 0.12 |
| 34 | 0.09 | 0.11 | 0.13 | 0.18 |
| 35 | 0.12 | 0.21 | 0.43 | 0.70 |
| 36 | 0.08 | 0.09 | 0.17 | 0.45 |
| 37 | 0.10 | 0.12 | 0.24 | 0.68 |
| 38 | 0.11 | 0.30 | 0.85 | 1.12 |
| 39 | 0.08 | 0.08 | 0.09 | 0.09 |
| 40 | 0.09 | 0.10 | 0.10 | 0.13 |
| 41 | 0.11 | 0.14 | 0.21 | 0.60 |
| 42 | 0.07 | 0.08 | 0.11 | 0.15 |
| 43 | 0.08 | 0.12 | 0.18 | 0.30 |
| 44 | 0.10 | 0.25 | 0.61 | 0.96 |
| 45 | 0.08 | 0.09 | 0.09 | 0.10 |
| 46 | 0.09 | 0.09 | 0.11 | 0.13 |
| 47 | 0.12 | 0.14 | 0.18 | 0.36 |

On the basis of Table 4, the compounds of the present invention were free from background fogging because no color was developed before the test, and the background heat resistance was particularly good. The evaluation samples using D-8, that is, a conventionally used color-developing agent, are the samples 29, 32, 35, 38, 41, 44 and 47, and it was revealed through comparison with the values of these samples that the compounds of the present invention are excellent in the background heat resistance.

3) Image Stability Test

Each test paper of the evaluation samples 1, 4 and 29 to 47 was subjected to a stability test under conditions shown below. The evaluation made on the basis of the test results is summarized in Table 5.

[Before Test]

A portion of each thermal recording paper prepared as the evaluation samples 1, 4 and 29 to 47 was cut off and colored under conditions of a printing voltage of 17 V and a pulse width of 1.8 ms by using the thermal printing tester (trade name: model TH-PMH, manufactured by Ohkura Electric Co., Ltd.), and the concentration of the colored image was measured by the spectrophotometer (Spectroeye LT, manufactured by X-rite).

[Heat resistance Test]

A portion of each thermal recording paper prepared as the evaluation samples 1, 4 and 29 to 47 was cut off, and the saturated color development was caused in the same manner as before the test. Subsequently, each test paper was kept in the thermostat (trade name: DK-400, manufactured by Yamato Scientific Co., Ltd.) at respective temperatures of 80° C., 90° C. and 100° C. for 24 hours. The optical concentration of the background after thus being kept was measured by the spectrophotometer (Spectroeye LT, manufactured by X-rite).

[Plasticizer Resistance Test]

A portion of each thermal recording paper prepared as the evaluation samples 1, 4 and 29 to 47 was cut off, and the saturated color development was caused in the same manner as before the test. Subsequently, a vinyl chloride cling film (one containing a plasticizer) was brought into close contact with the color-developed surface and the other surface of each test paper, and the test paper was kept in that state at 40° C. for 4 hours. After the test, the optical concentration was measured by the spectrophotometer (Spectroeye LT, manufactured by X-rite).

[Water Resistance Test]

A portion of each thermal recording paper prepared as the evaluation samples 1, 4 and 29 to 47 was cut off, and the saturated color development was caused in the same manner as before the test. Subsequently, each test paper was dipped in pure water at 25° C. for 7 days. After the test, the optical concentration was measured by the spectrophotometer (Spectroeye LT, manufactured by X-rite).

[Alcohol Resistance Test]

A portion of each thermal recording paper prepared as the evaluation samples 1, 4 and 29 to 47 was cut off, and the saturated color development was caused in the same manner as before the test. Subsequently, each test paper was dipped in a 35% ethanol solution at 25° C. for 1 hour. After the test, the optical concentration was measured by the spectrophotometer (Spectroeye LT, manufactured by X-rite).

41, 44 and 47, and it was revealed through comparison with the values of these samples that the compounds of the present invention are excellent in the image heat resistance.

Besides, it was found that the plasticizer resistance is improved by adding a stabilizer.

It was found that the water resistance is also good. The values of the water resistance were comparable to those attained by D-8.

It was found that the alcohol resistance is also improved by adding a stabilizer. Besides, it was found that the values are considerably good as compared with those attained by D-8.

Even if the color former was changed, good image stability was similarly shown.

(4) Comparison in Plasticizer Resistance with Conventional Compound

A compound having the following structure was synthesized by a synthesis method described in Japanese unexamined Patent Application Publication No. 11-268421. This compound is herein designated as the "color-developing agent N".

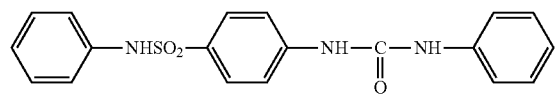

Thermal paper was prepared in the same manner as described with respect to the evaluation sample 1 above except that the color-developing agent N was used instead of the compound of Example 1 in the dispersion solution of the color-developing agent (solution B) of the evaluation sample 1. This evaluation sample is designated as the evaluation sample 48.

TABLE 5

RESULTS OF IMAGE STABILITY

| EVALUATION SAMPLE | BEFORE TEST | IMAGE HEAT RESISTANCE | | | PLASTICIZER RESISTANCE | WATER RESISTANCE | ALCOHOL RESISTANCE |
|---|---|---|---|---|---|---|---|
| | | 80° C. | 90° C. | 100° C. | | | |
| 1 | 1.19 | 1.20 | 1.10 | 0.96 | 0.27 | 1.06 | 0.72 |
| 4 | 1.22 | 1.28 | 1.27 | 1.07 | 0.50 | 1.04 | 0.62 |
| 29 | 1.28 | 1.33 | 1.33 | 1.31 | 0.24 | 0.86 | 0.19 |
| 30 | 1.14 | 1.20 | 1.18 | 0.94 | 0.20 | 0.96 | 0.44 |
| 31 | 1.22 | 1.28 | 1.27 | 1.07 | 0.50 | 1.04 | 0.62 |
| 32 | 1.28 | 1.33 | 1.33 | 1.31 | 0.24 | 0.86 | 0.19 |
| 33 | 1.11 | 1.16 | 1.17 | 1.14 | 0.55 | 1.05 | 1.02 |
| 34 | 1.22 | 1.26 | 1.27 | 1.26 | 0.80 | 1.12 | 1.00 |
| 35 | 1.28 | 1.32 | 1.32 | 1.32 | 0.35 | 1.11 | 0.59 |
| 36 | 1.15 | 1.18 | 1.23 | 1.18 | 0.98 | 1.03 | 0.96 |
| 37 | 1.22 | 1.26 | 1.30 | 1.26 | 1.07 | 1.09 | 0.99 |
| 38 | 1.27 | 1.32 | 1.33 | 1.33 | 1.01 | 1.08 | 0.61 |
| 39 | 1.09 | 1.11 | 1.04 | 1.03 | 0.81 | 1.01 | 1.02 |
| 40 | 1.20 | 1.23 | 1.20 | 1.21 | 0.96 | 1.08 | 1.04 |
| 41 | 1.26 | 1.30 | 1.31 | 1.29 | 1.08 | 1.14 | 1.00 |
| 42 | 1.26 | 1.10 | 1.12 | 0.94 | 0.47 | 0.98 | 0.49 |
| 43 | 1.29 | 1.06 | 1.25 | 1.11 | 0.75 | 1.00 | 0.44 |
| 44 | 1.33 | 1.32 | 1.31 | 1.28 | 0.52 | 0.72 | 0.14 |
| 45 | 1.24 | 1.27 | 1.13 | 0.99 | 0.57 | 1.04 | 0.75 |
| 46 | 1.27 | 1.32 | 1.28 | 1.13 | 0.79 | 1.06 | 0.71 |
| 47 | 1.30 | 1.32 | 1.33 | 1.32 | 0.44 | 0.87 | 0.21 |

It was found from Table 5 that the image heat resistance of the compounds of the present invention is good. The evaluation samples using D-8, that is, the conventionally used color-developing agent, are the samples 29, 32, 35, 38,

[Image Plasticizer Resistance (Strict) Test]

Since the above-described plasticizer resistance test is a simple evaluation method for the plasticizer resistance, the plasticizer resistance was evaluated by the following method for purpose of improving the accuracy.

A portion of each thermal recording paper prepared as the evaluation samples 1, 4, 29 and 48 was cut off, and the saturated color development was caused in the same manner as before the test for evaluating the image stability. Subsequently, Polymawrap® (manufactured by Shin-Etsu Polymer Co., Ltd., material: vinyl chloride resin) was brought into close contact with the color-developed surface and the other surface of each test paper, and the test paper was kept in that state at 40° C. for 4 hours. After peeling off Polymawrap from the test paper, five portions where the print was light (hereinafter referred to as the light portions) and five portions where the print was dark (hereinafter referred to as the dark portions) were visually selected for measuring the optical concentration by the spectrophotometer (Spectroeye LT, manufactured by X-rite).

The results are shown in Table 6.

TABLE 6

| | | DIFFERENCE IN EVALUATION RESULT FROM COLOR-DEVELOPING AGENT N | |
|---|---|---|---|
| EVALUATION SAMPLE | BEFORE TEST | PLASTICIZER RESISTANCE (STRICT) | |
| | | DARK PORTIONS | LIGHT PORTIONS |
| 1 | 1.19 | 0.54 | 0.40 |
| 4 | 1.22 | 0.71 | 0.59 |
| 29 | 1.28 | 0.66 | 0.48 |
| 48 | 1.20 | 0.15 | 0.15 | except that the compounds shown as a color-developing agent in Table 7 were used in a mixing ratio shown in Table 7 instead of the compound of Example 1 in the dispersion solution of the color-developing agent (solution B) of the evaluation sample 30. The relationship among the evaluation sample No., the color-developing agent and the mixing ratio is shown in Table 7.

TABLE 7

| | EXAMPLES OF MIXED COLOR-DEVELOPING AGENT | | |
|---|---|---|---|
| EVALUATION SAMPLE | COLOR-DEVELOPING AGENT | | MIXING RATIO |
| 49 | EXAMPLE 4 | D-8 | 9:1 |
| 50 | | | 5:5 |
| 51 | | | 1:9 |

2) Image Stability Test

The evaluation samples 49 to 51 were subjected to the measurement in the same manner as described with respect to the evaluation of the image stability above. The results are shown in Table 8.

TABLE 8

| | | RESULTS OF IMAGE STABILITY | | | | | |
|---|---|---|---|---|---|---|---|
| EVALUATION SAMPLE | BEFORE TEST | IMAGE HEAT RESISTANCE | | | PLASTICIZER RESISTANCE | WATER RESISTANCE | ALCOHOL RESISTANCE |
| | | 80° C. | 90° C. | 100° C. | | | |
| 49 | 1.26 | 1.31 | 1.27 | 1.16 | 0.87 | 1.09 | 0.39 |
| 50 | 1.27 | 1.33 | 1.33 | 1.23 | 0.89 | 1.12 | 0.38 |
| 51 | 1.28 | 1.34 | 1.33 | 1.31 | 0.56 | 1.04 | 0.23 |

It was found from Table 6 that the compounds of the present invention (evaluation samples 1 and 4) have plasticizer resistance equivalent to that of the conventional phenol type color-developing agent (evaluation sample 29) in the plasticizer resistance (strict) test. Besides, since the printed image became rather light and was influenced by a plasticizer contained in the cling film in using the known non-phenol color-developing agent (evaluation sample 48), even though the compounds of the present invention, which are the non-phenol color-developing agents as well, were found to have better plasticizer resistance than that of the known non-phenol color-developing agent.

(5) Preparation and Test of Thermal Recording Paper (Part 3)

1) Preparation of Thermal Recording Paper

[Evaluation Samples 49 to 51]

Thermal paper was prepared in the same manner as described with respect to the evaluation sample 30 above

The invention claimed is:

1. A recording composition containing a color former, wherein the recording composition contains at least one compound selected from the group consisting of:

a compound represented by the following formula (I):

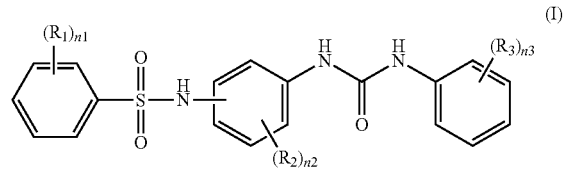

where:
$R_1$, $R_2$, and $R_3$ each independently represents a hydrogen atom, a halogen atom, a nitro group, a $C_1$-$C_6$ alkyl group, a $C_1$-$C_6$ alkoxyl group, a $C_2$-$C_6$ alkenyl group, a $C_1$-$C_6$ fluoroalkyl group, a $N(R_4)_2$ group, $NHCOR_5$, an optionally substituted phenyl group, or an optionally substituted benzyl group;

$R_4$ represents a hydrogen atom, a phenyl group, a benzyl group, or a $C_1$-$C_6$ alkyl group;

$R_5$ represents a $C_1$-$C_6$ alkyl group;

n1 and n3 each independently represents any integer of 1 to 5; and n2 represents any integer of 1 to 4;

a compound represented by the following formula (II):

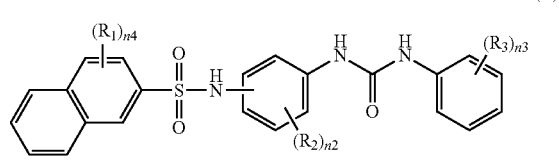

where:
R$_1$, R$_2$, R$_3$, n2, and n3 are as defined above; and
n4 represents any integer of 1 to 7); and a compound represented by the following formula (III):

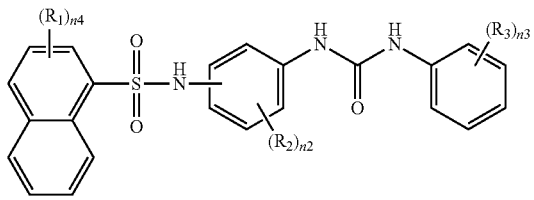

where R$_1$, R$_2$, R$_3$, n2, n3, and n4 are as defined above.

2. The recording composition according to claim 1, wherein the formula (I) is the following formula (IV):

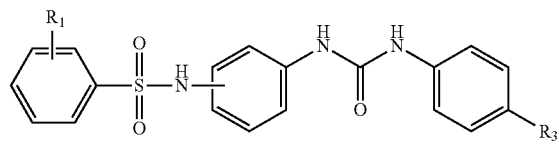

where R$_1$ and R$_3$ are as defined in claim 1.

3. The recording composition according to claim 2, wherein the formula (I) is the following formula (V):

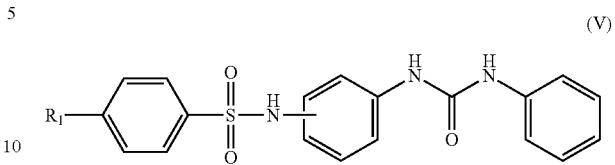

where R$_1$ is as defined in claim 1.

4. A recording sheet having a recording composition layer formed from the recording composition according to claim 3 on a support.

5. A recording sheet having a recording composition layer formed from the recording composition according to claim 2 on a support.

6. The recording composition according to claim 1, wherein the formula (I) is the following formula (V):

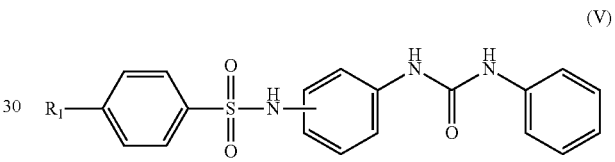

where R$_1$ is as defined in claim 1.

7. A recording sheet having a recording composition layer formed from the recording composition according to claim 6 on a support.

8. A recording sheet having a recording composition layer formed from the recording composition according to claim 1 on a support.

* * * * *

UNITED STATES PATENT AND TRADEMARK OFFICE
CERTIFICATE OF CORRECTION

PATENT NO. : 9,518,011 B2
APPLICATION NO. : 14/441941
DATED : December 13, 2016
INVENTOR(S) : Hiroshi Sakai et al.

It is certified that error appears in the above-identified patent and that said Letters Patent is hereby corrected as shown below:

In the Specification

In Table 1, Column 12, cancel the text presented in the "EXAMPLE" and "MELTING POINT(°C)" columns for COMPOUND No 31 and insert the text in the "EXAMPLE" and "MELTING POINT(°C)" columns for COMPOUND No 35, as shown below.

|         | COMPOUND No. | EXAMPLE | MELTING POINT(°C) |
|---------|--------------|---------|-------------------|
| error   | 31           | 14      | 173-175           |
| correct | --35         | 14      | 173-175--.        |

In Table 1, Column 24, cancel the text presented in the "EXAMPLE" and "MELTING POINT(°C)" columns for COMPOUND No 219 and insert the text in the "EXAMPLE" and "MELTING POINT(°C)" columns for COMPOUND No 220, as shown below.

|         | COMPOUND No. | EXAMPLE | MELTING POINT(°C) |
|---------|--------------|---------|-------------------|
| error   | 219          | 23      | 103-106           |
| correct | --220        | 23      | 103-106--.        |

Column 42, Line 12, "the metal salts of the aromatic" should read --the metal salts of the aromatic carboxylic acids.--.

Column 45, Line 50, "$d_5$-DMSO" should read --$d_6$-DMSO--.

Column 50, Line 65, "2.36 (311)" should read --2.36 (3H)--.

Column 55, Line 47, "$d_5$-DMSO" should read --$d_6$-DMSO--.

Column 59, Line 58, "1, 4 and 49" should read --1, 4 and 29--.

Signed and Sealed this
Twenty-sixth Day of December, 2017

Joseph Matal
*Performing the Functions and Duties of the
Under Secretary of Commerce for Intellectual Property and
Director of the United States Patent and Trademark Office*